(12) United States Patent
Kimball et al.

(10) Patent No.: US 11,272,950 B2
(45) Date of Patent: Mar. 15, 2022

(54) METHODS AND FEATURES FOR COUPLING ULTRASONIC SURGICAL INSTRUMENT COMPONENTS TOGETHER

(71) Applicant: Ethicon LLC, Guaynabo, PR (US)

(72) Inventors: Cory G. Kimball, Hamilton, OH (US); David A. Witt, Maineville, OH (US); William E. Clem, Bozeman, MT (US); Nathan D. Grubbs, West Chester, OH (US); Daniel J. Prenger, Loveland, OH (US); Ashvani K. Madan, Mason, OH (US)

(73) Assignee: Cilag GmbH International, Zug (CH)

( * ) Notice: Subject to any disclaimer, the term of this patent is extended or adjusted under 35 U.S.C. 154(b) by 237 days.

(21) Appl. No.: 16/248,831

(22) Filed: Jan. 16, 2019

(65) Prior Publication Data

US 2019/0216490 A1 Jul. 18, 2019

Related U.S. Application Data

(63) Continuation of application No. 14/087,352, filed on Nov. 22, 2013, now Pat. No. 10,226,271.

(51) Int. Cl.
*A61B 17/32* (2006.01)
*A61B 90/00* (2016.01)
(Continued)

(52) U.S. Cl.
CPC ...... *A61B 17/320068* (2013.01); *A61B 90/03* (2016.02); *A61B 50/00* (2016.02);
(Continued)

(58) Field of Classification Search
CPC .... A61B 17/320068; A61B 17/320092; A61B 2017/320069; A61B 2017/32007;
(Continued)

(56) References Cited

U.S. PATENT DOCUMENTS 4,188,952 A 2/1980 Loschilov et al.
4,274,826 A 6/1981 Huey et al.
(Continued)

FOREIGN PATENT DOCUMENTS

DE 20118699 U1 4/2003
EP 1946708 A2 7/2008

OTHER PUBLICATIONS

Chinese Office Action and Search Report dated Apr. 4, 2018 for Application No. CN 201480063722.X, 4 pgs.
(Continued)

*Primary Examiner* — Kathleen S Holwerda

(74) *Attorney, Agent, or Firm* — Frost Brown Todd LLC

(57) ABSTRACT

A surgical apparatus comprises a transducer assembly and a shaft assembly. The transducer assembly is operable to convert electrical power into ultrasonic vibrations. The shaft assembly comprises an ultrasonic waveguide, a sheath, a shroud, and a torque transfer assembly. The waveguide is configured to couple with the transducer assembly. The waveguide is disposed within the sheath. The sheath extends through the shroud. The torque transfer assembly is contained within the shroud. The torque transfer assembly is configured to transfer a predetermined range of torque from the shroud to the waveguide to thereby couple the waveguide with the transducer assembly. The torque transfer assembly is further configured to prevent transfer of torque from the shroud to the waveguide beyond an upper limit of the predetermined range.

20 Claims, 69 Drawing Sheets

(51) Int. Cl.
  *A61B 17/00* (2006.01)
  *A61B 50/00* (2016.01)
(52) U.S. Cl.
  CPC ............... *A61B 2017/0046* (2013.01); *A61B 2017/00402* (2013.01); *A61B 2017/00477* (2013.01); *A61B 2017/320069* (2017.08); *A61B 2017/320071* (2017.08); *A61B 2017/320089* (2017.08); *A61B 2017/320098* (2017.08); *A61B 2090/031* (2016.02); *A61B 2090/0801* (2016.02)
(58) Field of Classification Search
  CPC ....... A61B 2017/320071; A61B 2017/320072; A61B 2017/320082; A61B 2017/320084; A61B 2017/320088; A61B 2017/320089; A61B 2017/320093; A61B 2017/320094; A61B 2017/320095; A61B 2017/320097; A61B 2017/320098; A61B 2017/0046; A61B 2017/004477; A61B 2090/031; A61B 2017/00402; F16D 7/002; F16D 7/048
  See application file for complete search history.

(56) References Cited

U.S. PATENT DOCUMENTS

| | | | |
|---|---|---|---|
| 4,315,745 A | 2/1982 | Murata | |
| D285,835 S | 9/1986 | Hanses | |
| 4,998,350 A | 3/1991 | Thompson | |
| D318,116 S | 7/1991 | Michelson | |
| 5,057,119 A | 10/1991 | Clark et al. | |
| 5,059,210 A | 10/1991 | Clark et al. | |
| D340,981 S | 11/1993 | Hood et al. | |
| D344,799 S | 3/1994 | Hood et al. | |
| 5,322,055 A | 6/1994 | Davison et al. | |
| 5,342,380 A | 8/1994 | Hood | |
| 5,466,020 A | 11/1995 | Page et al. | |
| 5,776,155 A * | 7/1998 | Beaupre | A61B 17/320068 606/169 |
| 5,810,859 A | 9/1998 | DiMatteo et al. | |
| 5,873,873 A | 2/1999 | Smith et al. | |
| 5,980,510 A | 11/1999 | Tsonton et al. | |
| 5,993,477 A | 11/1999 | Vaitekunas et al. | |
| 6,036,667 A | 3/2000 | Manna et al. | |
| 6,063,050 A | 5/2000 | Manna et al. | |
| D443,058 S | 5/2001 | Mulhauser et al. | |
| 6,325,811 B1 | 12/2001 | Messerly | |
| 6,352,532 B1 | 3/2002 | Kramer et al. | |
| 6,682,544 B2 | 1/2004 | Mastri et al. | |
| 6,716,028 B2 | 4/2004 | Rahman et al. | |
| 6,773,444 B2 | 8/2004 | Messerly | |
| 6,783,524 B2 | 8/2004 | Anderson et al. | |
| 6,811,399 B2 | 11/2004 | Rahman et al. | |
| 7,011,520 B2 | 3/2006 | Rahman et al. | |
| D571,468 S | 6/2008 | Wu | |
| 7,604,479 B2 | 10/2009 | Buchanan | |
| 8,057,498 B2 | 11/2011 | Robertson | |
| 8,114,104 B2 | 2/2012 | Young et al. | |
| D658,285 S | 4/2012 | Ryshkus et al. | |
| 8,231,644 B2 | 7/2012 | Onaga | |
| 8,435,258 B2 | 5/2013 | Young et al. | |
| 8,461,744 B2 | 6/2013 | Wiener et al. | |
| 8,591,536 B2 | 11/2013 | Robertson | |
| 8,623,027 B2 | 1/2014 | Price et al. | |
| D700,331 S | 2/2014 | Lim | |
| D715,437 S | 10/2014 | Busch | |
| D733,300 S | 6/2015 | Bennett | |
| 9,095,367 B2 | 8/2015 | Olson et al. | |
| D742,007 S | 10/2015 | Schuetz | |
| D749,730 S | 2/2016 | Dietz et al. | |
| D776,276 S | 1/2017 | Witt et al. | |
| 9,848,900 B2 | 12/2017 | Witt et al. | |
| 10,172,636 B2 | 1/2019 | Stulen et al. | |
| 10,226,271 B2 | 3/2019 | Kimball et al. | |
| 2004/0232201 A1 * | 11/2004 | Wenchell | A61B 17/068 227/176.1 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2007/0282335 A1 * | 12/2007 | Young | B25B 23/142 606/50 |
| 2008/0046000 A1 * | 2/2008 | Lee | A61B 17/29 606/205 |
| 2008/0200940 A1 | 8/2008 | Eichmann et al. | |
| 2010/0069940 A1 | 3/2010 | Miller et al. | |
| 2011/0087212 A1 | 4/2011 | Aldridge et al. | |
| 2012/0112687 A1 | 5/2012 | Houser et al. | |
| 2012/0116265 A1 | 5/2012 | Houser et al. | |
| 2012/0116390 A1 | 5/2012 | Madan | |
| 2012/0203213 A1 | 8/2012 | Kimball et al. | |
| 2013/0085419 A1 | 4/2013 | Stoddard et al. | |
| 2013/0096470 A1 | 4/2013 | Strunk et al. | |
| 2014/0005701 A1 | 1/2014 | Olson et al. | |
| 2014/0107684 A1 | 4/2014 | Craig | |
| 2014/0163595 A1 | 6/2014 | Witt et al. | |
| 2015/0148829 A1 | 5/2015 | Kimball et al. | |

OTHER PUBLICATIONS

Chinese Office Action and Search Report dated Jun. 26, 2019 for Application No. CN 201480063722.X, 4 pgs.

International Search Report and Written Opinion dated May 28, 2015 for Application No. PCT/US2014/065630.

Japanese Office Action, Notification of Reasons for Refusal, and Search Report dated Aug. 7, 2018 for Application No. JP 2016-533140, 21 pgs.

U.S. Appl. No. 61/410,603, filed Nov. 5, 2010.

U.S. Appl. No. 61/734,636, filed Dec. 7, 2012.

U.S. Design Pat. No. D776,276.

Brazilian Examination Report dated Mar. 11, 2020 for Application No. BRI 12016011466-3, 4 pgs.

European Examination Report dated Apr. 19, 2021 for Application No. EP 14806508.9, 7 pgs.

Indian Examination Report dated Feb. 24, 2020 for Application No. IN 201617021062, 6 Pgs-.

* cited by examiner

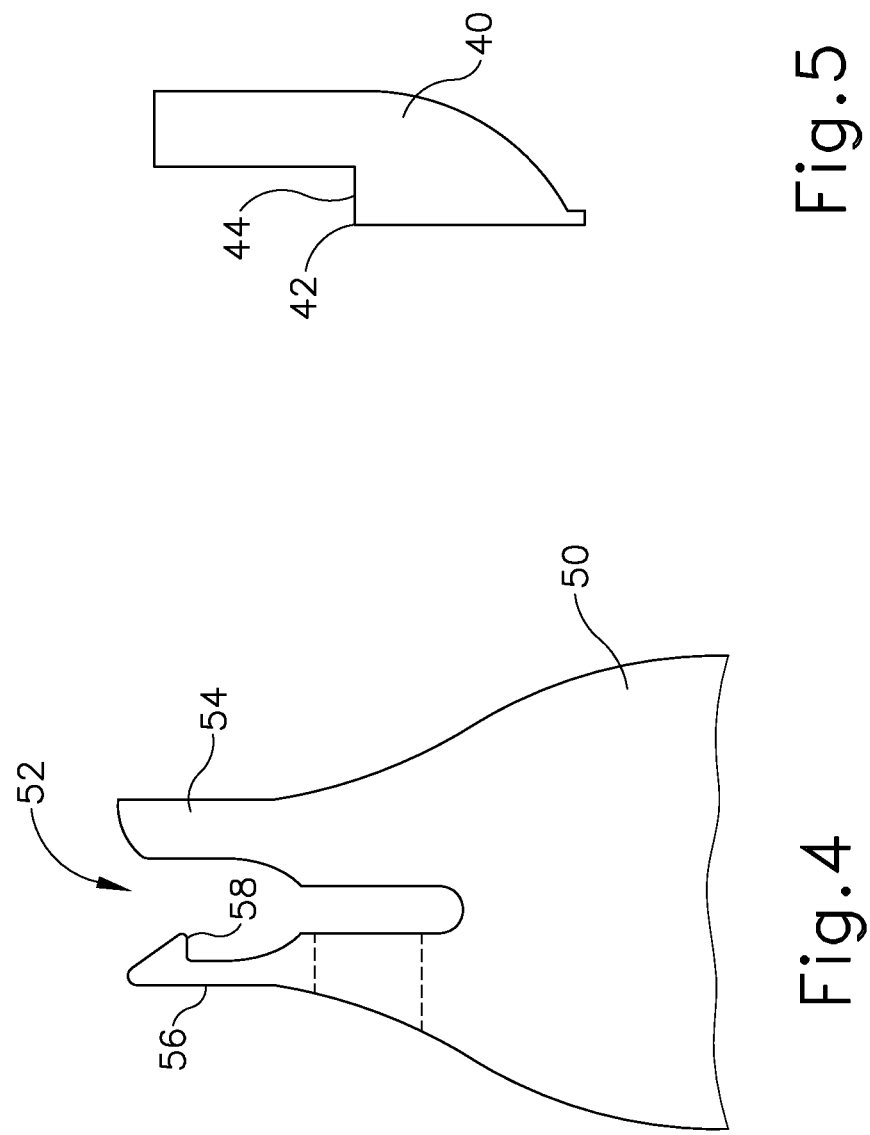

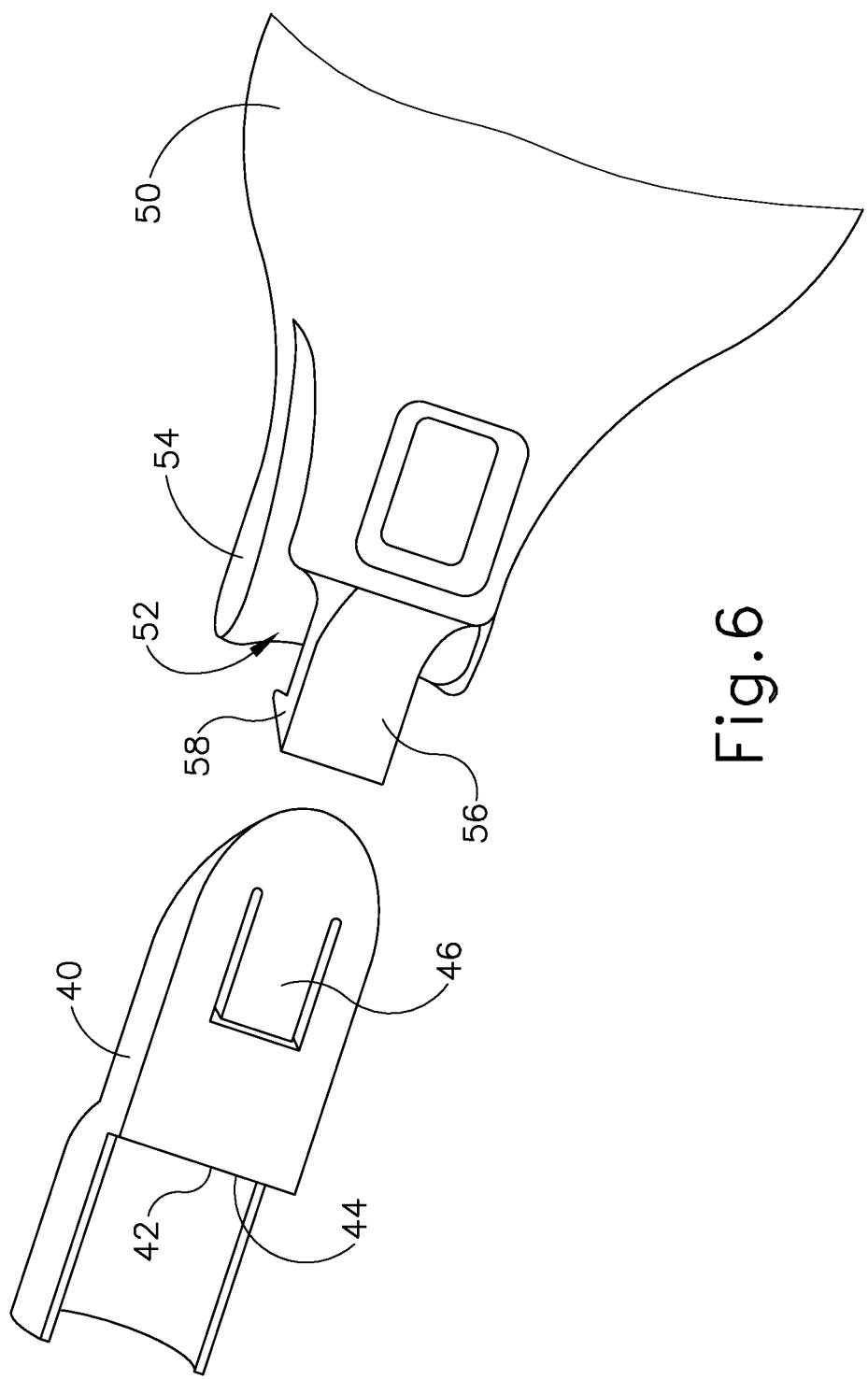

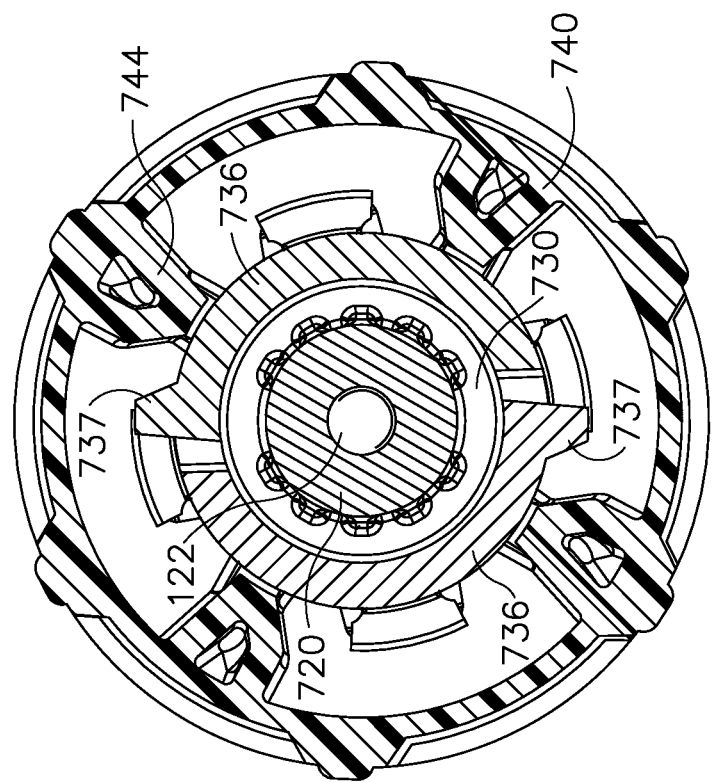

METHODS AND FEATURES FOR COUPLING ULTRASONIC SURGICAL INSTRUMENT COMPONENTS TOGETHER

This application is a continuation of U.S. patent application Ser. No. 14/087,352, filed Nov. 22, 2013, entitled "Methods and Features for Coupling Ultrasonic Surgical Instrument Components Together," issued as U.S. Pat. No. 10,226,271 on Mar. 12, 2019.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, now U.S. Pat. No. 8,623,027, issued Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," now U.S. Pat. No. 9,393,037, issued Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical Instruments," now U.S. Pat. No. 9,095,367, issued Aug. 4, 2015 the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4 depicts a side elevational view of a distal end of the torque wrench of the instrument of FIG. 1;

FIG. 5 depicts a side elevational view of the blade cap of the instrument of FIG. 1;

FIG. 6 depicts a perspective view of the distal end of the torque wrench of FIG. 4 positioned to engage the cap of FIG. 5;

FIG. 37 depicts a cross-sectional end view of the instrument of FIG. 32, taken along line 37-37 of FIG. 36.

Figure 1:
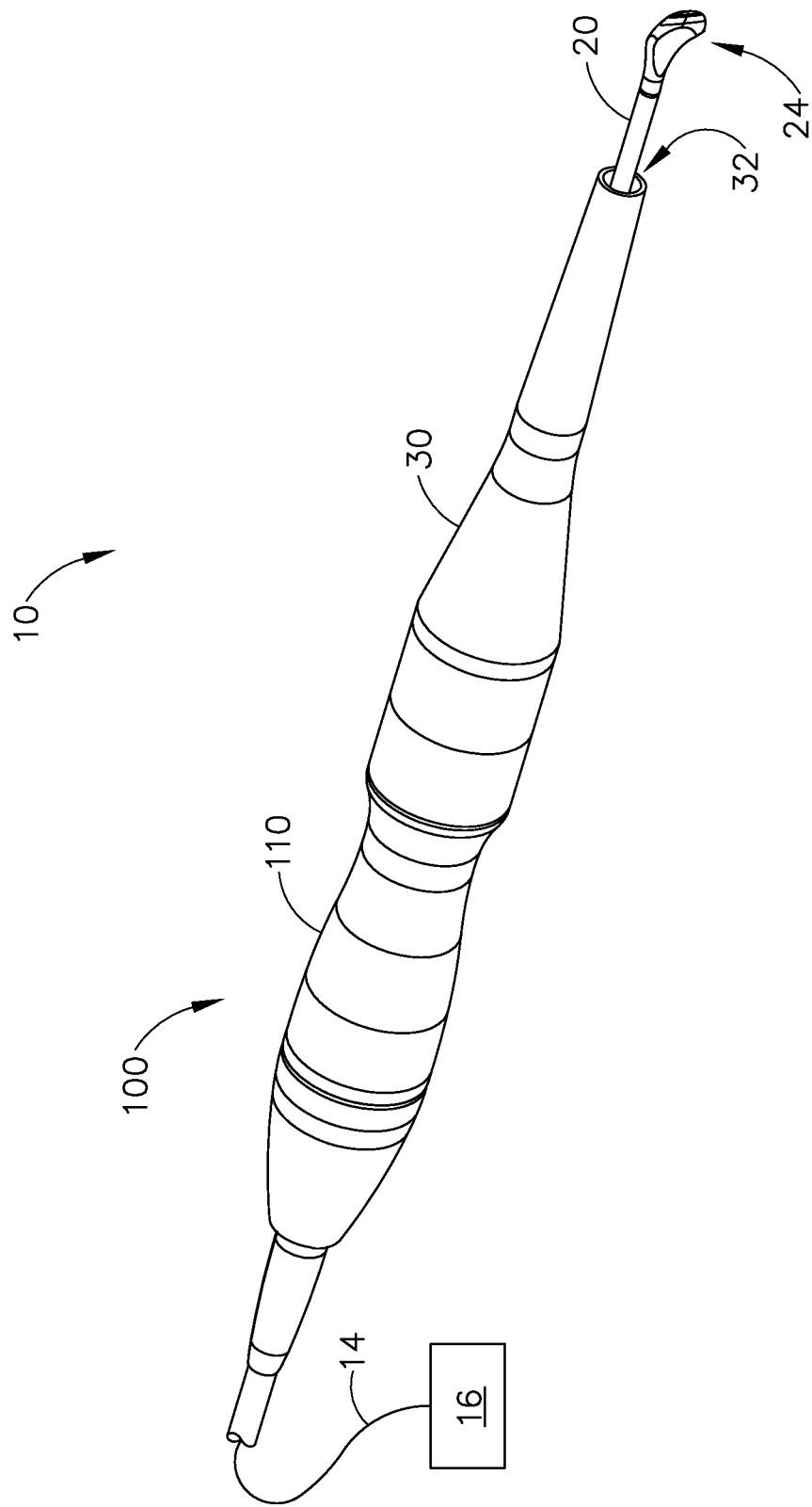
FIG. 1 depicts a perspective view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIGS. 1-6 illustrate an exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, now U.S. Pat. No. 8,623,027; U.S. Pub. No. 2010/0069940 now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265 now abandoned; U.S. patent application Ser. No. 13/538,588, now U.S. Pat. No. 9,393,037; U.S. patent application Ser. No. 13/657,553, now U.S. Pat. No. 9,095,367; U.S. Pat. App. No. 61/410,603; and/or U.S. patent application Ser. No. 14/028,717, now U.S. Pat. No. 10,172,636, issued Jan. 8, 2019. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a transducer assembly (100), an acoustic waveguide (20), and a shroud (30). A proximal end of waveguide (20) includes a threaded bore (22). A distal end of waveguide (20) includes an ultrasonic blade (24). Ultrasonic blade (24) of the present example has a scoop-like shape. It should be understood that ultrasonic blade (24) may comprise a curved blade (e.g. Ethicon Endo-Surgery, Inc. Product Code SNGCB), a hook blade (e.g. Ethicon Endo-Surgery, Inc. Product Code SNGHK), a combination hook blade (e.g. Ethicon Endo-Surgery, Inc. Product Code SNGHK2). As yet another merely illustrative example, blade (24) may be constructed in accordance with at least some of the teachings of U.S. Provisional Patent App. No. 61/734,636, entitled "Ultrasonic Surgical Blade," filed Dec. 7, 2012, the disclosure of which is incorporated by reference herein; and/or U.S. Pat. No. 8,057,498, entitled "Ultrasonic Surgical Instrument Blades," issued Nov. 15, 2011, the disclosure of which is incorporated by reference herein. Other suitable configurations that may be used for blade (24) will be apparent to those of ordinary skill in the art in view of the teachings herein.

As will be discussed in more detail below, waveguide (20) is configured to transfer ultrasonic vibrations from transducer assembly (100) to ultrasonic blade (24) to thereby sever and/or seal tissue. A proximal end of shroud (30) threadably couples with a distal end of transducer assembly (100). Shroud (30) defines an interior bore (32) that passes completely through shroud (30) from the proximal end to a distal end thus defining a proximal opening and a distal opening. Waveguide (20) is disposed within interior bore (32) of shroud (30) such that waveguide (20) may be threadably coupled with transducer assembly (100) via the proximal opening of shroud (30). A distal portion of waveguide (20), including ultrasonic blade (24), projects distally from a distal end of shroud (30) via the distal opening of shroud (30).

Figure 2A:
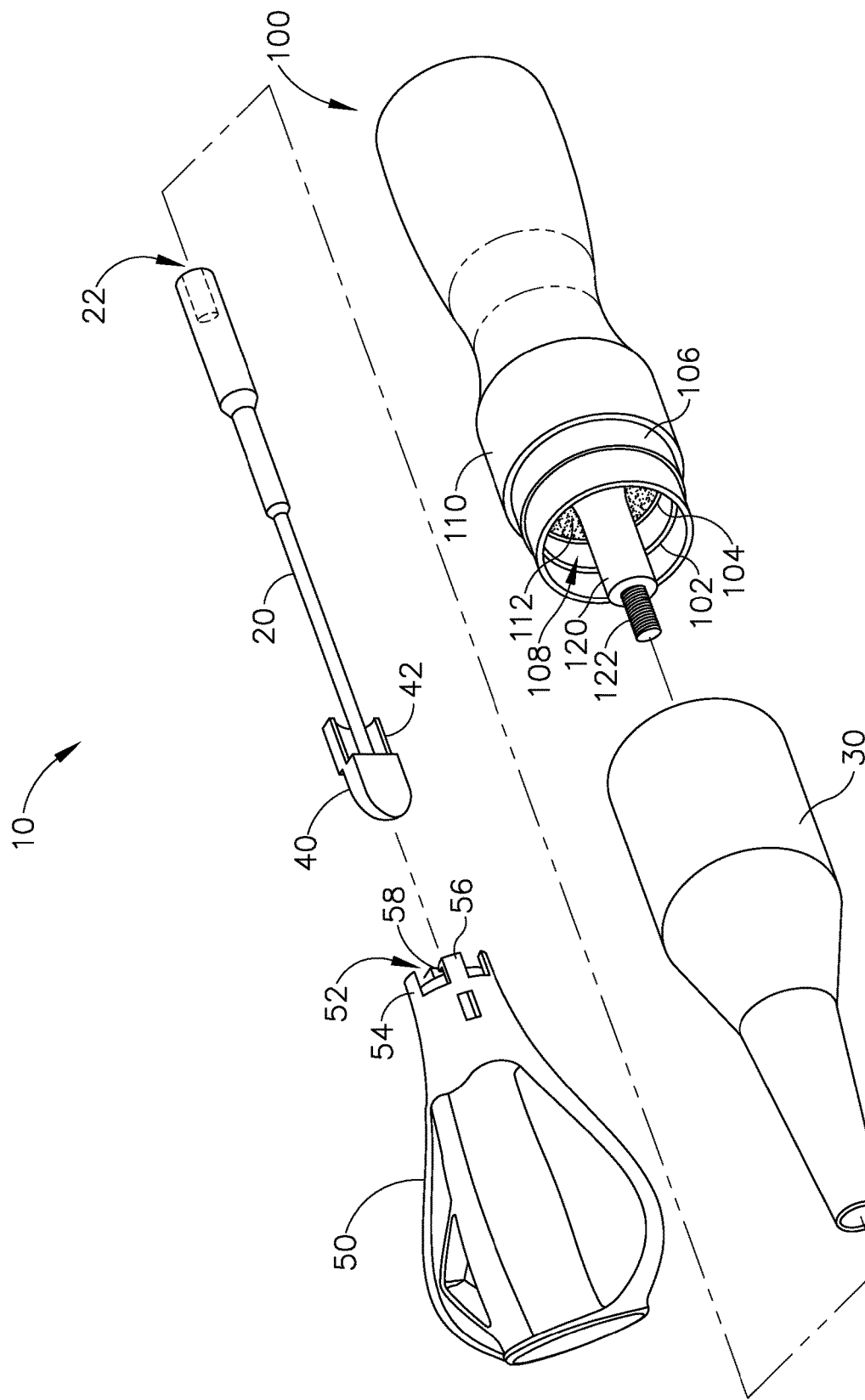
FIG. 2A depicts an exploded perspective view of the instrument of FIG. 1, showing the instrument in a disassembled state.

Transducer assembly (100) of the present example is coupled to a generator (16) via a cable (14), though it should be understood that transducer assembly (100) may instead be a cordless transducer. As best seen in FIG. 2A, transducer assembly (100) comprises a housing (110), a first conductive ring (102), a second conductive ring (104), and a horn (120). As will be discussed in more detail below, horn (120) comprises a threaded stud (122) extending distally therefrom such that horn (120) is configured to couple with a threaded bore (22) formed in a proximal end of waveguide (20). In some versions, first conductive ring (102) comprises a ring member that is disposed between housing (110) and horn (120). First conductive ring (102) is formed within a cavity (108) of transducer assembly (100) such that first conductive ring (102) is electrically isolated from second conductive ring (104) and other conductive components of transducer assembly (100). First conductive ring (102) is located on a non-conductive platform extending distally from housing (110). First conductive ring (102) is electrically coupled to cable (14), shown in FIG. 1, by one or more electrical wires or conductive etchings (not shown) within housing (110).

Second conductive ring (104) of transducer assembly (100) similarly comprises a ring member that is disposed between housing (110) and horn (120). In particular, second conductive ring (104) is disposed between first conductive ring (102) and horn (120). As is shown in FIG. 2A, first and second conductive rings (102, 104) are concentric members that are longitudinally offset from each other, with conductive ring (102) also being positioned at a greater radial distance from the central axis shared by conductive rings (102, 104). Second conductive ring (104) is likewise electrically isolated from first conductive ring (102) and other conductive components of transducer assembly (100). Similar to first conductive ring (102), second conductive ring (104) extends distally from a non-conductive platform. A washer-shaped spacer (112) is interposed between second conductive ring (102) and horn (120) in this example. It should be understood that one or more additional washer-shaped spacers (112) may be disposed between first and second conductive rings (102, 104) or between the rings (102, 104) and other components of transducer assembly (100). Second conductive ring (104) is also electrically coupled to cable (14), shown in FIG. 1, by one or more electrical wires or conductive etchings (not shown) within housing (110). By way of example only, transducer assembly (100) may be constructed and operable in accordance with a Model No. HP054 transducer assembly by Ethicon Endo-Surgery, Inc. of Cincinnati, Ohio.

As previously discussed, the distal end of transducer assembly (10) threadably couples with threaded bore (22) formed in the proximal end of waveguide (20) via threaded stud (122) of horn (120). The distal end of transducer assembly (100) also interfaces with one or more electrical connections (not shown) via first and second conductive rings (102, 104) to electrically couple transducer assembly (100) to buttons (not shown) of instrument (10) to provide a user with finger-activated controls for activating transducer assembly (100) while using surgical instrument (10). An operator may activate the buttons to selectively activate transducer assembly (100) to activate ultrasonic blade (24). Instrument (10) may comprise a pair of buttons—one for activating ultrasonic blade (24) at a low power and another for activating ultrasonic blade (24) at a high power. Of course, any other suitable number of buttons and/or otherwise selectable power levels may be provided. The buttons may be positioned such that an operator may readily fully operate instrument (10) with a single hand. Furthermore, hand activated buttons may be supplemented by or substituted with a foot pedal assembly that may be used to selectively activate transducer assembly (100). Still other suitable configurations for transducer assembly (100), and features that may be used to selectively activate transducer assembly (100), will be apparent to one of ordinary skill in the art in view of the teachings herein. For instance, first and second conductive rings (102, 104) may be omitted from the distal end of transducer assembly (100) and the electrical coupling of transducer assembly (100) to the buttons may be accomplished by alternative features, such as conductors at the proximal end of transducer assembly (100), conductors located along the side of housing (110) of transducer assembly (100), directly from cable (14), and/or any other structures and configurations as will be apparent to one of ordinary skill in the art in view of the teachings herein.

Transducer assembly (100) includes a piezoelectric stack (not shown) within housing (110). When transducer assembly (100) of the present example is activated, an electric field is created in the piezoelectric stack, causing the piezoelectric stack and horn (120) to oscillate within and relative to housing (110). A mounting flange (not shown) is used to couple horn (120) to housing (110), to thereby structurally support the piezoelectric stack in housing (110). The mounting flange may be located at a node associated with resonant ultrasonic vibrations communicated from the piezoelectric stack to horn (120). Transducer assembly (100) is operable to create mechanical energy, or vibrations, at an ultrasonic frequency (such as 55.5 kHz). If transducer assembly (100) is coupled to waveguide (20) via horn (120), then these mechanical oscillations are transmitted through waveguide (20) to ultrasonic blade (24). In the present example, ultrasonic blade (24), being coupled to waveguide (20), oscillates at the ultrasonic frequency. Thus, when ultrasonic blade (24) contacts tissue, the ultrasonic oscillation of ultrasonic blade (24) may sever and/or seal the tissue. An electrical current may also be provided through ultrasonic blade (24) to cauterize the tissue. For instance, monopolar or bipolar RF energy may be provided through ultrasonic blade (24). While some configurations for transducer assembly (100) have been described, still other suitable configurations for transducer assembly (100) will be apparent to one of ordinary skill in the art in view of the teachings herein.

As previously discussed, transducer assembly (100) is coupled with a generator (16) via a cable (14). Transducer assembly (100) receives electrical power from generator (16) and converts that power into ultrasonic vibrations through piezoelectric principles. Generator (16) may include a power source and control module that is configured to provide a power profile to transducer assembly (100) that is particularly suited for the generation of ultrasonic vibrations through transducer assembly (100). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (16) may be integrated into instrument (100), and that instrument (10) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Ultrasonic vibrations that are generated by transducer assembly (100) are communicated along an acoustic waveguide (20), which extends through shroud (30) to reach ultrasonic blade (24). As noted above, when ultrasonic blade (24) is in an activated state (i.e., vibrating ultrasonically), ultrasonic blade (24) is operable to effectively cut through and seal tissue. It should be understood that waveguide (20) may be configured to amplify mechanical vibrations transmitted through waveguide (20). Furthermore, waveguide (20) may include features operable to control the gain of the longitudinal vibrations along waveguide (20) and/or features to tune waveguide (20) to the resonant frequency of the system.

In the present example, the distal end of ultrasonic blade (24) is located at a position corresponding to an anti-node associated with resonant ultrasonic vibrations communicated through waveguide (20), in order to tune the acoustic assembly to a preferred resonant frequency $f_o$ when the acoustic assembly is not loaded by tissue. When transducer assembly (100) is energized, the distal end of ultrasonic blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (100) of the present example is activated, these mechanical oscillations are transmitted through waveguide (20) to reach ultrasonic blade (24), thereby providing oscillation of ultrasonic blade (24) at the resonant ultrasonic frequency. Thus, when tissue is contacted by ultrasonic blade (24), the ultrasonic oscillation of ultrasonic blade (24) may simultaneously sever the tissue and denature the proteins in adjacent tissue cells, thereby providing a coagulative effect with relatively little thermal spread. In some versions, an electrical current (e.g., in the RF range) may also be provided through ultrasonic blade (24) to further seal the tissue. While some configurations for an acoustic transmission assembly and transducer assembly (100) have been described, still other suitable configurations for an acoustic transmission assembly and transducer assembly (100) will be apparent to one or ordinary skill in the art in view of the teachings herein.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713 now abandoned; U.S. Pub. No. 2007/0282333, now abandoned; U.S. Pub. No. 2008/0200940, now abandoned; U.S. Pub. No. 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265, now abandoned; U.S. patent application Ser. No. 13/538,588, now U.S. Pat. No. 9,393,037; and/or U.S. patent application Ser. No. 13/657,553, now U.S. Pat. No. 9,095,367. Additional merely illustrative variations for instrument (10) will be described in greater detail below. It should be understood that the below described variations may be readily applied to instrument (10) described above and any of the instruments referred to in any of the references that are cited herein, among others.

Figure 2B:
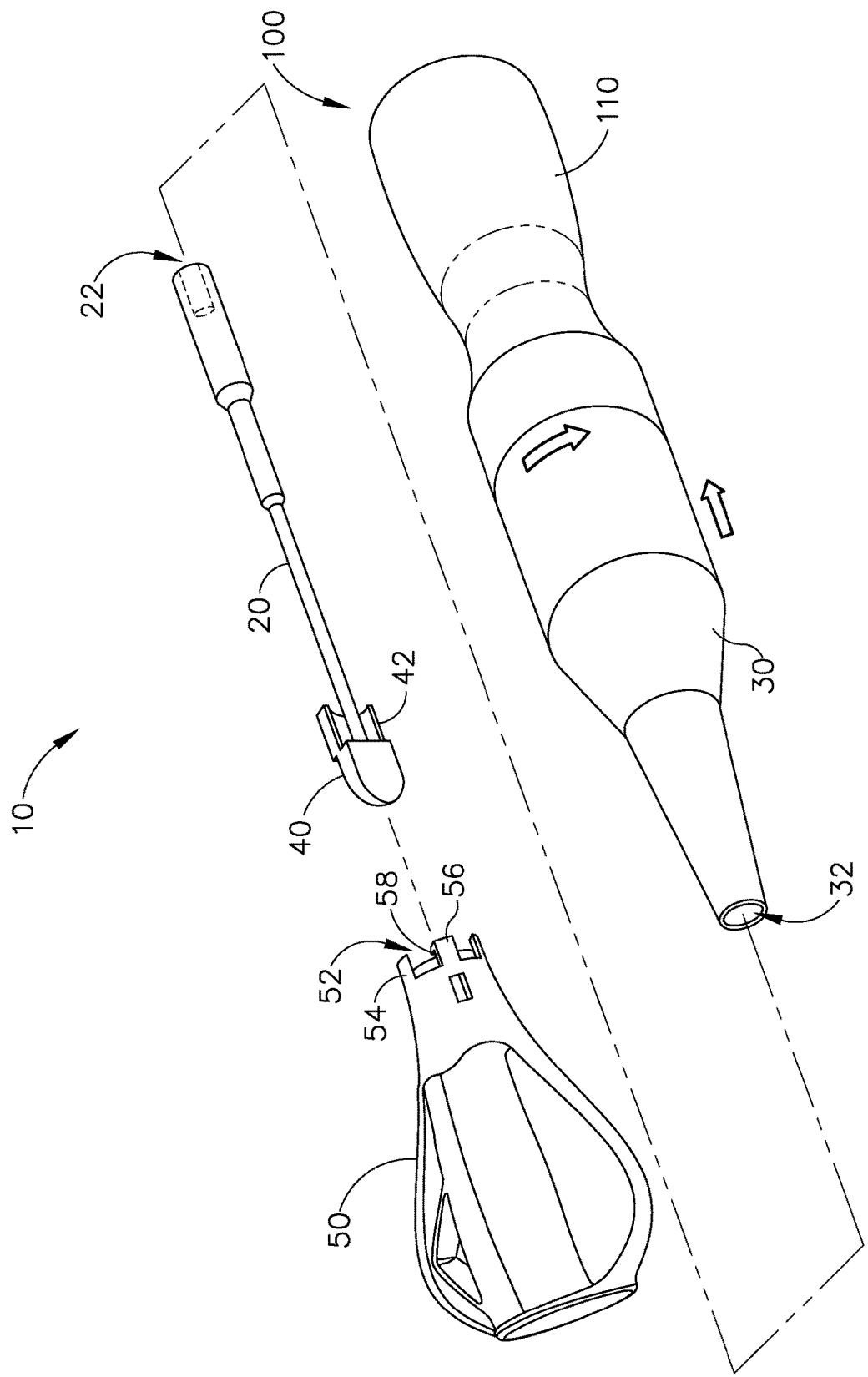
FIG. 2B depicts an exploded perspective view of the instrument of FIG. 1, showing the instrument in a first partially assembled state.

FIGS. 2A-2F show exemplary assembly steps of instrument (10). FIG. 2A shows instrument (10) in a disassembled state, with transducer assembly (100), shroud (30), waveguide (20), and a torque wrench (50) separated from each other. Torque wrench (50) may be configured and operable in accordance with at least some of the teachings of U.S. Pub. No. 2007/0191713, now abandoned, entitled "Ultrasonic Device for Cutting and Coagulating," published Aug. 16, 2007, the disclosure of which is incorporated by reference herein. A cap (40) is positioned about ultrasonic blade (24) such that cap (40) rotates with waveguide (20) as will be described in greater detail below. During a first stage of assembly, a proximal end of shroud (30) is threadably coupled to a sleeve portion (106) of transducer assembly (100) as shown in FIG. 2B. In other words, shroud (30) is maneuvered proximally into engagement with sleeve portion (106); and is then rotated relative to transducer assembly (100) to secure shroud (30) to transducer assembly (100) through a threaded coupling. In some variations, shroud (30) is secured to sleeve portion (106) through complementary bayonet mount features and/or other kinds of coupling features.

Figure 2C:
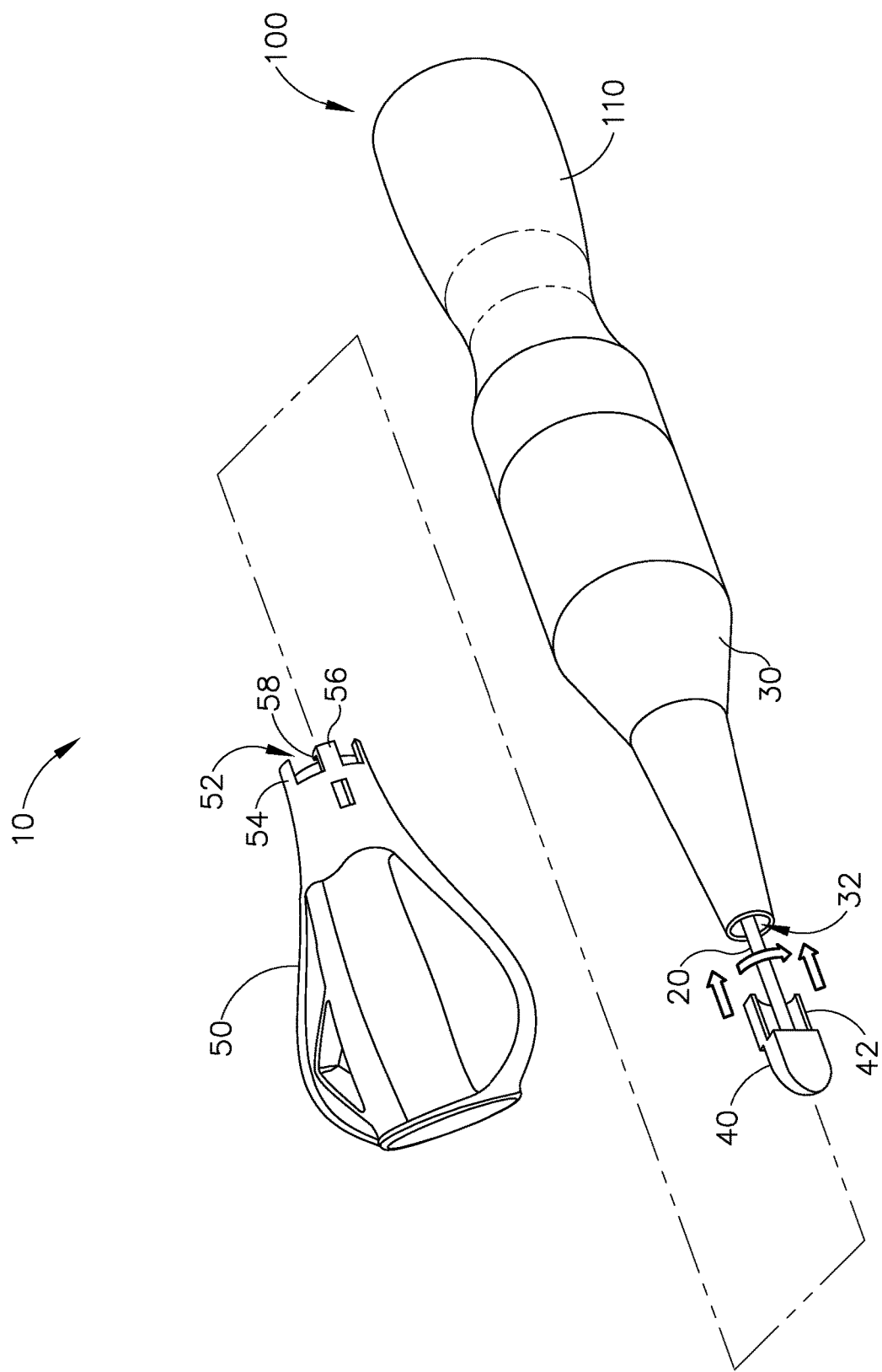
FIG. 2C depicts an exploded perspective view of the instrument of FIG. 1, showing the instrument in a second partially assembled state.

Once shroud (30) has been coupled with transducer assembly (100), waveguide (20) is inserted through the distal opening of shroud (30) and into interior bore (32) as shown in FIG. 2C, such that a user may threadably couple waveguide (20) to threaded stud (122) of transducer assembly (100) via threaded bore (22) formed within the proximal end of waveguide (20). The distal portion of waveguide (20), including ultrasonic blade (24) and cap (40), extends projects from shroud (30) via the distal opening of shroud (30) such that cap (40) is completely exposed. It should be understood that at this point, the user will only have hand tightened waveguide (20) to transducer assembly (100).

Figure 2D:
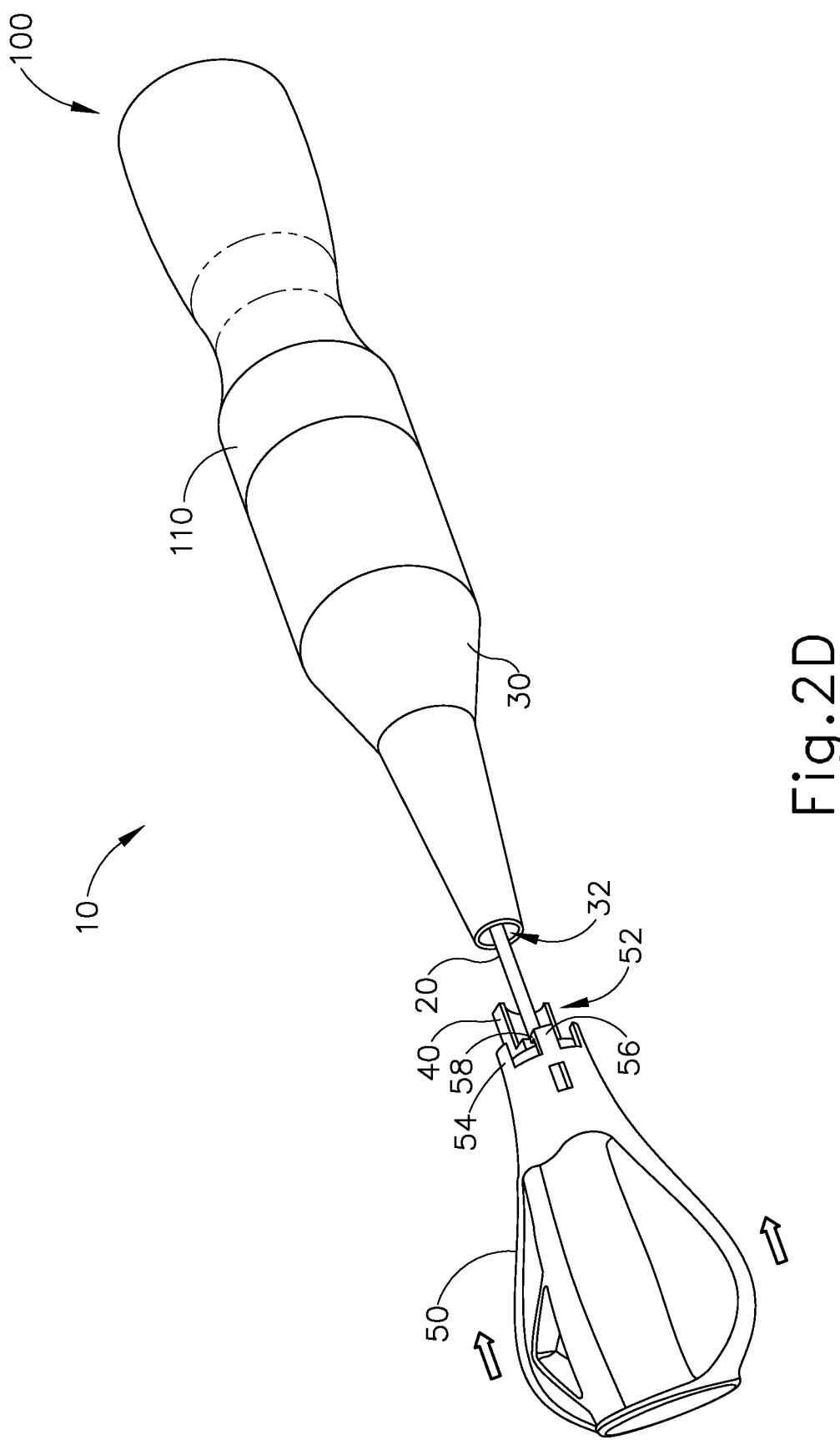
FIG. 2D depicts a perspective view of the instrument of FIG. 1, showing the instrument in a third partially assembled state.
Figure 2E:
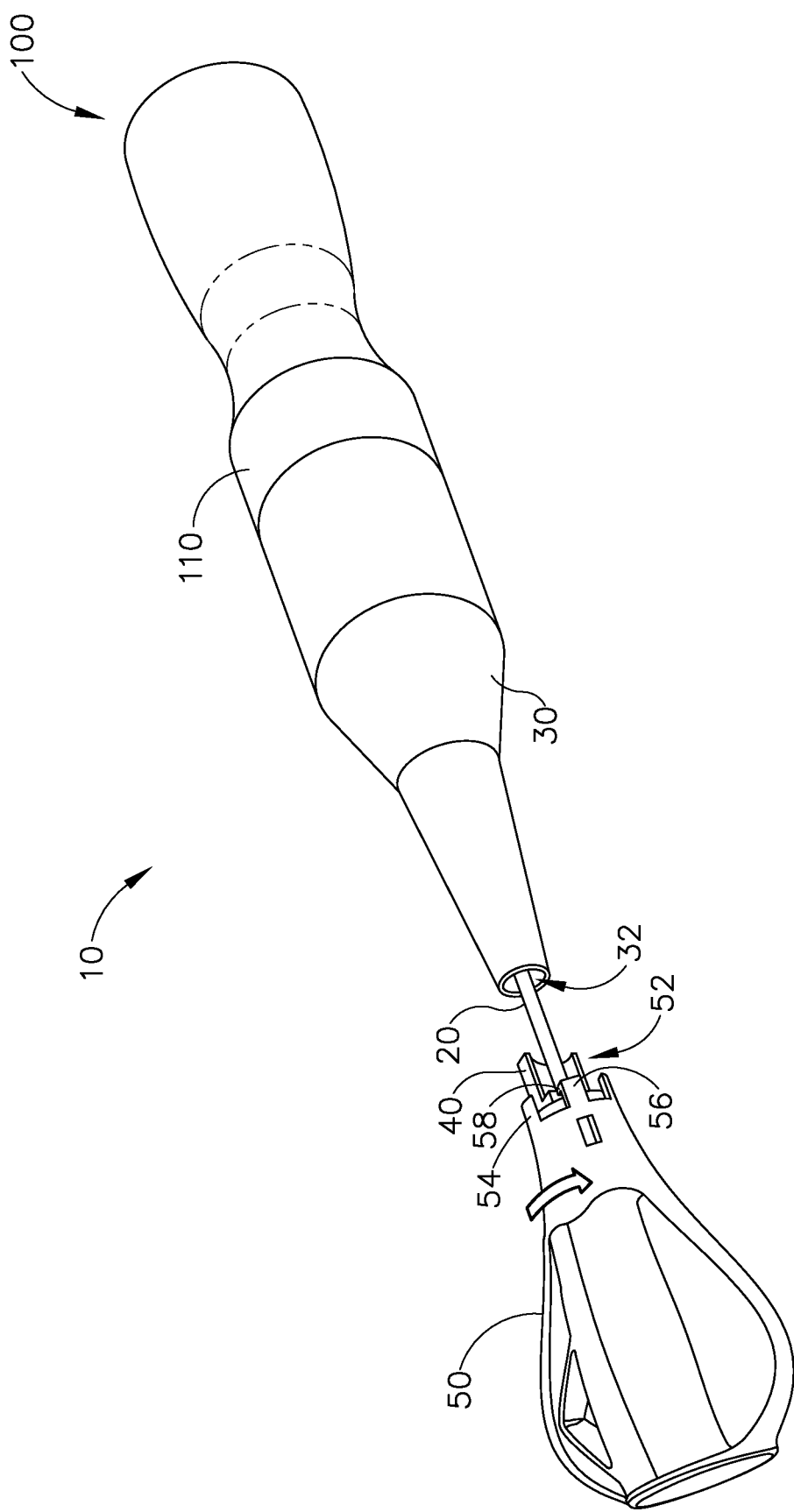
FIG. 2E depicts a perspective view of the instrument of FIG. 1, showing the instrument in a fourth partially assembled state.

Once waveguide (20) has been partially secured to transducer assembly (100) as shown in FIG. 2C, the proximal end of torque wrench (50) is then positioned about cap (40) as shown in FIG. 2D. In the present example, torque wrench (50) couples with cap (40) through a snap fitting such that rotation of torque wrench (50) causes rotation of cap (40) and waveguide (20). As best seen in FIGS. 4-6, the proximal end of torque wrench (50) includes a pocket (52) defined by a rigid base member (54) and a resilient latching member (56). Pocket (52) is configured to receive cap (40). An interior surface of base member (54) complements a bottom exterior surface of cap (40). Latching member (56) includes an inwardly extending tab (58). A proximal surface of tab (58) is angled such that as cap (40) is driven into pocket (52), contact between cap (40) and tab (58) drives latching member (56) outwardly to allow cap (40) to pass into pocket (52). Once cap (40) reaches a predetermined depth within pocket (52), latching member (56) snaps back into place thereby coupling about an edge (42) of cap (40), such torque wrench (50) is coupled with cap (40) through engagement between tab (58) and a shoulder (44) of cap (40). Once torque wrench (50) is coupled with cap (40), torque wrench (50) may be rotated relative to transducer assembly (100) to thereby further tighten waveguide (20) to transducer assembly (100) as shown in FIG. 2E. In some variations, torque wrench (50) is already coupled with cap (40) at the stages shown in FIGS. 2A-2C, such that torque wrench (50) may be used as a grip to facilitate maneuvering of waveguide (20) into initial engagement with threaded stud (122).

As the user rotates waveguide (20) relative to transducer assembly (100) via torque wrench (50) as shown in FIG. 2E, torque wrench (50) is configured to signal the user when waveguide (20) has been coupled with transducer assembly (100) at an appropriate torque value. For instance, torque wrench (50) may be configured to audibly and/or tangibly signal to a user that waveguide (20) has been appropriately connected with transducer assembly (100), such as by emitting audible and/or tangible clicks. In the present example, torque wrench (50) emits two audible clicks once the appropriate torque has been reached between waveguide (20) and transducer assembly (100). In addition to providing audible and/or tactile feedback to the user to indicate suitable coupling of waveguide (20) with transducer assembly (100), torque wrench (50) may also effectively restrict the amount of torque that may be applied through the coupling of waveguide (20) with transducer assembly. For instance, once the appropriate amount of torque has been reached, torque wrench (50) may provide rotational slipping relative to waveguide (20), such that further rotation of torque wrench (50) relative to transducer assembly (100) will not provide further rotation of waveguide (20) relative to transducer assembly (100). Various features that may be used to provide audible/tactile feedback and rotational slipping will be described in greater detail below; while other examples of such features will be apparent to those of ordinary skill in the art in view of the teachings herein.

Figure 2F:
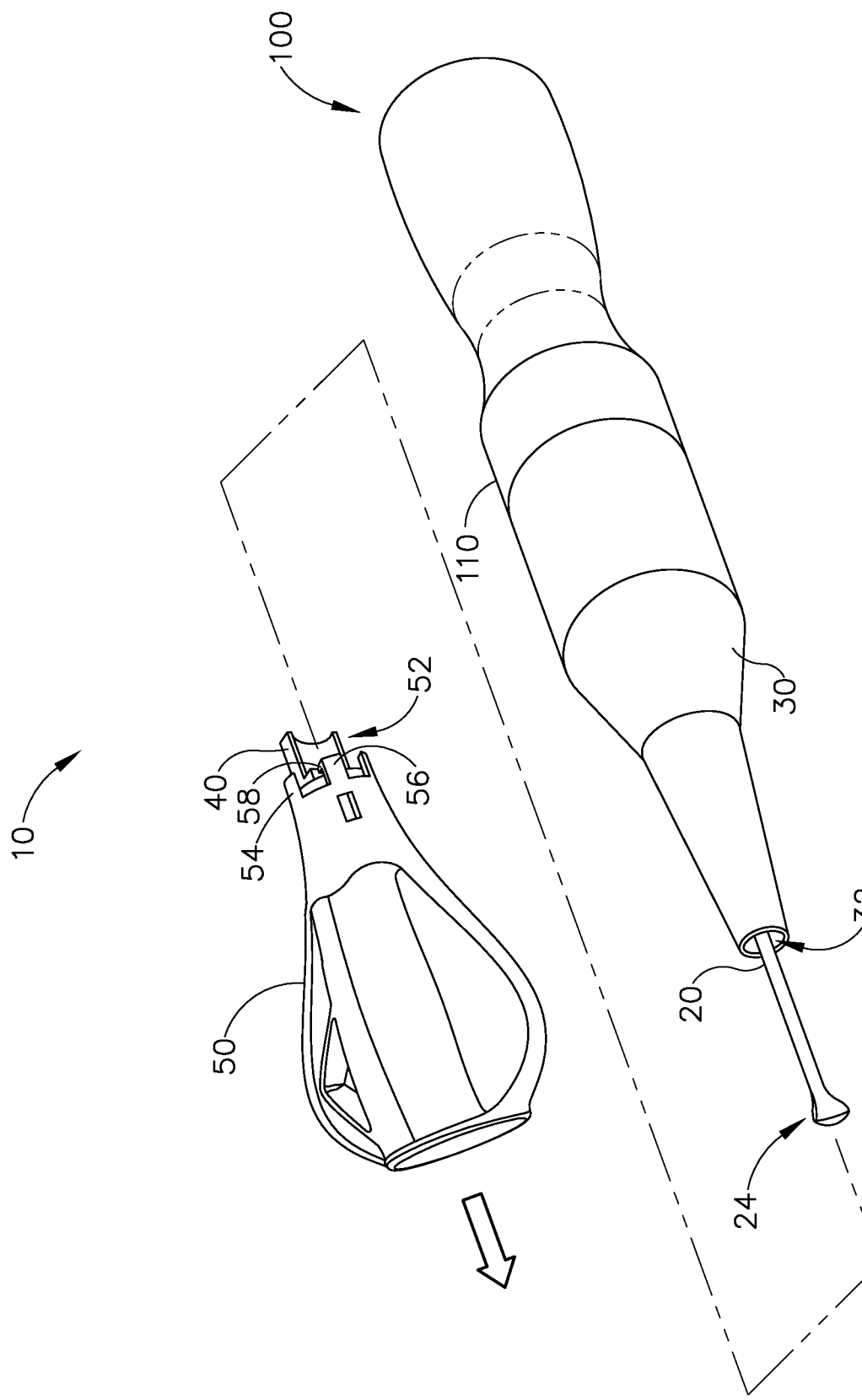
FIG. 2F depicts an exploded perspective view of the instrument of FIG. 1, showing the instrument in a fifth partially assembled state.

As shown in FIG. 2F, torque wrench (50) may be pulled distally away from waveguide (20) after waveguide (20) has been coupled with transducer assembly (100) at the appropriate torque. As also shown in FIG. 2F, cap (40) remains coupled with torque wrench (50) as torque wrench is pulled distally away from waveguide (20). By way of example only, a gripping tab (46) (see FIG. 6) of cap (40) may resiliently bear against blade (24) and thereby provide a friction fit that secures cap (40) to blade (24), such that the user need only overcome the friction between gripping tab (46) and blade (24) in order to remove cap (40) from blade (24). Once torque wrench (50) and cap (40) are pulled away from waveguide (20) and blade (24), instrument (10) may be operated like any other ultrasonic scalpel. Various suitable ways in which instrument (10) may be used once blade (24) has been exposed will be apparent to those of ordinary skill in the art in view of the teachings herein.

Figure 3A:
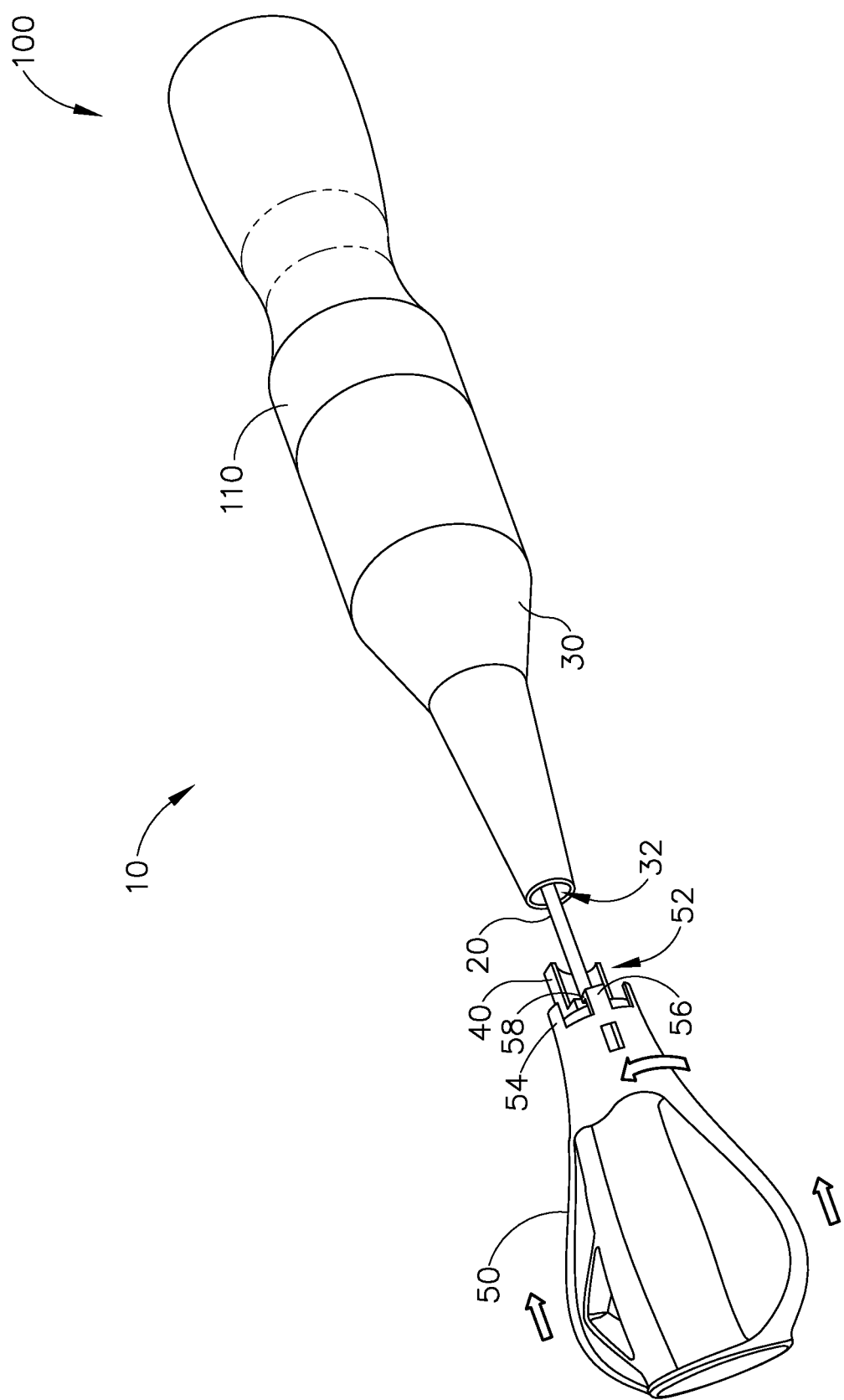
FIG. 3A depicts a perspective view of the instrument of FIG. 1, showing the instrument in a first partially disassembled state.
Figure 3B:
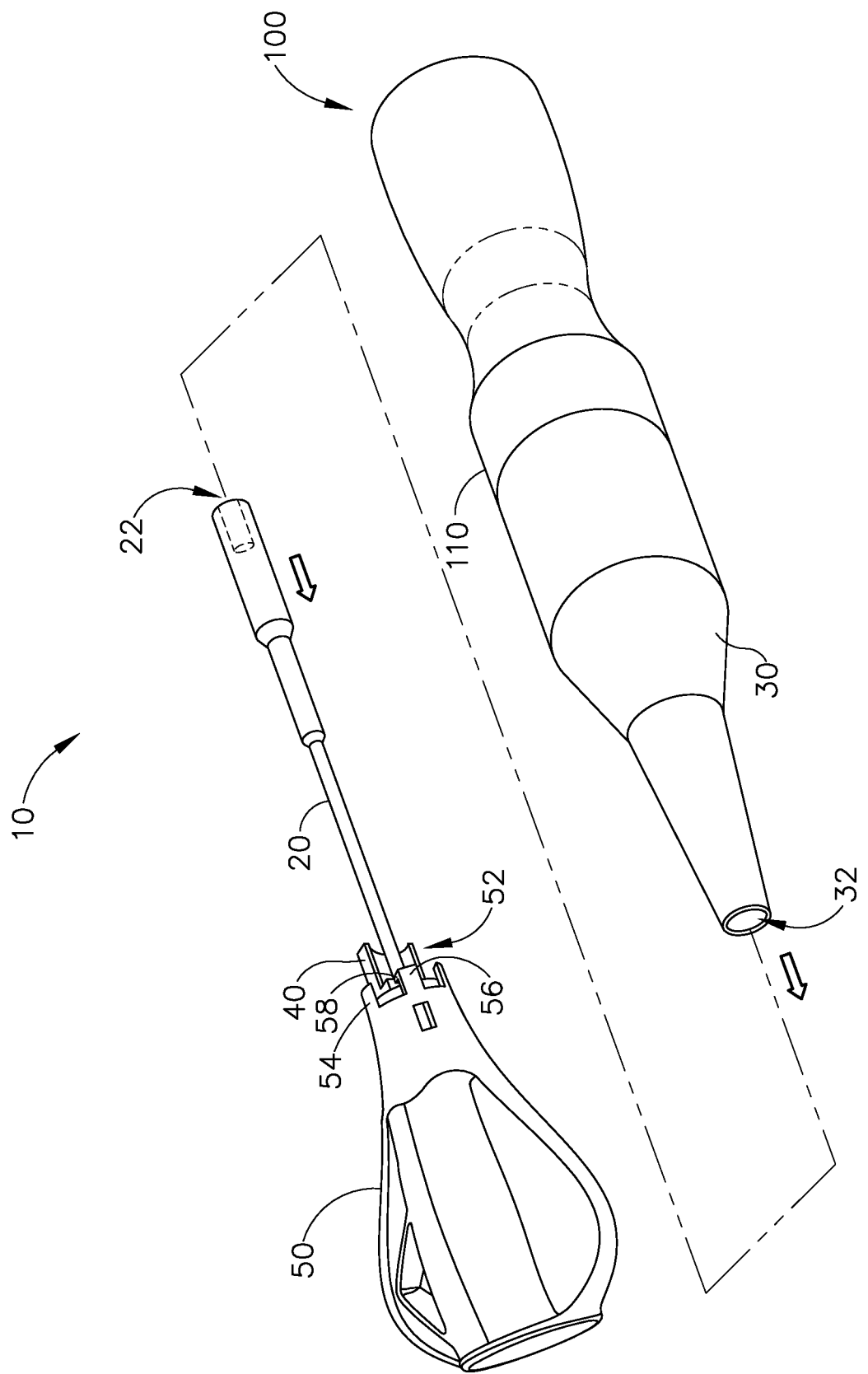
FIG. 3B depicts an exploded perspective view of the instrument of FIG. 1, showing the instrument in a second partially disassembled state.
Figure 3C:
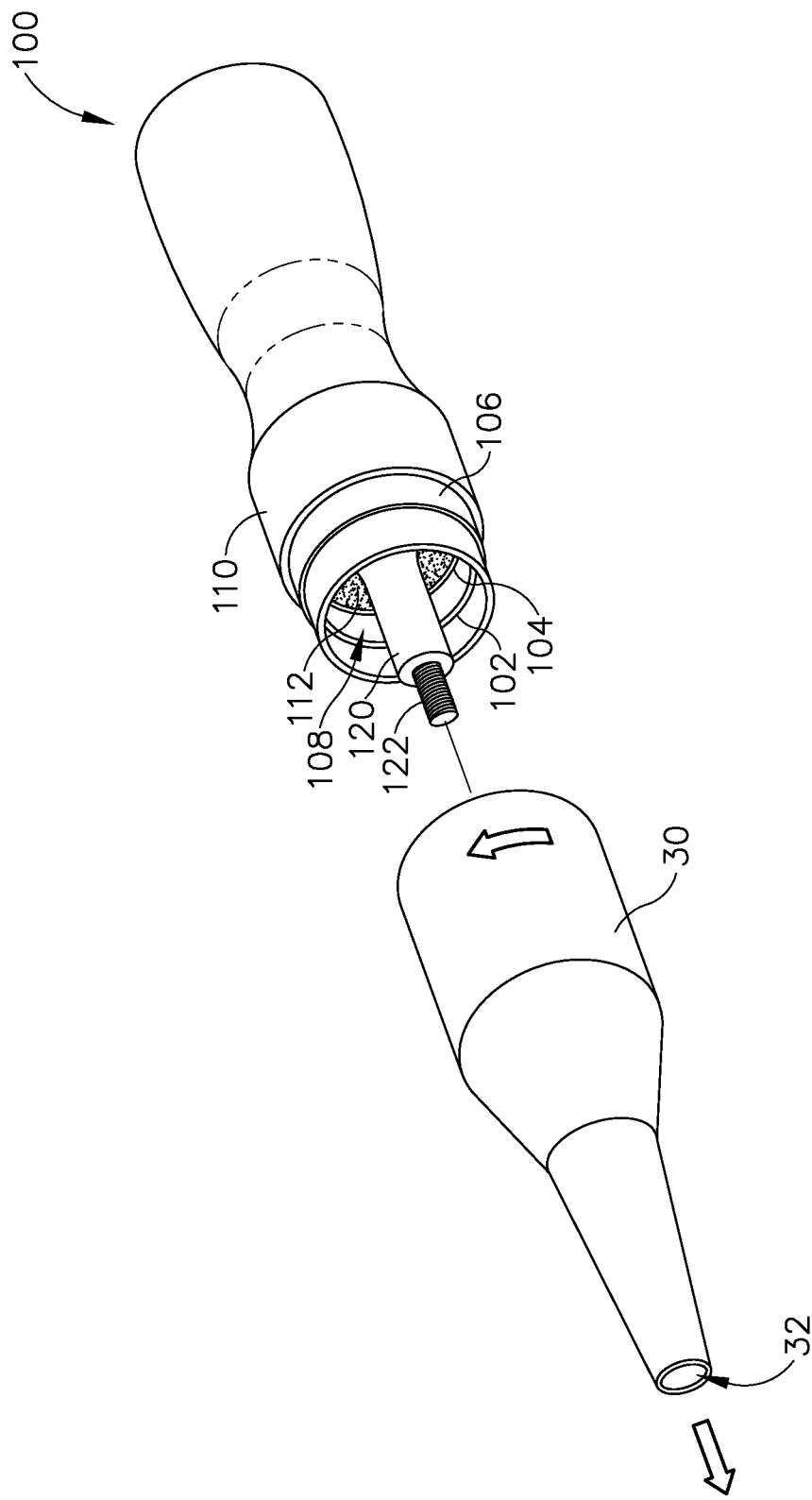
FIG. 3C depicts an exploded perspective view of the instrument of FIG. 1, showing the instrument in a third partially disassembled state.
Figure 7:
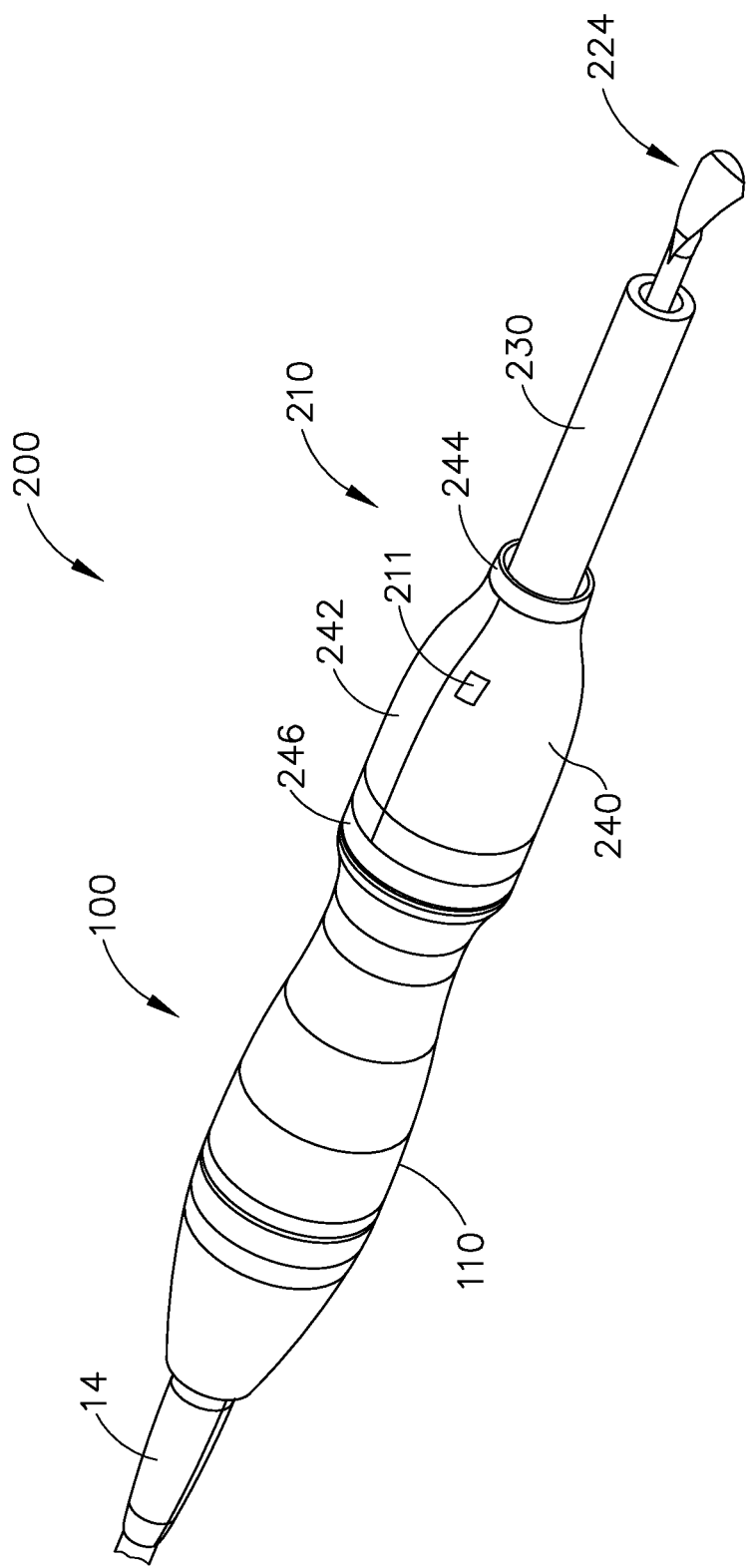
FIG. 7 depicts a perspective view of another exemplary alternative surgical instrument.

FIGS. 3A-3C show exemplary disassembly steps of instrument (10). In the present example, the user has set aside the combination of torque wrench (50) and cap (40) during use of instrument (10) in a surgical procedure, and now returns to using the combination of torque wrench (50) and cap (40) to disassemble instrument (10). In particular, the user grasps torque wrench (50) and maneuvers torque wrench (50) to slide cap (40) proximally back onto blade (24) as shown in FIG. 3A. As also shown in FIG. 3A, the user rotates torque wrench (50) and cap (40) once cap (40) is secured to blade (24), thereby rotating waveguide (20) relative to transducer assembly (100) to disengage threaded stud (122) of transducer assembly (100) form threaded bore (22) of waveguide (20). As shown in FIG. 3B, once waveguide (20) is completely loosened from transducer assembly (100), torque wrench (50), cap (40), and waveguide (20) together may be removed from shroud (30) via the distal opening of shroud (30). As shown in FIG. 3C, shroud (30) may then be decoupled from sleeve portion (106) of transducer assembly (100). At this point, torque wrench (50), cap (40), waveguide (20), and shroud (30) may be disposed of; while transducer assembly (100) may be reconditioned any re-used. Alternatively, the user may wish to handle these components in some other fashion.

II. Exemplary Ultrasonic Surgical Instruments with Integral Torque Assembly

In some versions of instrument (10), it may be desirable to incorporate the torque limiting features of torque wrench (50) within instrument (10), such that a separate component like torque wrench (50) is not needed. In particular, it may be desirable to provide instrument (10) with integral features that indicate to the user when an appropriate amount of torque has been applied to secure waveguide (20) with transducer assembly (100). In addition or in the alternative, it may be desirable to provide instrument (10) with integral features that limit the amount of torque that may be applied to secure waveguide (20) with transducer assembly (100). Several illustrative examples of variations of instrument (10) that include integral torque assemblies will be described in greater detail below. Further examples will be apparent to those of ordinary skill in the art in view of the teachings herein.

A. Exemplary Integral Torque Assembly with Dual Shroud and Retaining Rings

FIGS. 7-12 show an exemplary instrument (200) having an integral torque assembly (250). Instrument (200) of the present example is configured to operate substantially similar to instrument (10) discussed above except for the differences discussed below. In particular, instrument (200) is thus operable to transect and/or seal tissue at a surgical site. Instrument (200) of the present example comprises transducer assembly (100) and a shaft assembly (210). Shaft assembly (210) comprises a waveguide (220), a sheath (230), a pair of shroud halves (240, 242), a pair of retaining rings (244, 246), a torque member (250), and a connector (260). Shaft assembly (210) also includes a user input feature (211) that is operable to selectively activate transducer assembly (100), to thereby selectively activate ultrasonic blade (224) of waveguide (220). User input feature (211) may include one or more switches and/or various other components. By way of example only, user input feature (211) may be constructed and operable in accordance with at least some of the teachings of U.S. Pub. No. 2010/0069940, entitled "Ultrasonic Device for Fingertip Control," published Mar. 18, 2010, now U.S. Pat. No. 9,023,071, the disclosure of which is incorporated by reference herein. As another merely illustrative example, user input feature (211) may be constructed and operable in accordance with at least some of the teachings of U.S. Pub. No. 2012/0203213, entitled "Activation Feature for Surgical Instrument with Pencil Grip," published Aug. 9, 2012, now U.S. Pat. No. 9,107,688, issued Aug. 18, 2015, the disclosure of which is incorporated by reference herein. Still other suitable ways in which user input feature may be constructed and operable will be apparent to those of ordinary skill in the art in view of the teachings herein.

Figure 10:
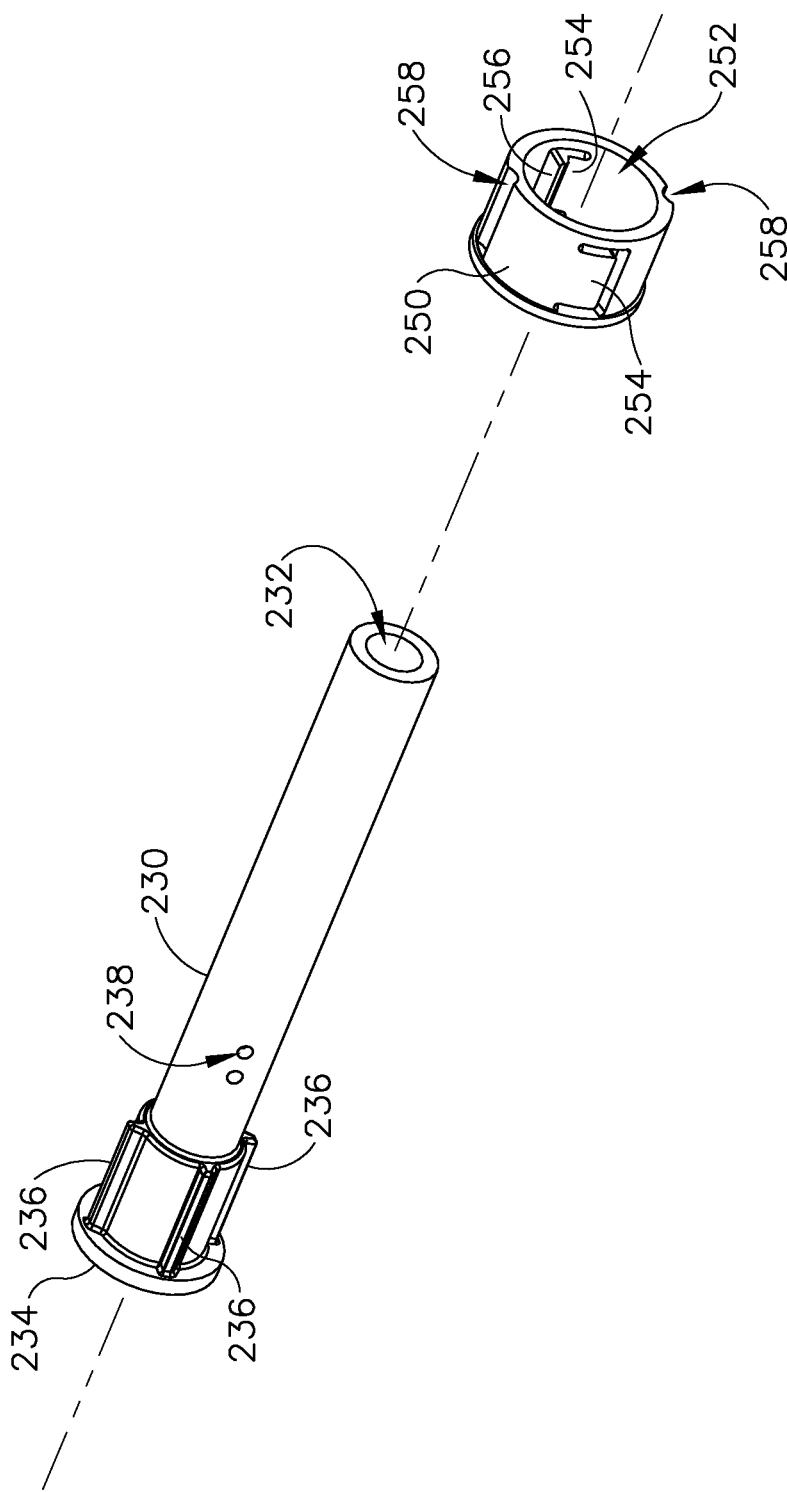
FIG. 10 depicts a detailed perspective view of the sheath and the ratcheting feature of the instrument of FIG. 7.

As shown in FIG. 10, sheath (230) defines a longitudinal interior bore (232) that passes completely through sheath (230) from a proximal end to a distal end, such that bore (232) defines a proximal opening and a distal opening. Bore (232) is configured to receive waveguide (220). A proximal end of sheath (230) includes an annular flange (234) and a plurality of longitudinal projections (236) extending radially outwardly from an exterior surface of sheath (230). Torque member (250) defines a longitudinal interior bore (252) that passes completely through torque member (250) from a proximal end to a distal end, such that bore (252) defines a proximal opening and a distal opening. Interior bore (252) of torque member (250) is configured to receive sheath (230) such that a proximal surface of torque member (250) rests against a distal surface of flange (234). Sheath (230) is rotatably disposed within interior bore (252). Torque member (250) includes a pair of resilient members (254) formed on opposite sides of torque member (250). Each resilient member (254) includes an inwardly extending tab (256). As will be discussed in more detail below, tabs (256) engage projections (236) to transfer rotation of torque member (250) to sheath (230). As will also be discussed in more detail below, a surface (256A) of each tab (256) and a surface (236A) of each longitudinal projection (236) are angled such that as torque member (250) is rotated clockwise about sheath (230), contact between longitudinal projections (236) of sheath and tabs (256) drive resilient members (254) outwardly to allow torque member (250) to be rotated without rotating sheath (230) once waveguide (220) is secured to transducer assembly (100) with an appropriate amount of torque.

Figure 8A:
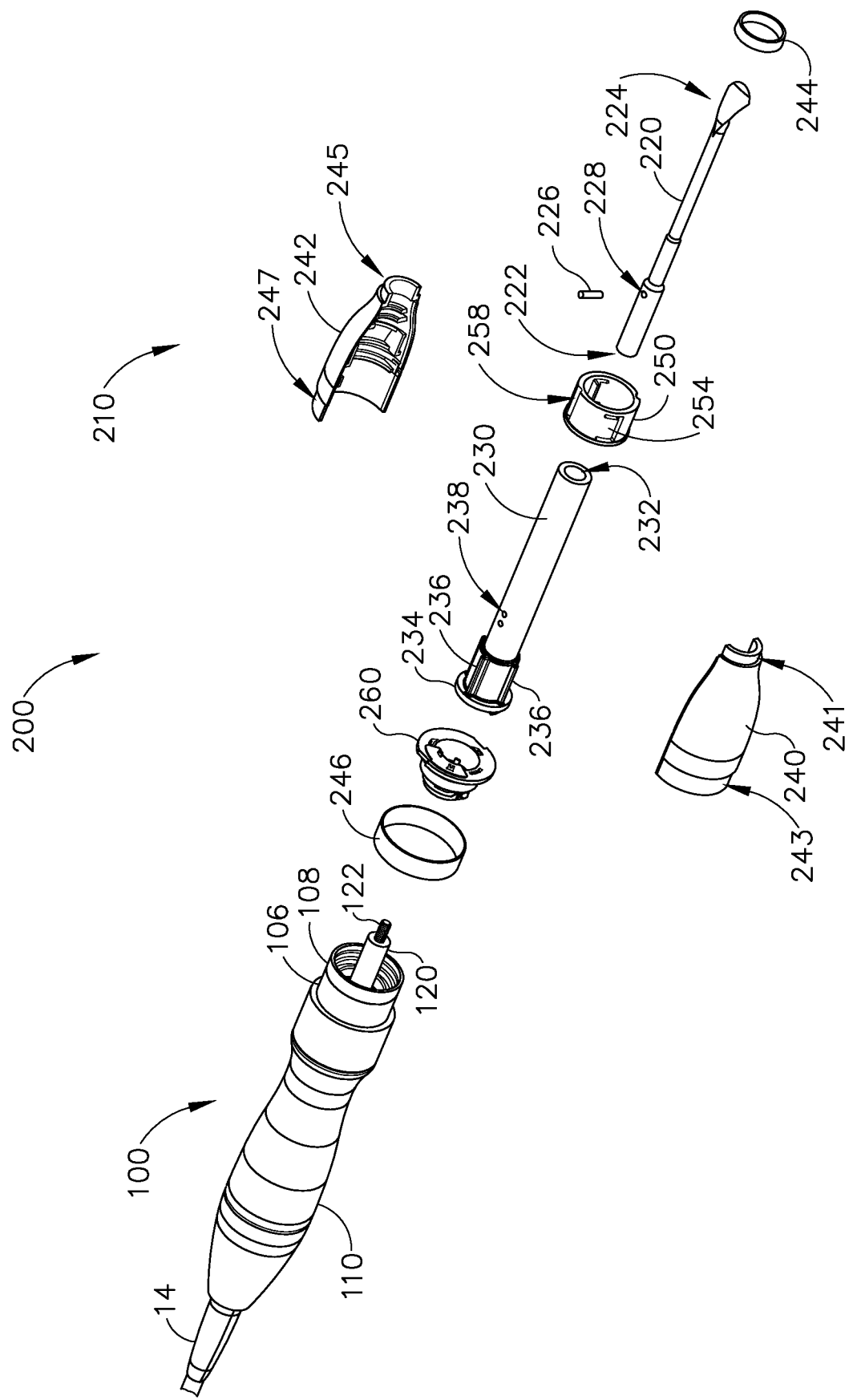
FIG. 8A depicts an exploded perspective view of the instrument of FIG. 7, showing the instrument in a disassembled state.
Figure 8B:
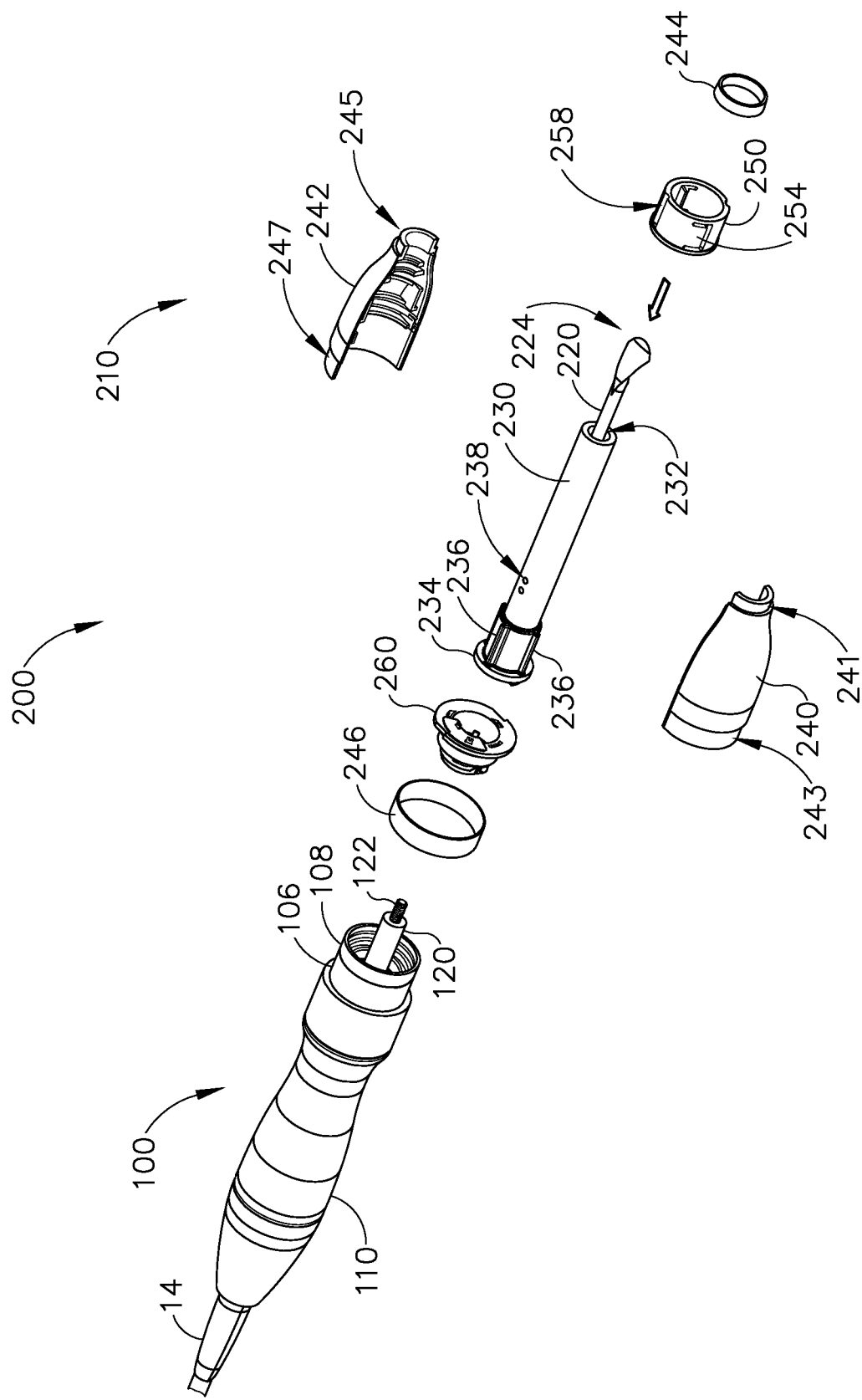
FIG. 8B depicts an exploded perspective view of the instrument of FIG. 7, showing the instrument in a first partially assembled state.

FIGS. 8A-8G show exemplary steps for assembling instrument (200). FIG. 8A shows instrument (200) in a disassembled state, including shaft assembly (210) in a disassembled state. In an initial assembly step, waveguide (220) is inserted into interior bore (232) of sheath (230) such that ultrasonic blade (224) of waveguide (220) extends from the distal end of sheath (230) as shown in FIG. 8B. A pin (226) is passed through aligned openings (238, 228) in sheath (230) and waveguide (220) to thereby couple sheath (230) and waveguide (220), such that rotation of sheath (230) causes concurrent rotation of waveguide (220). It should therefore be understood that sheath (230) and waveguide (220) rotate together unitarily when shaft assembly (210) is fully assembled. Opening (228) is located at a position along the length of waveguide (220) corresponding to a node associated with resonant ultrasonic vibrations communicated through waveguide (220), such that the ultrasonic vibrations are not communicated to pin (226).

Figure 8C:
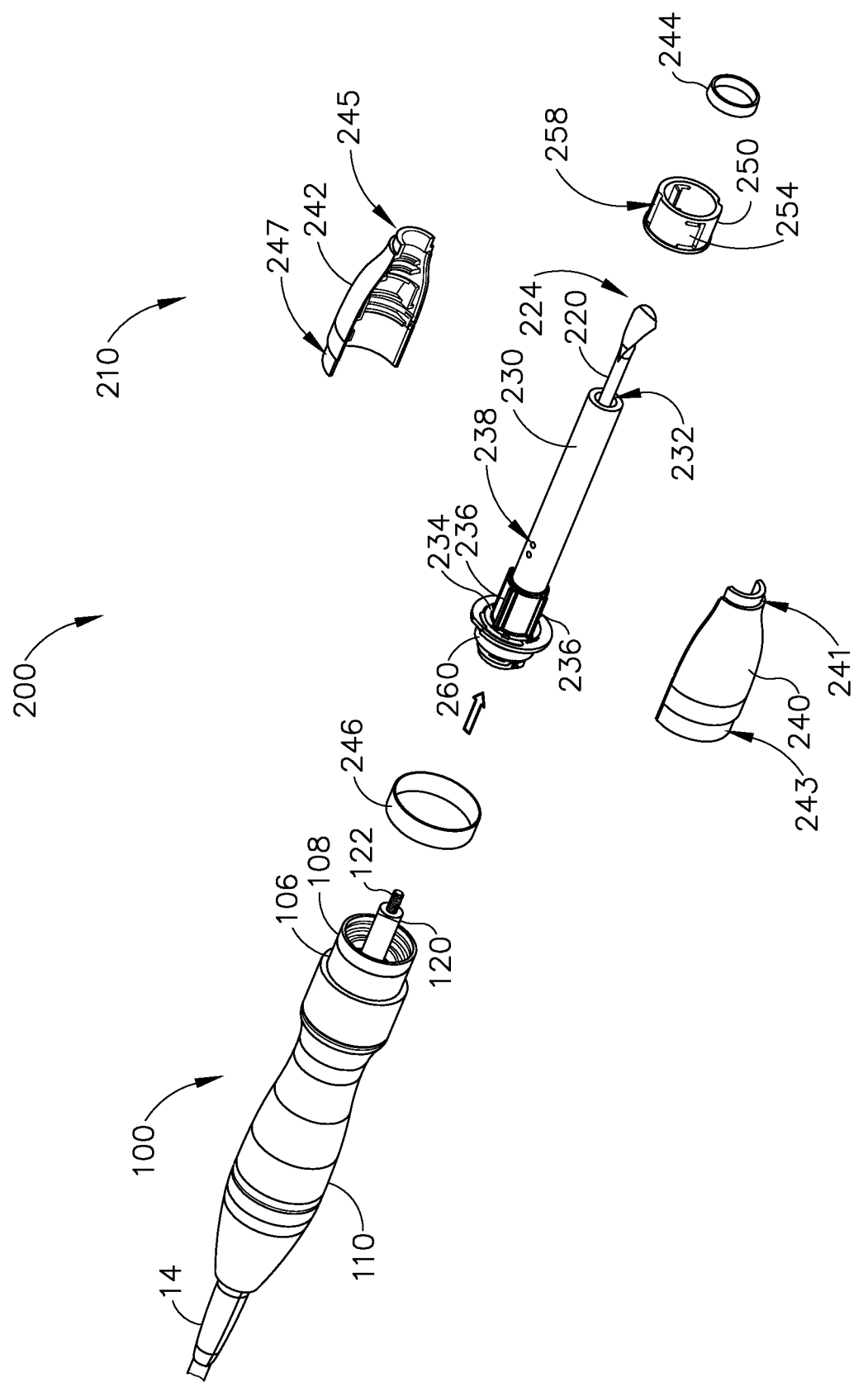
FIG. 8C depicts an exploded perspective view of the instrument of FIG. 7, showing the instrument in a second partially assembled state.
Figure 12:
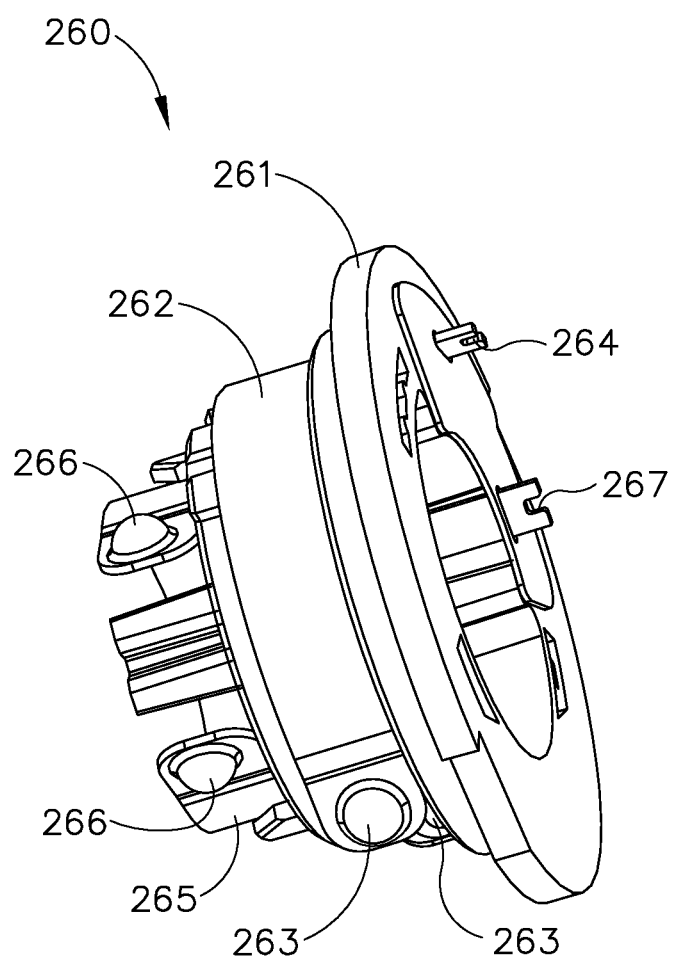
FIG. 12 depicts a perspective view of a connector of the instrument of FIG. 7.
Figure 13:
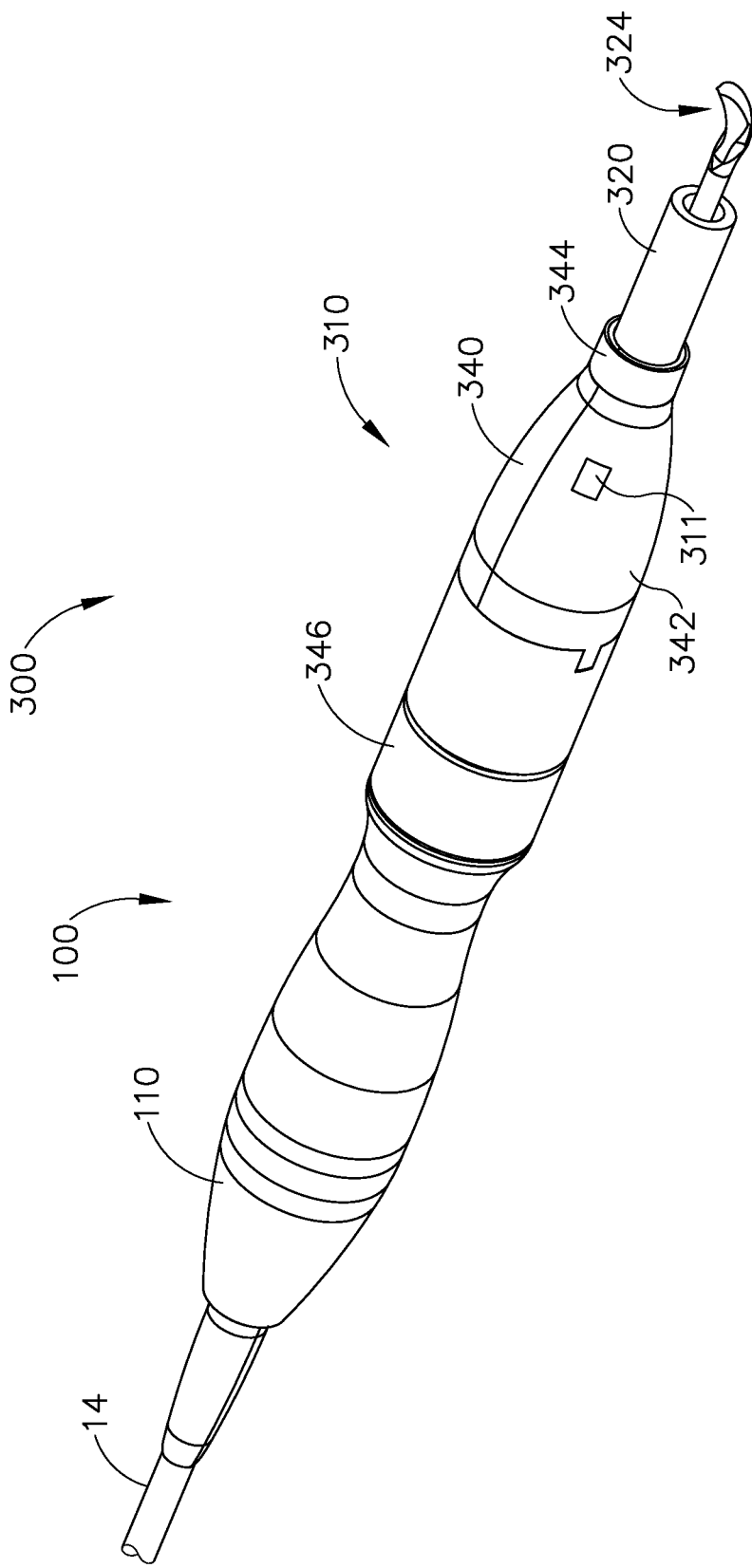
FIG. 13 depicts a perspective view of yet another exemplary alternative surgical instrument that uses the sheath, ratcheting feature, and connector of the instrument of FIG. 7.

With sheath (230) and waveguide (220) coupled together, connector (260) is then coupled to a proximal surface of flange (234) of sheath (230) as shown in FIG. 8C. Connector (260) is configured to insertingly fit in cavity (108) of transducer assembly (100) and thereby guide shaft assembly (210) into aligned engagement with transducer assembly (100). As shown in FIG. 12, connector (260) comprises an annular distal flange (261), a first electrical contact feature (262), and a second electrical contact feature (265). First electrical contact feature (262) includes outwardly extending protrusions (263) that are configured to engage first conductive ring (102) when connector (260) is inserted in cavity (108) of transducer assembly (100). First electrical contact feature (262) also includes a distally projecting feature (264) that is configured to couple with a wire, trace, and/or other conductive feature that is in communication with user input feature (211) of shaft assembly (210). Similarly, second electrical contact feature (265) includes outwardly extending protrusions (266) that are configured to engage second conductive ring (104) when connector (260) is inserted in cavity (108) of transducer assembly (100). Second electrical contact feature (265) also includes a distally projecting feature (267) that is configured to couple with a wire, trace, and/or other conductive feature that is in communication with user input feature (211) of shaft assembly (210). Electrical contact features (262, 265) thus provide electrical coupling between user input feature (211) and transducer assembly (100).

Figure 8D:
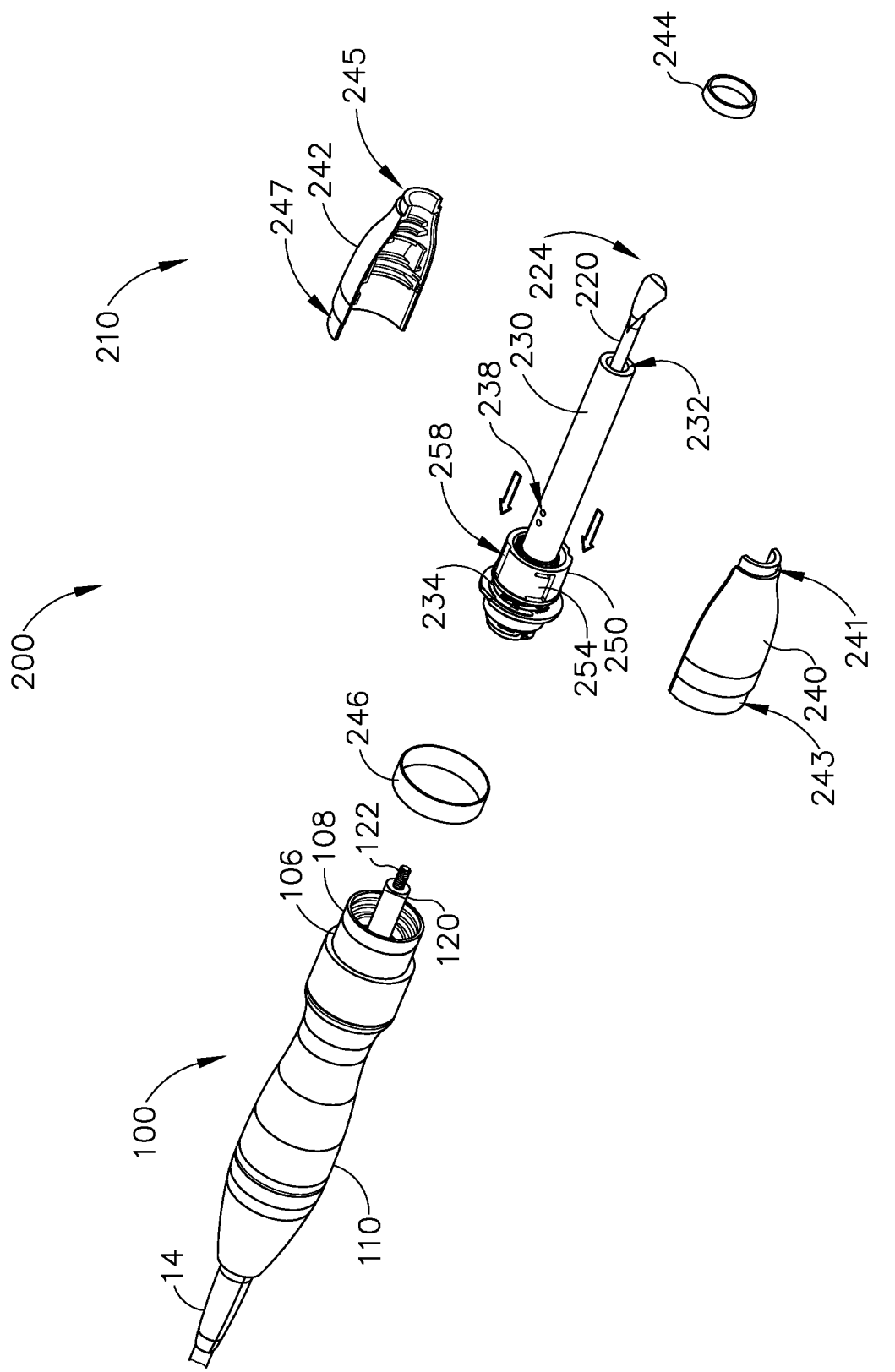
FIG. 8D depicts an exploded perspective view of the instrument of FIG. 7, showing the instrument in a third partially assembled state.

As shown in FIG. 8D, torque member (250) is then positioned about sheath (230) such that the proximal surface of torque member (250) rests against the distal surface of flange (234). As noted above, sheath (230) fits into bore (252) of torque member (250), such that torque member (250) may simply be slid onto sheath (230). It should be understood that the steps shown in FIGS. 8C and 8D may be reversed, performed simultaneously, or otherwise be combined with other assembly steps described herein.

Figure 8E:
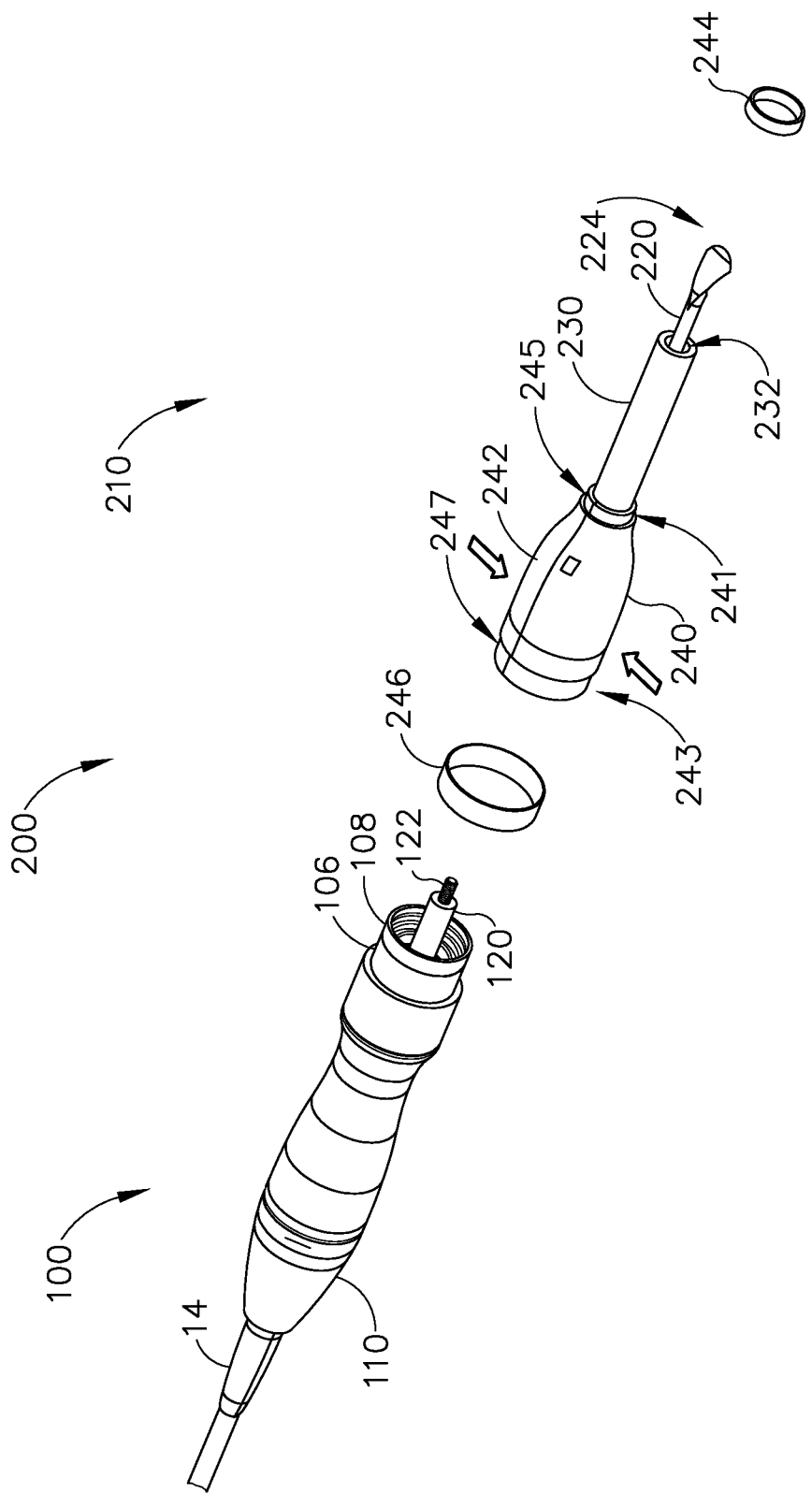
FIG. 8E depicts an exploded perspective view of the instrument of FIG. 7, showing the instrument in a fourth partially assembled state.

Once connector (260) and torque member (250) have been suitably positioned in relation to sheath (230), and sheath (230) and waveguide (220) have been coupled together, shroud halves (240, 242) are then maneuvered toward sheath (230) such that the proximal portion of sheath (230) is captured between shroud halves (240, 242) as shown in FIG. 8E. Referring back to FIG. 10, an exterior surface of torque member (250) presents a pair of longitudinal channels (258) in the present example. The interior regions of shroud halves (240, 242) each include a respective key feature (not shown) that is configured to fit within channels (258) of torque member (250) when shroud halves (240, 242) are positioned about torque member (250). Thus, as shroud halves (240, 242) are rotated, torque member (250) is concurrently rotated. It should therefore be understood that shroud halves (240, 242) and torque member (250) rotate together unitarily when shaft assembly (210) is fully assembled. The distal end of each shroud half (240, 242) includes a respective recess (241, 245). Recesses (241, 245) align with each other to form a complete annular recess when shroud halves (240, 242) are joined together as shown in FIG. 8E. Similarly, the proximal end of each shroud half (240, 242) includes a respective recess (243, 247). Recesses (243, 247) also align with each other to form a complete annular recess when shroud halves (240, 242) are joined together as shown in FIG. 8E.

Figure 8F:
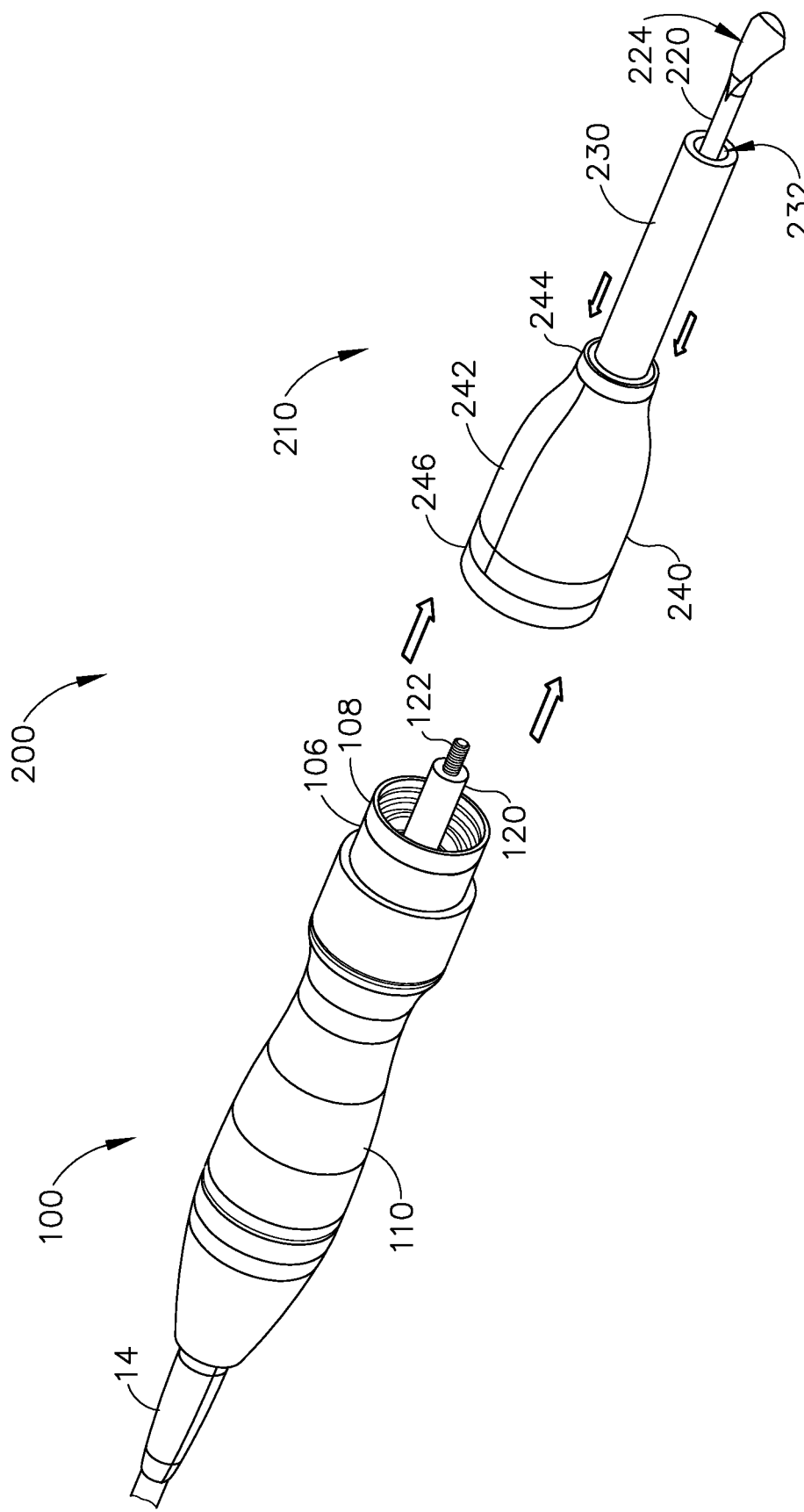
FIG. 8F depicts an exploded perspective view of the instrument of FIG. 7, showing the instrument in a fifth partially assembled state.

Once shroud halves (240, 242) have been joined together as shown in FIG. 8E, a distal retaining ring (244) is slid proximally over aligned recesses (241, 245), as shown in FIG. 8F. Similarly, a proximal retaining ring (246) is slid distally over aligned recesses (243, 247), as also shown in FIG. 8F. Retaining rings (244, 246) are configured to hold shroud halves (240, 242) together. At this stage, shaft assembly (210) is completely assembled. Retaining rings (244, 246) may engage shroud halves (240, 242) with an interference fit, such that retaining rings (244, 246) remain coupled with shroud halves (240, 242) due to friction. It should be understood that shaft assembly (210) may be provided to an end user in the configuration shown in FIG. 8F, such that the end user need not perform any of the assembly steps shown in FIGS. 8A-8F.

Figure 8G:
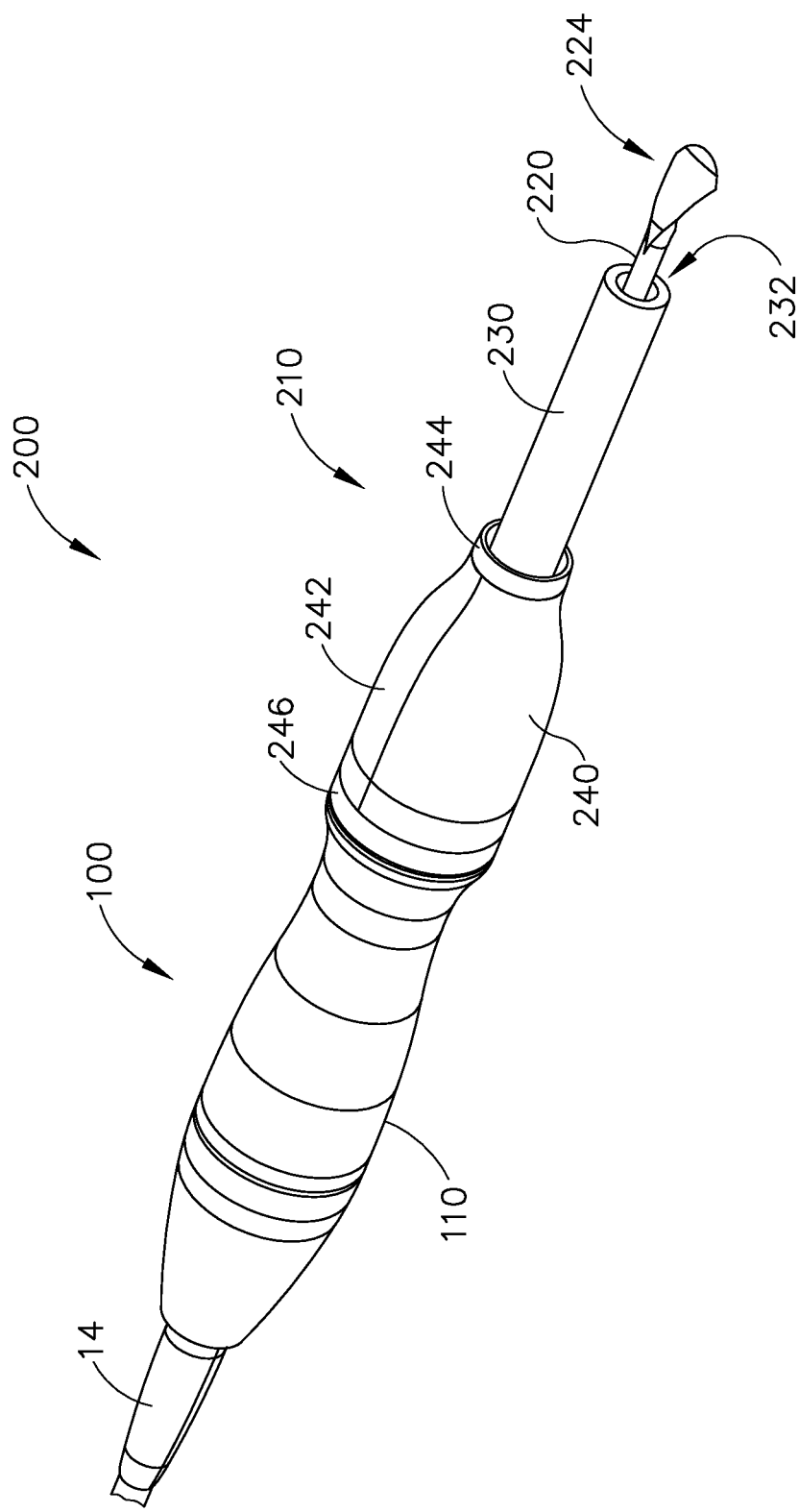
FIG. 8G depicts a perspective view of the instrument of FIG. 7, showing the instrument in an assembled state.
Figure 9:
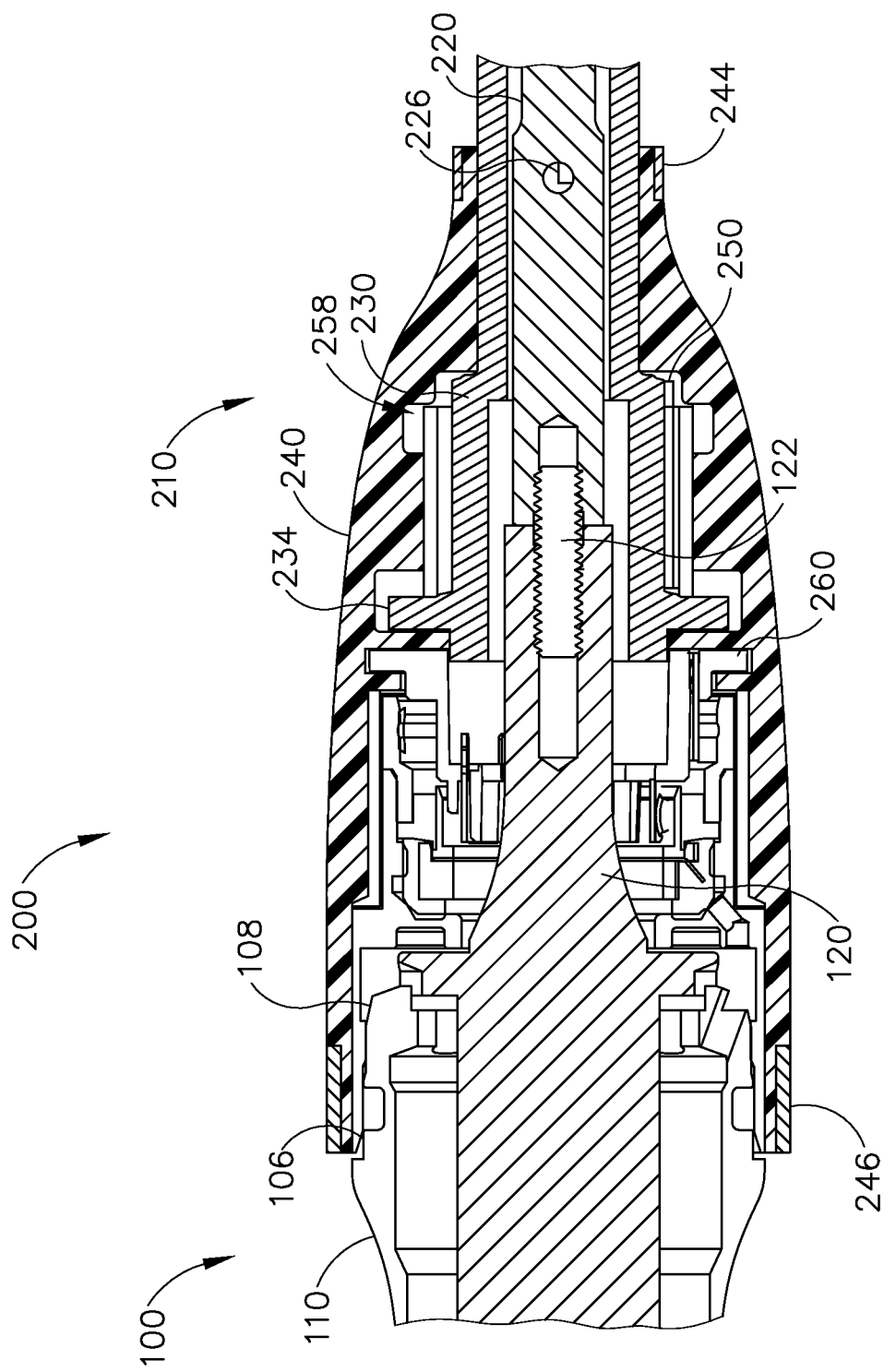
FIG. 9 depicts a partial cross-sectional view of the instrument of FIG. 7.

Once shaft assembly (210) has been fully assembled, shaft assembly (210) may be readily coupled with transducer assembly (100) as shown in FIGS. 8G and 9. In particular, the user may first maneuver shaft assembly (210) proximally toward transducer assembly (100). During this stage, connector (260) may assist in guiding shaft assembly (210) into axial alignment with transducer assembly (100) as noted above. The user may then grasp shroud halves (240, 242) and rotate shaft assembly (210) relative to transducer assembly (100) to mechanically and acoustically couple waveguide (220) with horn (120) via threaded stud (122) and a threaded bore (222) formed in a proximal end of waveguide (220).

Figure 11A:
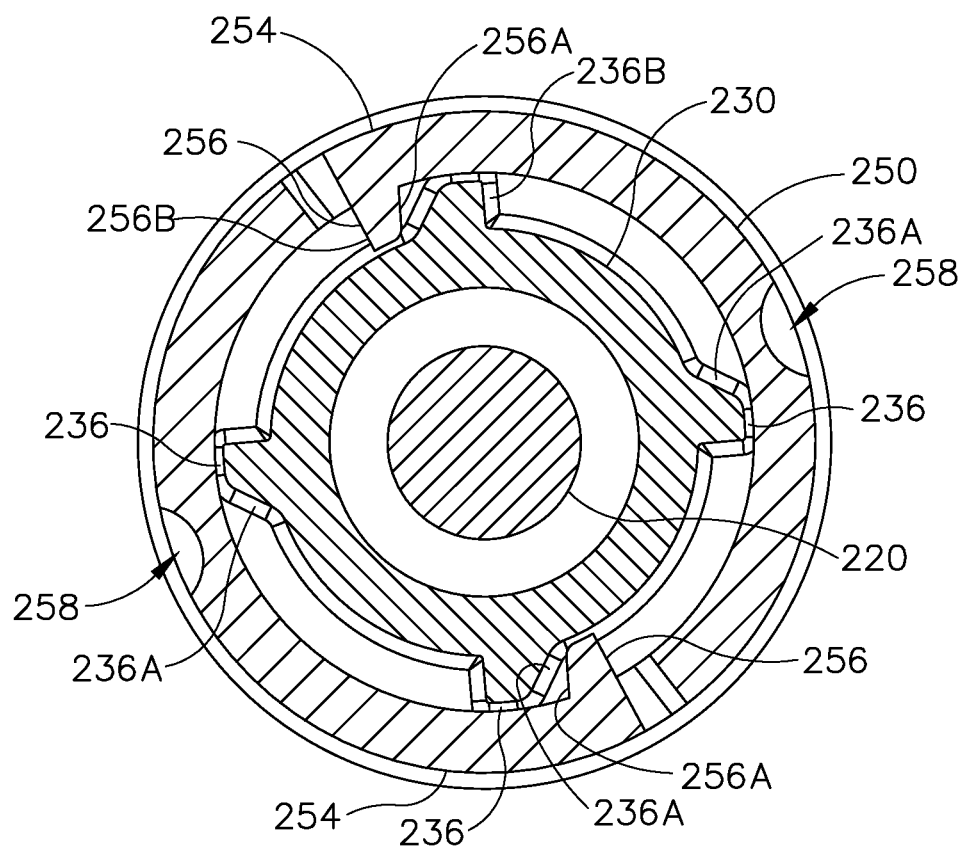
FIG. 11A depicts a cross-sectional view of the sheath and the ratcheting feature of the instrument of FIG. 7, with the sheath in a first rotational position.
Figure 11B:
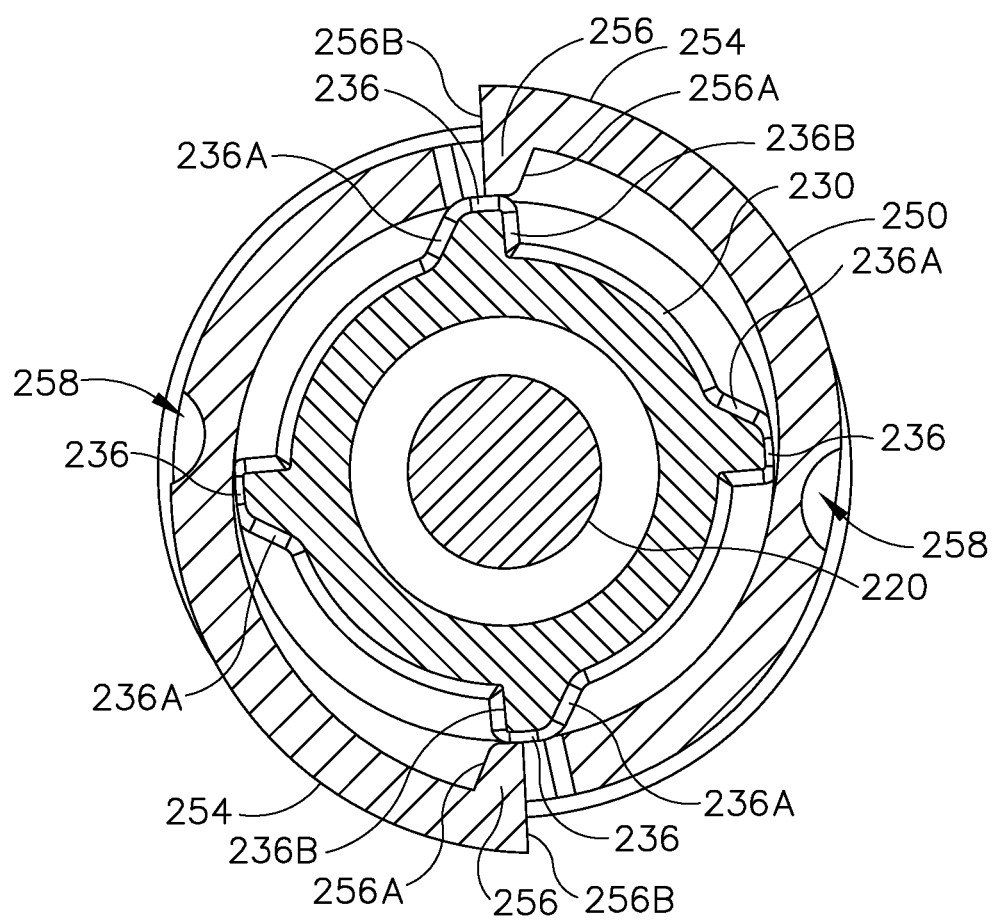
FIG. 11B depicts a cross-sectional view of the sheath and the ratcheting feature of the instrument of FIG. 7, with the sheath in a second rotational position.
Figure 11C:
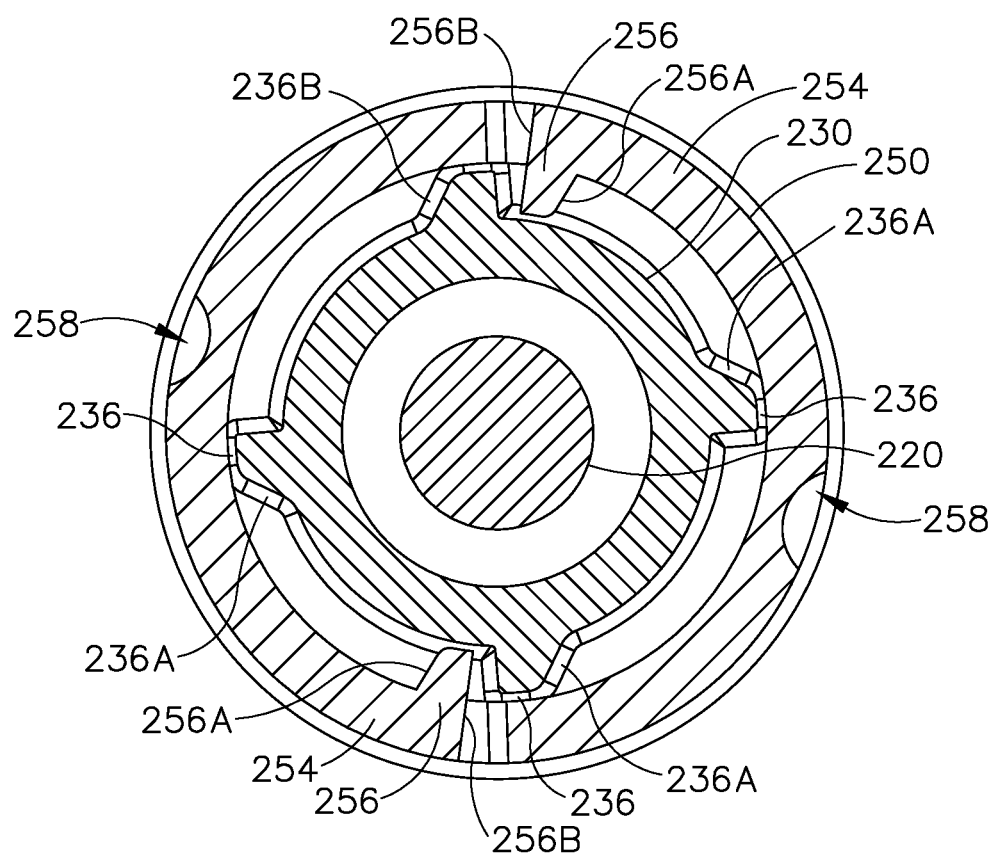
FIG. 11C depicts a cross-sectional view of the sheath and the ratcheting feature of the instrument of FIG. 7, with the sheath in a third rotational position.

FIGS. 11A-11C show the interaction of torque member (250) and sheath (230) as waveguide (220) is connected with transducer assembly (100) through rotation of shaft assembly (210) relative to transducer assembly (100). It should be understood that the stages shown in FIGS. 11A-11C correspond with the stage shown in FIG. 8G. It should also be understood that, during the stages shown in FIGS. 11A-11C, the user may be grasping transducer assembly (100) with one hand and grasping shroud halves (240, 242) with the other hand, thereby rotating shroud halves (240, 242) relative to transducer assembly (100). As shroud halves (240, 242) are rotated clockwise relative to transducer assembly (100), torque member (250) rotates as well because of the engagement between the key features of shroud halves (240, 242) and longitudinal channels (258) of torque member (250). During the initial stage of this rotation, tabs (256) rotate into engagement with longitudinal projections (236) as shown in FIG. 11A. With tabs (256) engaging longitudinal projections (236), the user continues to rotate shroud halves (240, 242) clockwise relative to transducer assembly (100) through a first range of motion. During this first range of motion, tabs (256) continue to engage longitudinal projections (236) such that torque member (250) rotates sheath (230) and waveguide (220) relative to transducer assembly (100). Waveguide (220) is thereby coupled with threaded stud (122).

As the user completes the first range of motion, waveguide (220) is secured to threaded stud (122) with a certain predetermined amount of torque. Once the assembly of waveguide (220) and threaded stud (122) reaches the predetermined amount of torque, and the user continues to rotate shroud halves (240, 242) clockwise relative to transducer assembly (100) past the first range of motion, resilient members (254) deflect outwardly as shown in FIG. 11B. In particular, angular surfaces (236A) of longitudinal projections (236) and angular surface (256A) of tabs (256) drive resilient members (254) outwardly through a cam action, such that torque member (250) no longer rotates sheath (230). As the user continues to rotate shroud halves (240, 242), torque member (250) continues to rotate such that tabs (256) eventually clear longitudinal projections (236) and snap inwardly as shown in FIG. 11C. This inward snapping/ratcheting may provide audible and/or tactile feedback to indicate to the user that an appropriate amount of torque has been achieved in the coupling of waveguide (220) with threaded stud (122). It should be understood that from this point on, any further clockwise rotation of shroud halves (240, 242) and torque member (250) no longer causes rotation of sheath (230) and waveguide (220) relative to transducer assembly (100). It should also be understood that the rigidity of resilient members (254) may be changed to thereby change the maximum amount of torque that may be applied to waveguide (220).

A surface (256B) of each tab (256) and a surface (236B) of each longitudinal projection (236) is substantially flat such that as torque member (250) is rotated counterclockwise relative to transducer assembly (100), contact between longitudinal projections (236) of sheath and tabs (256) will not drive resilient members (254) outwardly. It should therefore be understood that rotation of shroud halves (240, 242) and torque member (250) relative to transducer assembly (100) in a counterclockwise motion will not cause slipping or ratcheting of torque member (250). Thus, when the user wishes to disassemble shaft assembly (210) from transducer assembly (100) at the end of a surgical procedure, the user may simply grasp shroud halves (240, 242) with one hand and rotate shroud halves (240, 242) counterclockwise relative to transducer assembly (100) while gripping transducer assembly (100) with the other hand, until waveguide (220) is decoupled from threaded stud (122) of transducer assembly (100). The user may then simply pull shaft assembly (210) away from transducer assembly (100). At this stage, shaft assembly (210) may be disposed of; while transducer assembly (100) may be reconditioned any reused. Alternatively, the user may wish to handle these components in some other fashion.

It should be understood that the integral torque assembly features of shaft assembly (210) eliminate the need for a separate torque wrench (e.g., such as torque wrench (50), etc.) to secure waveguide (220) with horn (120). It should also be understood that, during use of assembled instrument (200), the distal portion of sheath (230) proximal to ultrasonic blade (224) may be grasped by a user during operation to grasp instrument (200) in a pencil-like manner. Holding instrument (200) with a pencil grip may enable the user to provide very fine and precise movement with blade (224), such as in a facial plastic surgery procedure or some other fine and precise surgical procedure.

B. Exemplary Integral Torque Assembly with Dual Shroud and Resilient Features

FIGS. 13-17C show another exemplary instrument (300) that incorporates torque assembly (250), sheath (230), and connector (260) of instrument (200) discussed above. Instrument (300) of the present example is configured to operate substantially similar to instruments (10, 200) discussed above except for the differences discussed below. Instrument (300) is thus operable to transect and/or seal tissue at a surgical site. Furthermore, torque member (250) is configured to operate substantially similar within instrument (300) as was discussed in relation to instrument (200) above. In particular, torque member (250) is configured to limit the amount of torque that may be applied to couple a waveguide (320) with transducer assembly (100); and provide audible/tactile feedback to indicate that the appropriate amount of torque has been achieved. Instrument (300) of the present example comprises transducer assembly (100) and a shaft assembly (310). Shaft assembly (310) comprises a waveguide (320), sheath (230), a pair of shroud halves (340, 342), a retaining ring (344), a retaining sleeve (346), torque member (250), connector (260), a retaining member (360), and a spring (370). Shaft assembly (310) also includes a user input feature (311) that is operable to selectively activate transducer assembly (100), to thereby selectively activate ultrasonic blade (324) of waveguide (320). User input feature (311) may be constructed and operable in accordance with the teachings herein relating to user input feature (211) of instrument (200).

Figure 14A:
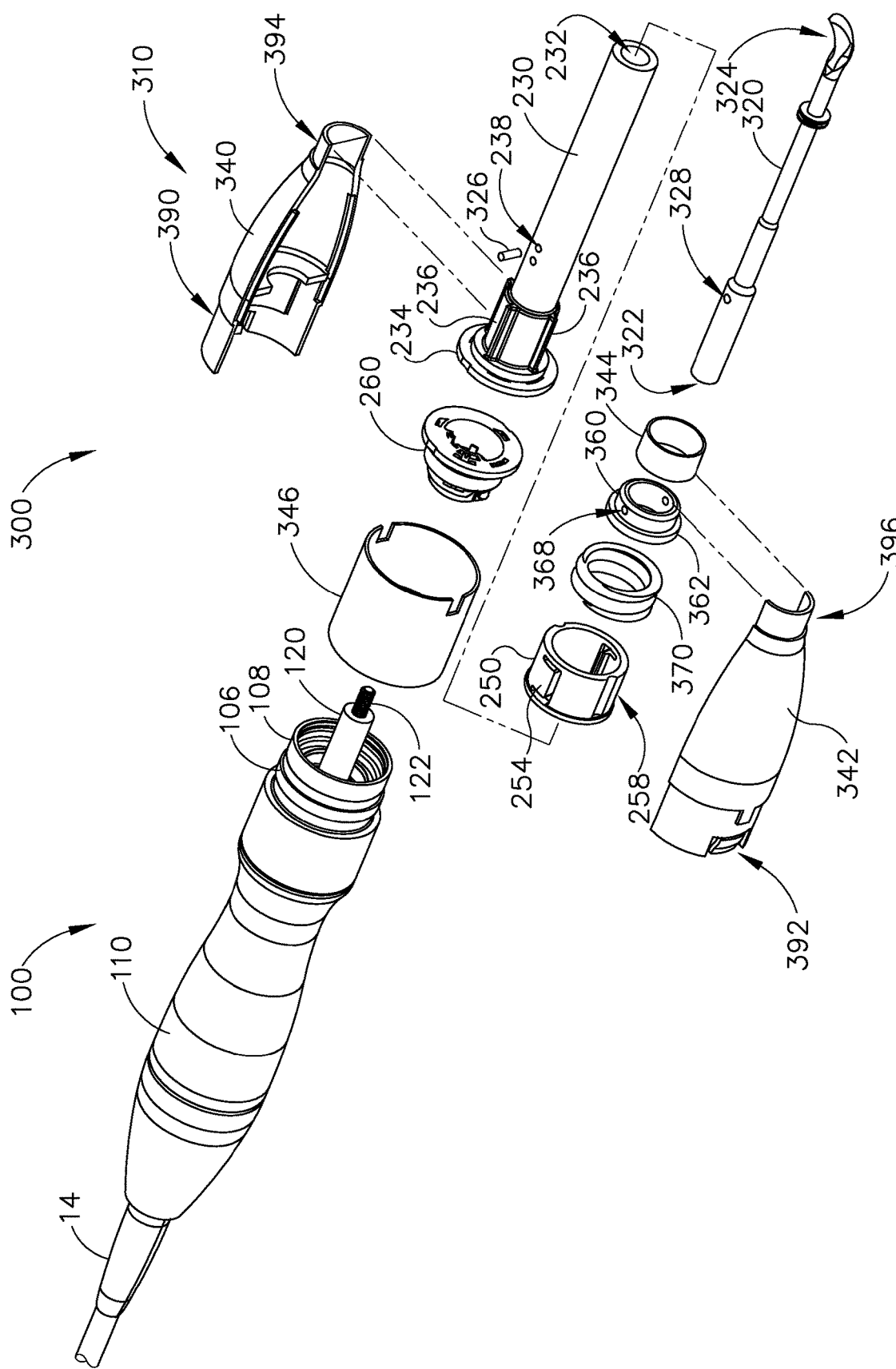
FIG. 14A depicts an exploded perspective view of the instrument of FIG. 13, showing the instrument in a disassembled state.
Figure 14B:
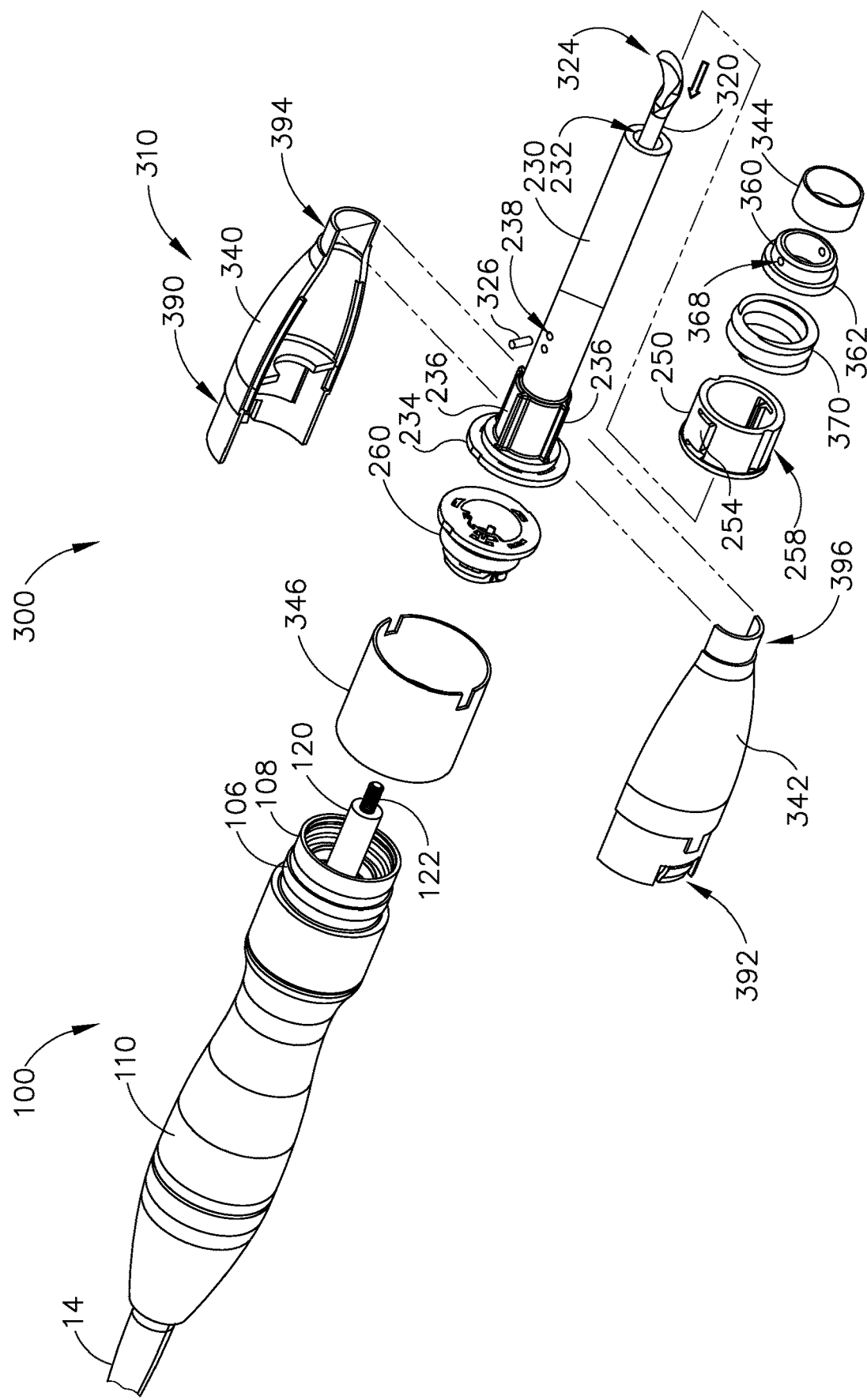
FIG. 14B depicts an exploded perspective view of the instrument of FIG. 13, showing the instrument in a first partially assembled state.
Figure 14C:
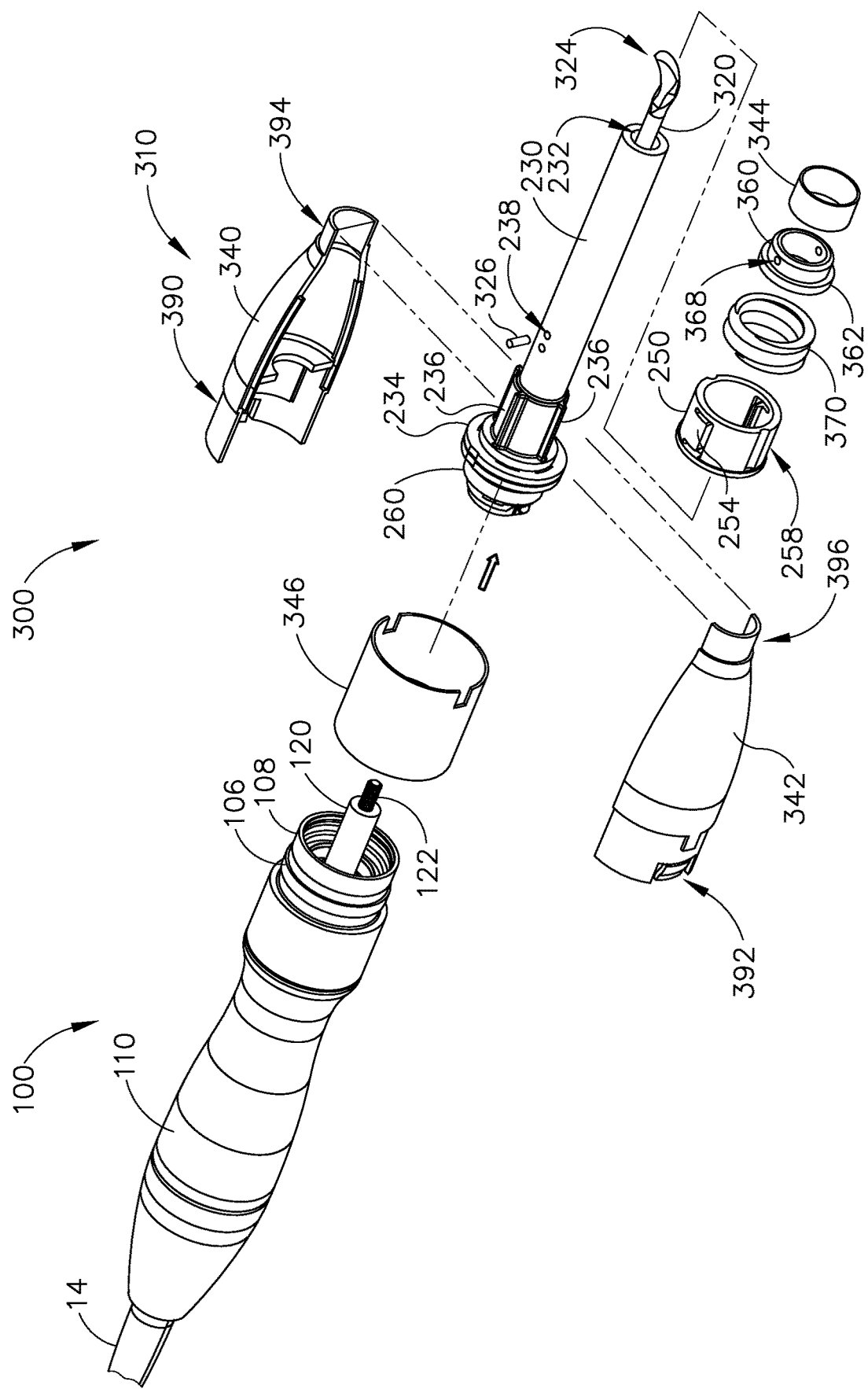
FIG. 14C depicts an exploded perspective view of the instrument of FIG. 13, showing the instrument in a second partially assembled state.

FIGS. 14A-14G show exemplary steps for assembling instrument (300). FIG. 14A shows instrument (300) in a disassembled state, including shaft assembly (310) in a disassembled state. In an initial assembly step, waveguide (320) is inserted into interior bore (232) of sheath (230) such that an ultrasonic blade (324) of waveguide (320) extends from the distal end of sheath (230) as shown in FIG. 14B. A transverse opening (328) of waveguide (320) is aligned with complementary transverse openings (238) of sheath (230). Connector (260) is then coupled to a proximal surface of flange (234) of sheath (230), as shown in FIG. 14C. As described above, connector (260) is configured to insertingly fit in cavity (108) of transducer assembly (100) and thereby guide shaft assembly (210) into aligned engagement with transducer assembly (100). As also described above, electrical contact features (262, 265) of connector (260) provide electrical coupling between user input feature (311) and transducer assembly (100).

Figure 14D:
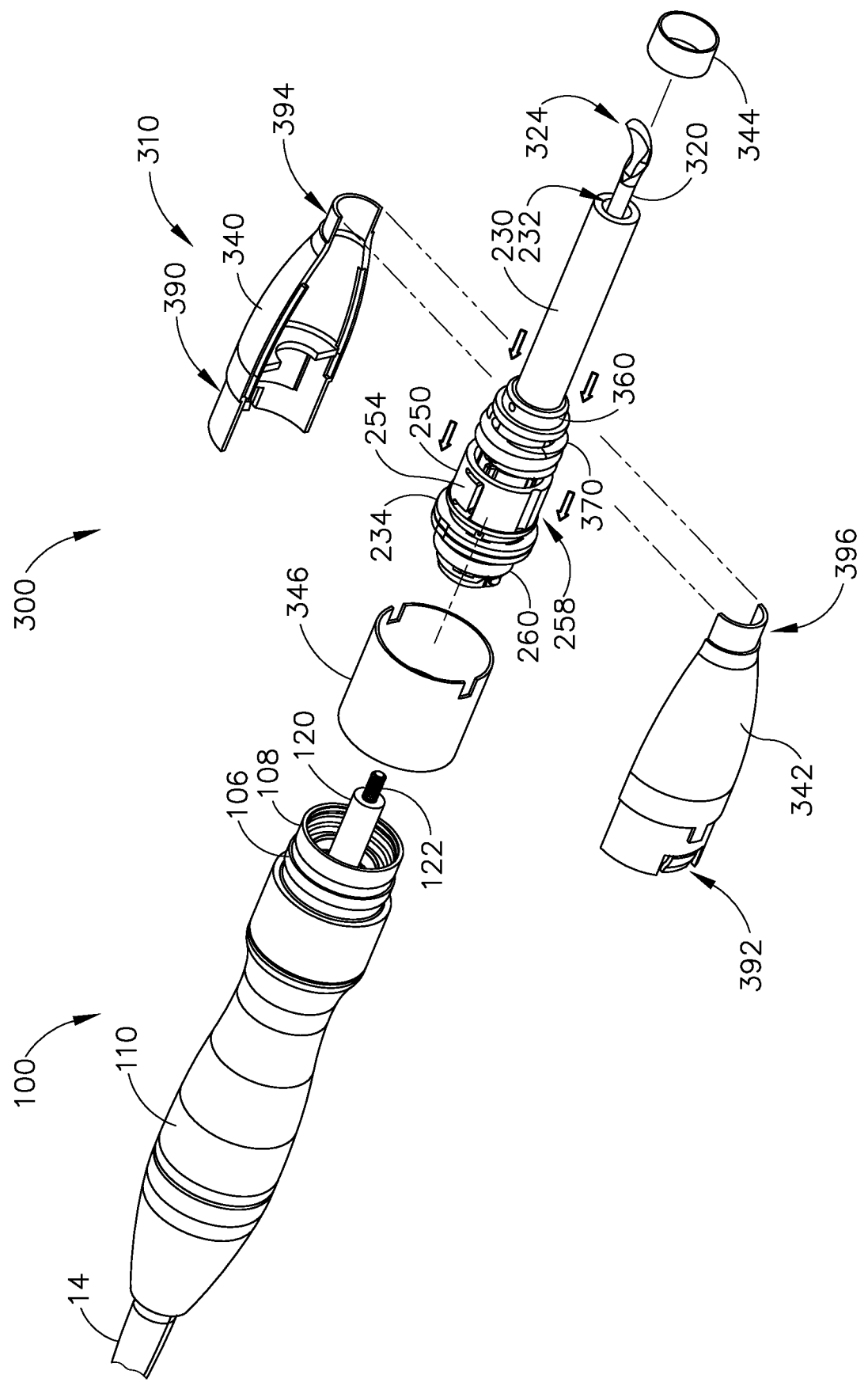
FIG. 14D depicts an exploded perspective view of the instrument of FIG. 13, showing the instrument in a third partially assembled state.
Figure 16:
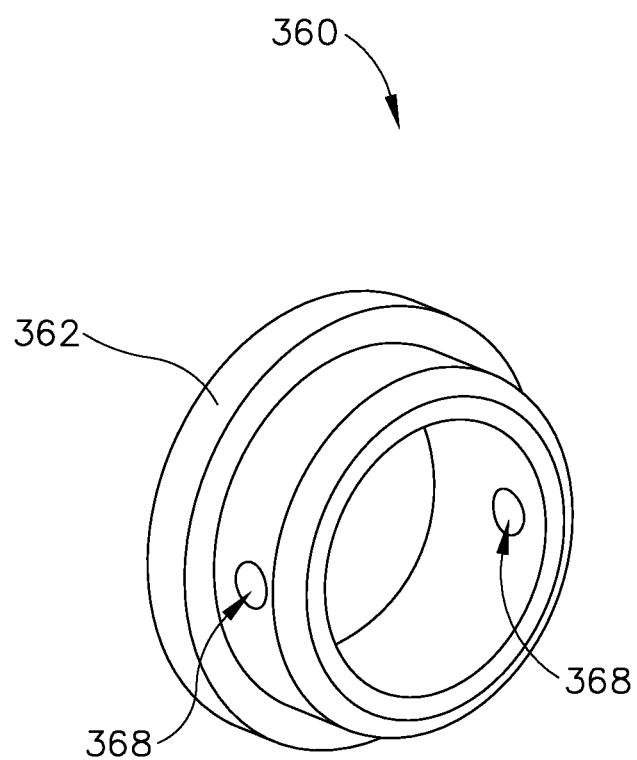
FIG. 16 depicts a perspective view of the retaining member of the instrument of FIG. 13.

As shown in FIG. 14D, torque member (250) is then positioned about sheath (230) such that the proximal surface of torque member (250) rests against the distal surface of flange (234). As noted above, sheath (230) fits into bore (252) of torque member (250), such that torque member (250) may simply be slid onto sheath (230). As also shown in FIG. 14D, spring (370) and retaining member (360) are also positioned about sheath (230). Spring (370) is positioned proximal to retaining member (360). As best seen in FIG. 16, retaining member (360) has a pair of openings (368) that align with openings (238, 328). A pin (326) is passed through aligned openings (238, 328, 368) in sheath (230), waveguide (320), and retaining member (360) to thereby couple sheath (230), waveguide (320), and retaining member (360), such that rotation of sheath (230) causes concurrent rotation of waveguide (320) and retaining member (360). It should therefore be understood that sheath (230), waveguide (320), and retaining member (360) rotate together unitarily when shaft assembly (310) is fully assembled. Opening (328) is located at a position along the length of waveguide (320) corresponding to a node associated with resonant ultrasonic vibrations communicated through waveguide (320), such that the ultrasonic vibrations are not communicated to pin (326). It should be understood that the steps shown in FIGS. 14C and 14D may be reversed, performed simultaneously, or otherwise be combined with other assembly steps described herein.

Figure 14E:
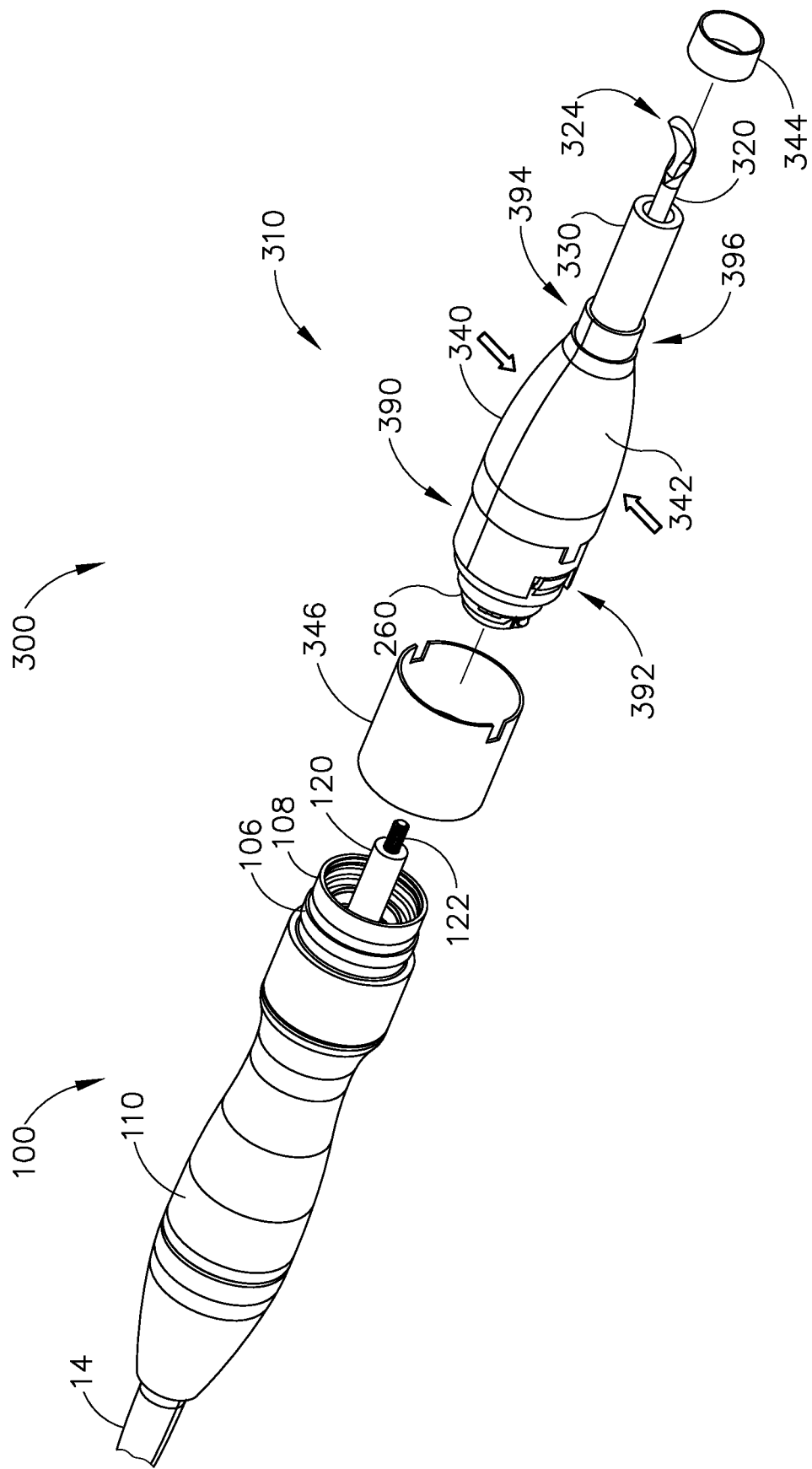
FIG. 14E depicts an exploded perspective view of the instrument of FIG. 13, showing the instrument in a fourth partially assembled state.

Once connector (260) and torque member (250) have been suitably positioned in relation to sheath (230), and sheath (230) and waveguide (320) have been coupled together with retaining member (360), shroud halves (340, 342) are then maneuvered toward sheath (230) such that the proximal portion of sheath (230) is captured between shroud halves (340, 342) as shown in FIG. 14E. As discussed above, an exterior surface of torque member (250) presents a pair of longitudinal channels (258). The interior regions of shroud halves (340, 342) of the present example each include a respective key feature (341, 343) configured to fit within channels (258) of torque member (250) when shroud halves (340, 342) are positioned about torque member (250). Thus, as shroud halves (340, 342) are rotated, torque member (250) is concurrently rotated. It should therefore be understood that shroud halves (340, 342) and torque member (250) rotate together unitarily when shaft assembly (310) is fully assembled. The distal end of each shroud half (340, 342) includes a respective recess (390, 392). Recesses (390, 392) align with each other to form a complete annular recess when shroud halves (340, 342) are joined together as shown in FIG. 14E. Similarly, the proximal end of each shroud half (340, 342) includes a respective recess (394, 396). Recesses (394, 396) also align with each other to form a complete annular recess when shroud halves (340, 342) are joined together as shown in FIG. 14E.

Figure 14F:
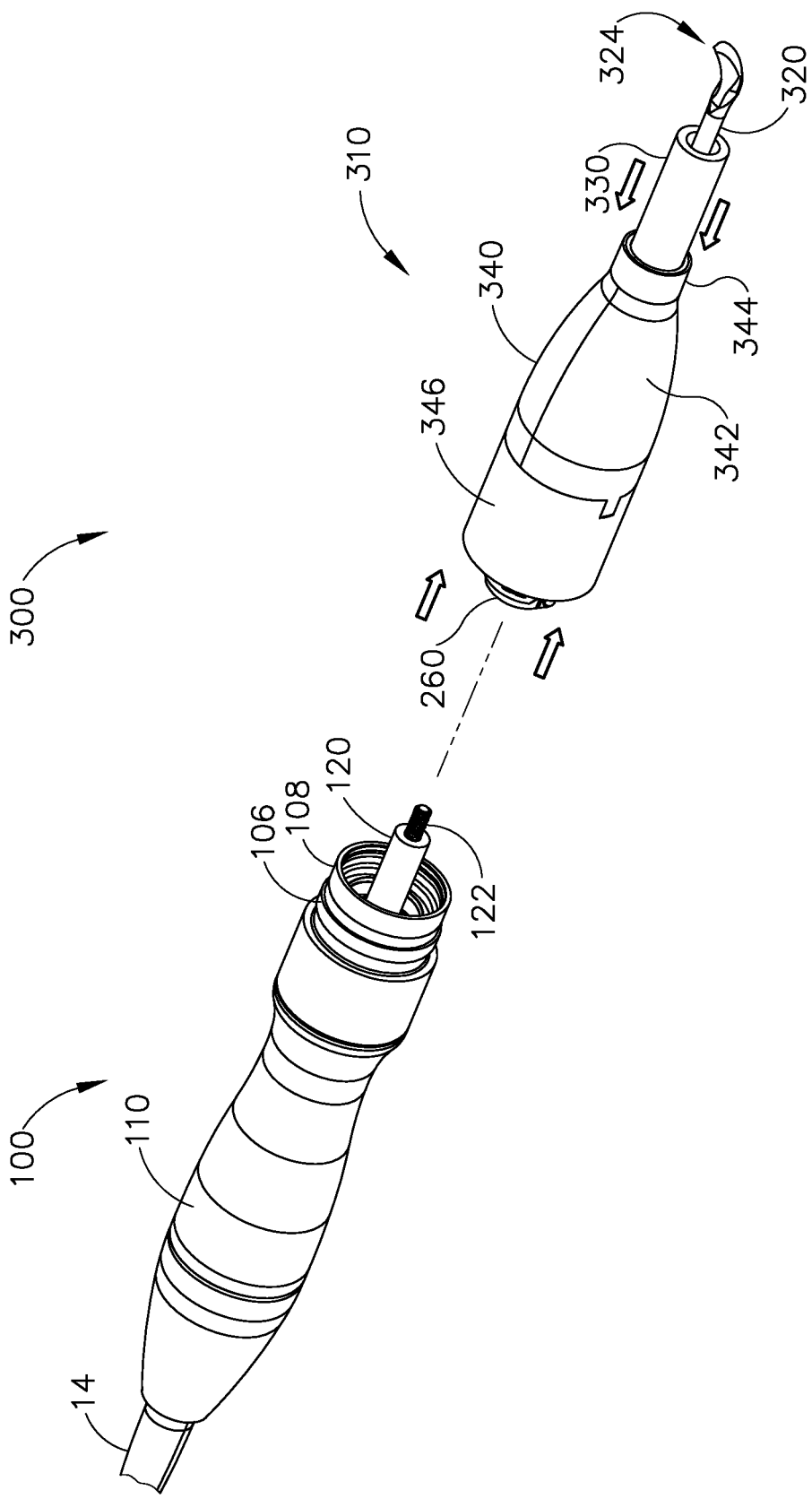
FIG. 14F depicts an exploded perspective view of the instrument of FIG. 13, showing the instrument in a fifth partially assembled state.

Once shroud halves (340, 342) have been joined together as shown in FIG. 14E, retaining ring (344) is slid proximally over aligned recesses (394, 396), as shown in FIG. 14F. Similarly, retaining sleeve (346) is slid distally over aligned recesses (390, 392), as also shown in FIG. 14F. Retaining ring (344) and sleeve (346) are configured to hold shroud halves (340, 342) together. At this stage, shaft assembly (310) is completely assembled. Retaining ring (344) and sleeve (346) may engage shroud halves (340, 342) with an interference fit, such that retaining ring (344) and sleeve (346) remain coupled with shroud halves (340, 342) due to friction. It should be understood that shaft assembly (310) may be provided to an end user in the configuration shown in FIG. 14F, such that the end user need not perform any of the assembly steps shown in FIGS. 14A-14F.

Figure 14G:
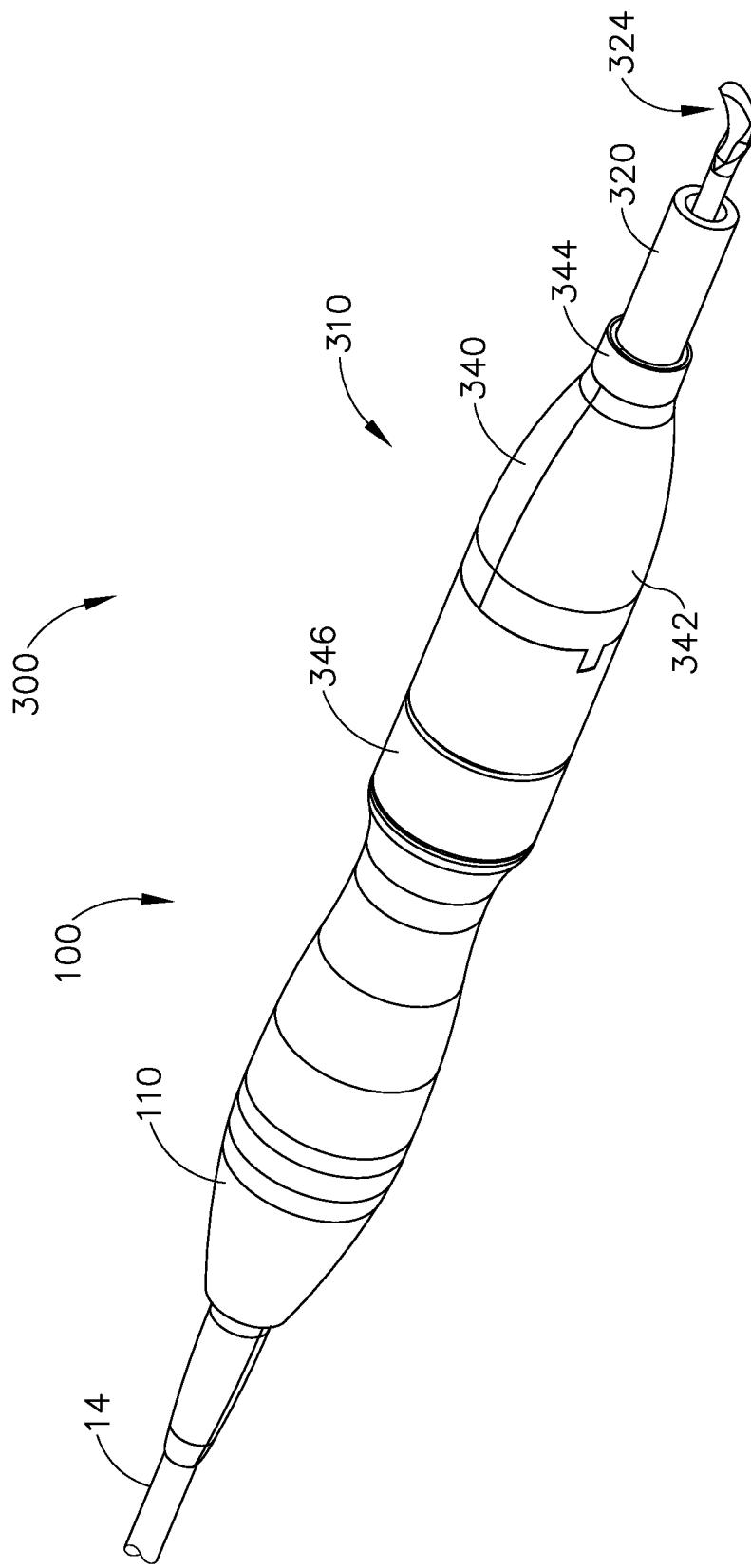
FIG. 14G depicts a perspective view of the instrument of FIG. 13, showing the instrument in an assembled state.
Figure 15:
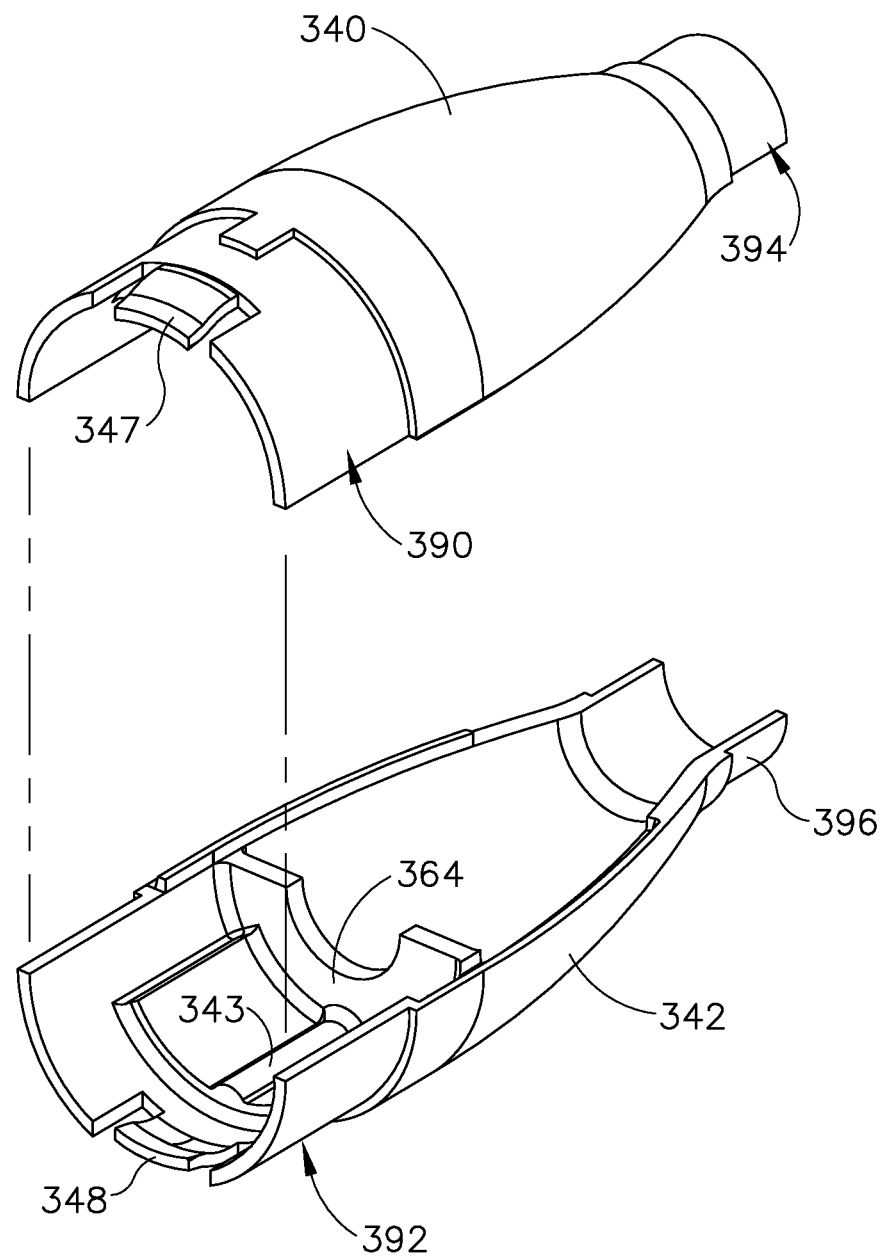
FIG. 15 depicts a perspective view of the shroud halves of the instrument of FIG. 13.

Once shaft assembly (310) has been fully assembled, shaft assembly (310) may be readily coupled with transducer assembly (100) as shown in FIG. 14G. In particular, the user may first maneuver shaft assembly (310) proximally toward transducer assembly (100). During this stage, connector (260) may assist in guiding shaft assembly (310) into axial alignment with transducer assembly (100) as noted above. The user may then grasp shroud halves (340, 342) and rotate shaft assembly (310) relative to transducer assembly (100) to mechanically and acoustically couple waveguide (320) with horn (120) via threaded stud (122) and a threaded bore (322) formed in a proximal end of waveguide (320).

As the user rotates rotate shaft assembly (310) relative to transducer assembly (100) to mechanically and acoustically couple waveguide (320) with horn (120), torque member (250) and sheath (230) may interact as described above with respect to FIGS. 11A-11C. In particular, as the user rotates shroud halves (240, 242) clockwise relative to transducer assembly (100) through a first range of motion, tabs (256) engage longitudinal projections (236) such that torque member (250) rotates sheath (230) and waveguide (320) relative to transducer assembly (100). Waveguide (320) is thereby coupled with threaded stud (122) with a certain predetermined amount of torque. Once the assembly of waveguide (320) and threaded stud (122) reaches the predetermined amount of torque, and the user continues to rotate shroud halves (240, 242) clockwise relative to transducer assembly (100) past the first range of motion, resilient members (254) deflect outwardly, such that torque member (250) no longer rotates sheath (230). As the user continues to rotate shroud halves (240, 242), tabs (256) snap inwardly and thus provide audible and/or tactile feedback to indicate to the user that an appropriate amount of torque has been achieved in the coupling of waveguide (320) with threaded stud (122). Any further clockwise rotation of shroud halves (240, 242) and torque member (250) no longer causes rotation of sheath (230) and waveguide (320) relative to transducer assembly (100). If the user wishes to decouple shaft assembly (310) from transducer assembly (100), the user may grasp shroud halves (340, 342) with one hand and rotate shroud halves (340, 342) counterclockwise relative to transducer assembly (100) while gripping transducer assembly (100) with the other hand, until waveguide (320) is decoupled from threaded stud (122) of transducer assembly (100). The user may then simply pull shaft assembly (310) away from transducer assembly (100).

Figure 17A:
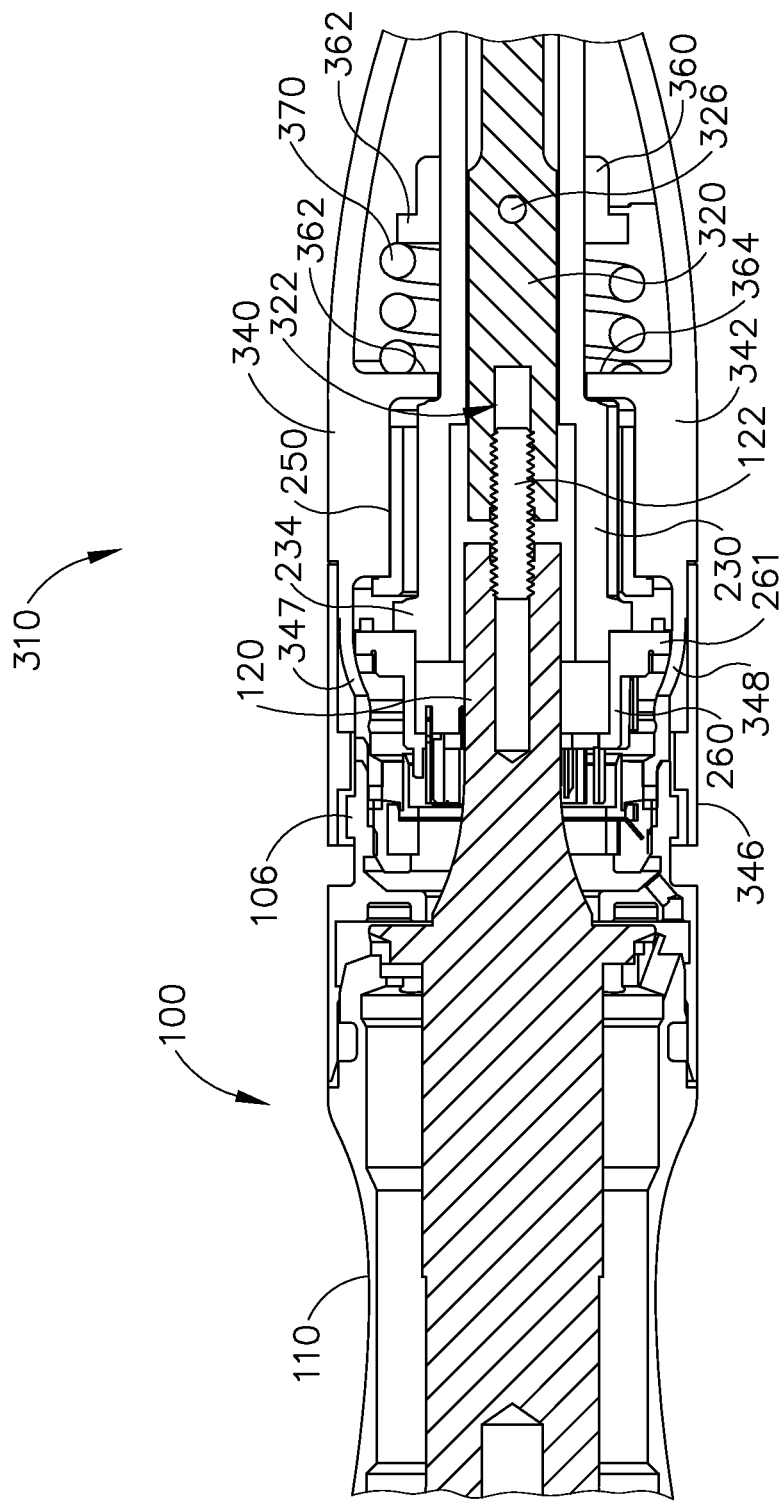
FIG. 17A depicts a partial cross-sectional view of the instrument of FIG. 13, with shroud halves of the shaft assembly in a distal position and a waveguide of the shaft assembly in a distal position.
Figure 17B:
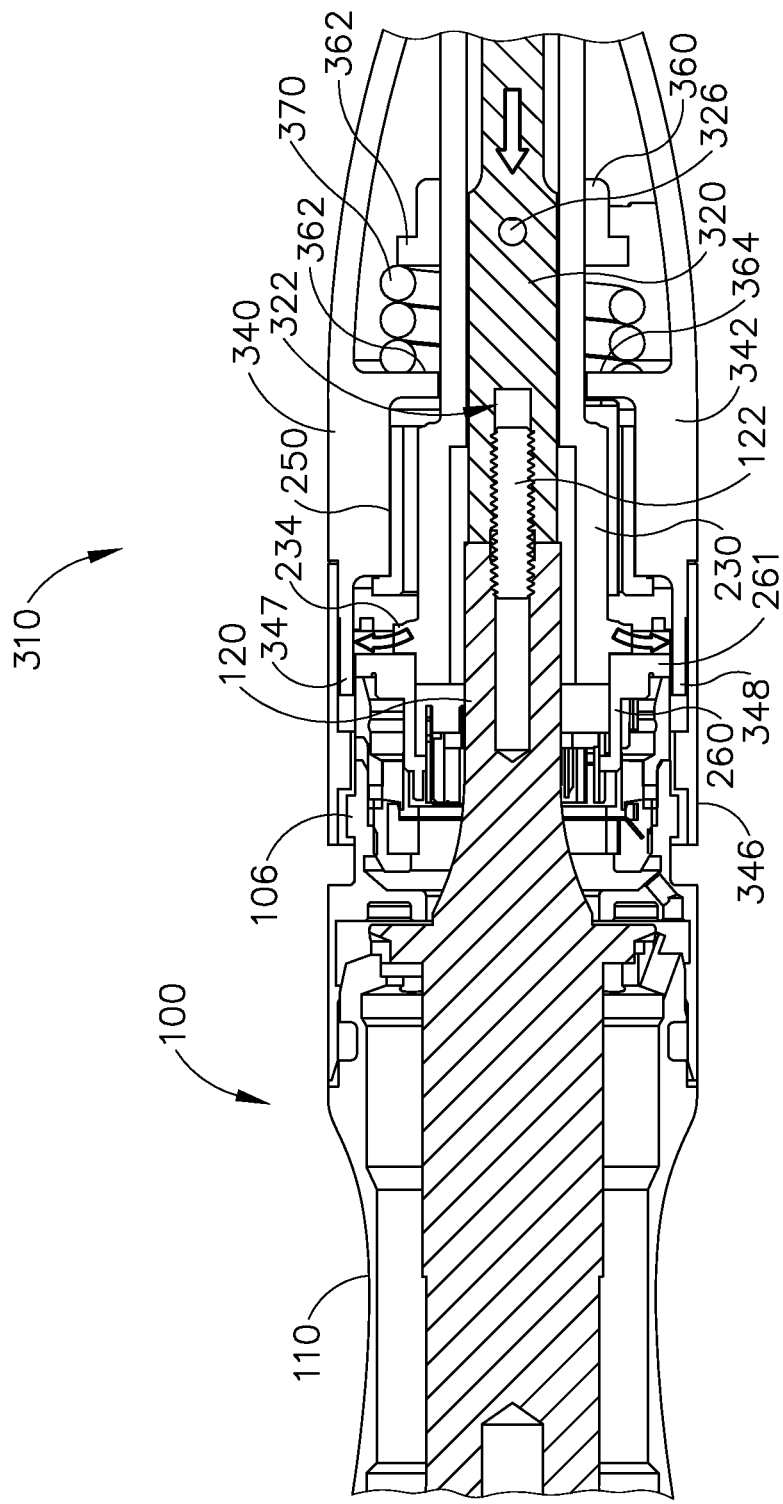
FIG. 17B depicts a partial cross-sectional view of the instrument of FIG. 13, with the shroud halves of the shaft assembly in the distal position and the waveguide of the shaft assembly in a proximal position.
Figure 17C:
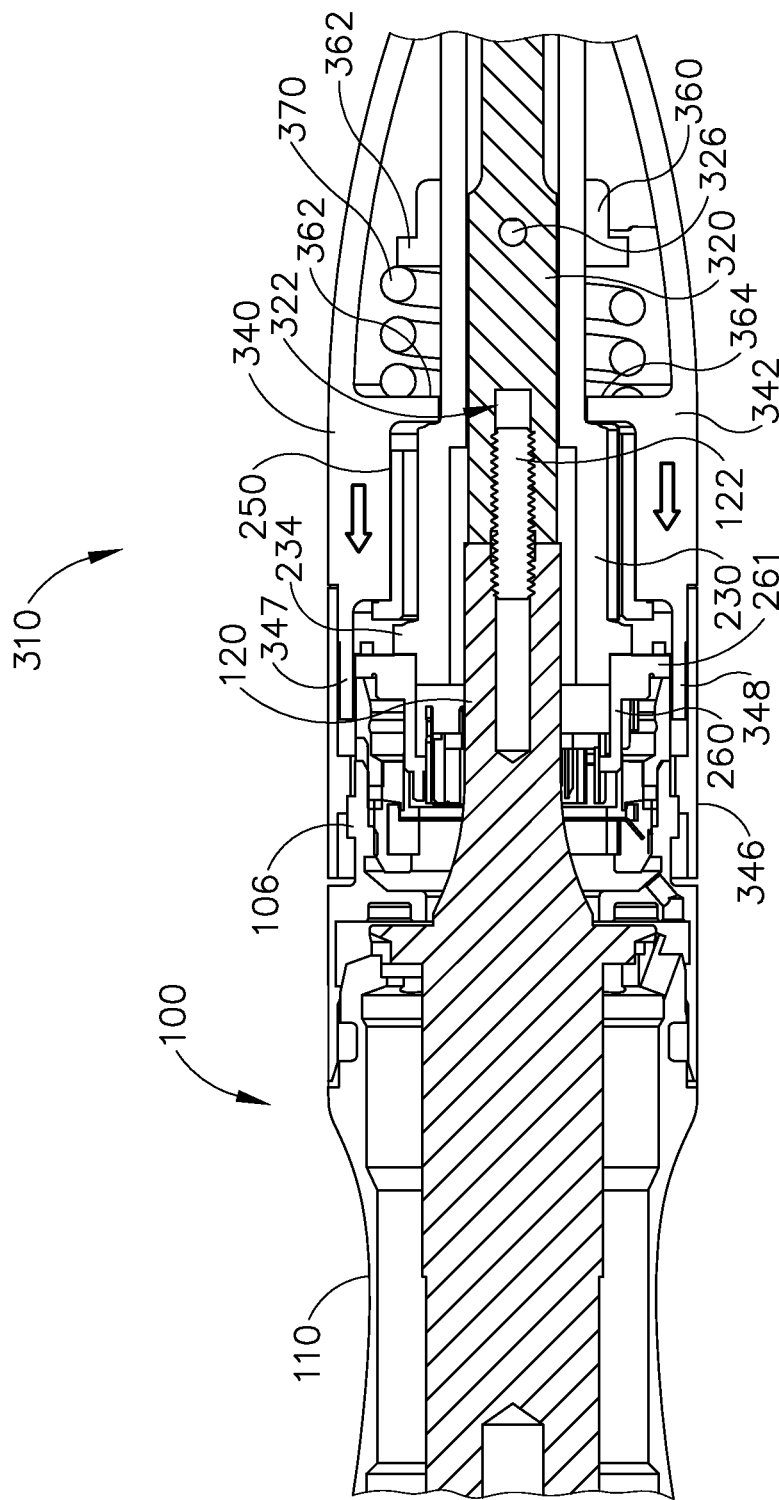
FIG. 17C depicts a partial cross-sectional view of the instrument of FIG. 13, with the shroud halves of the shaft assembly in a proximal position and a waveguide of the shaft assembly in the proximal position.
Figure 18:
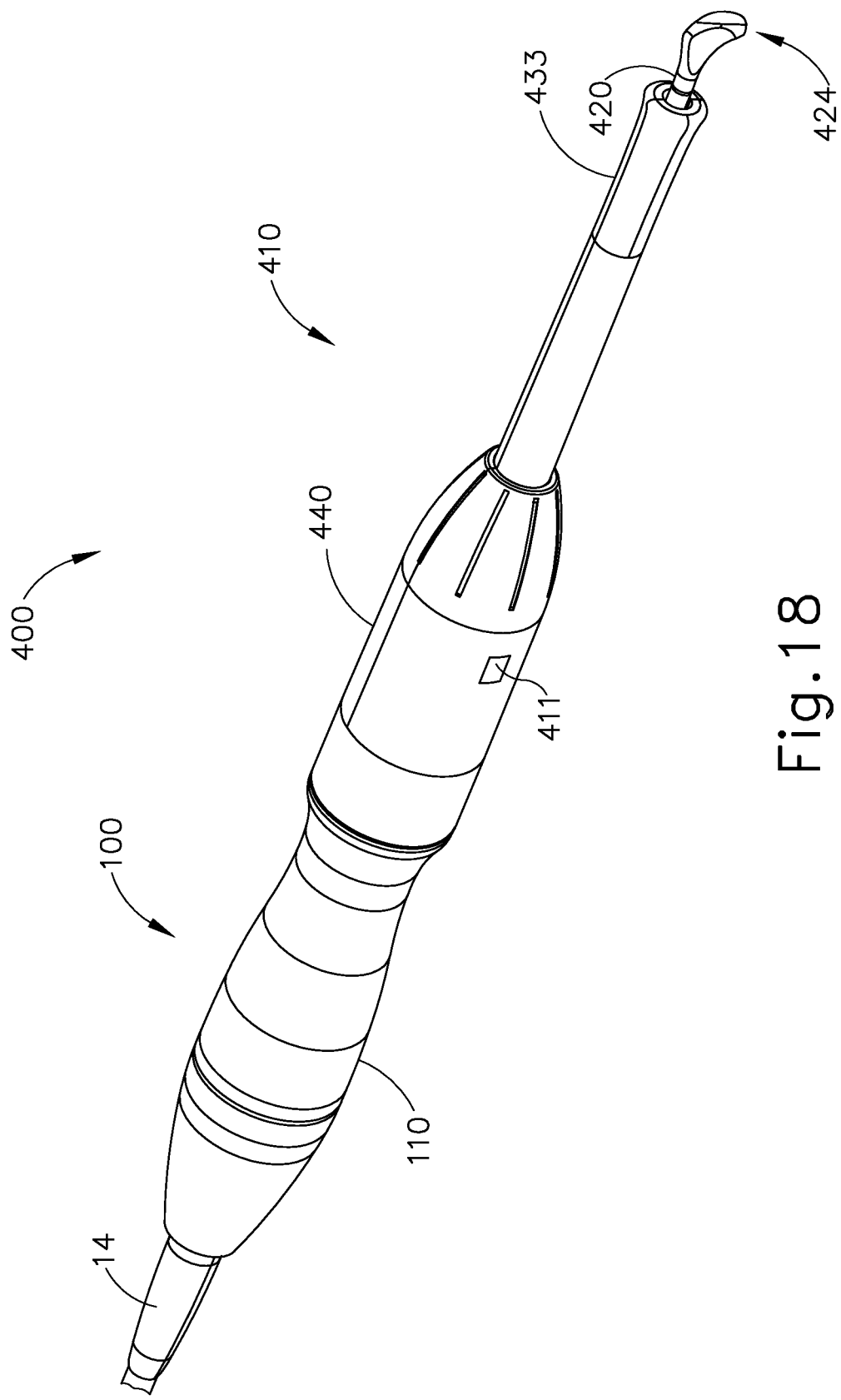
FIG. 18 depicts a perspective view of yet another exemplary alternative surgical instrument.

As shown in FIGS. 15 and 17A-17C, a proximal end of each shroud half (340, 342) includes an inwardly extending flange (362, 364). When shroud halves (340, 342) are positioned about sheath (230), spring (370), and retaining member (360) are positioned distal to flanges (362, 364) such that spring (370) bears against a distal surface of flanges (362, 364) and a proximal surface of flange (362) of retaining member (360). It should therefore be understood spring (370) biases retaining member (360), sheath (230), and waveguide (320) distally relative to shroud halves (340, 342). The proximal end of each shroud half (340, 342) also includes an inwardly biased resilient tab (347, 348). Resilient tabs (347, 348) are configured to bear against an exterior surface of sleeve portion (106) of transducer assembly (100) when instrument (300) is completely assembled. FIGS. 17A-17C show the interaction of resilient tabs (347, 348) with sleeve portion (106) of transducer assembly (100) during the coupling of shaft assembly (310) with transducer assembly. It should be understood that the stages shown in FIGS. 17A-17C would be occurring between the stage shown in FIG. 14F and the stage shown in FIG. 14G.

FIG. 17A shows shaft assembly (310) in an initial stage of engagement with transducer assembly (100). In particular, threaded stud (122) of horn (120) has been partially threaded into threaded bore (322) of waveguide (320) in response to the user rotating shaft assembly (310) relative to transducer assembly (100). At this stage, sheath (230), connector (260), torque member (250), waveguide (320), and retaining member (360) are all at a distal position relative to shroud halves (340, 342). As can also be seen in FIG. 17A, flange (261) is at a distal position in relation to resilient tabs (347, 348) of shroud halves (340, 342), such that resilient tabs (347, 348) are both at inwardly deflected orientations. In the present example, the proximal edges of resilient tabs (347, 348) abut the distal annular edge of sleeve portion (106) of transducer assembly (100) at this stage.

As the user continues to rotate shaft assembly (310) relative to transducer assembly (100), the engagement between threaded stud (122) and threaded bore (322) continues to draw the combination of sheath (230), connector (260), torque member (250), waveguide (320), and retaining member (360) proximally toward transducer assembly (100). However, shroud halves (340, 342) do not translate proximally, yet, due to engagement between the proximal edges of resilient tabs (347, 348) abut the distal annular edge of sleeve portion (106). The combination of sheath (230), connector (260), torque member (250), waveguide (320), and retaining member (360) thus translates proximally relative to shroud halves (340, 342) in addition to translating proximally relative to transducer assembly (100) at this stage. While the combination of sheath (230), connector (260), torque member (250), waveguide (320), and retaining member (360) translates proximally relative to shroud halves (340, 342), retaining member (360) compresses spring (370) against flanges (362, 364). As connector (260) translates proximally with the combination of sheath (230), torque member (250), waveguide (320), and retaining member (360) relative to shroud halves (340, 342), flange (261) bears outwardly against resilient tabs (347, 348), such that flange (261) eventually drives resilient tabs (347, 348) outwardly as shown in FIG. 17B. In particular, flange (261) drives resilient tabs (347, 348) outwardly to a point where resilient tabs (347, 348) are oriented substantially parallel to the longitudinal axis of instrument (300), such that resilient tabs (347, 348) are oriented to fit in a gap defined between the outer diameter of sleeve portion (106) and the inner diameter of retaining sleeve (346).

Once flange (261) has driven resilient tabs (347, 348) outwardly to a point where resilient tabs (347, 348) are oriented to fit in the gap defined between the outer diameter of sleeve portion (106) and the inner diameter of retaining sleeve (346), the proximal resilient bias imposed by spring (370) drives shroud halves (340, 342) proximally toward transducer assembly (100) as shown in FIG. 17C. At this stage, shroud halves (340, 342) and the combination of sheath (230), connector (260), torque member (250), waveguide (320), and retaining member (360) are in proximal positions relative to transducer assembly. The user may continue to rotate shaft assembly (310) relative to transducer assembly (100) in order to achieve the appropriate amount of torque, as regulated by torque member (250). In some versions, instrument (300) is configured such that shroud halves (340, 342) snap back from the distal position of FIG. 17B to the proximal position of FIG. 17C as soon as an appropriate amount of torque is achieved in the coupling of horn (120) with waveguide (320). In some other versions, instrument (300) is configured such that shroud halves (340, 342) snap back from the distal position of FIG. 17B to the proximal position of FIG. 17C just before an appropriate amount of torque is achieved in the coupling of horn (120) with waveguide (320). Thus, the snapping back of shroud halves (340, 342) may further indicate to the user that the appropriate amount of torque has been achieved or will soon be achieved.

C. Exemplary Integral Torque Assembly with Sliding Grip

FIGS. 18-22C show another exemplary instrument (400) having an integral torque assembly (450). Instrument (400) of the present example is configured to operate substantially similar to instruments (10, 200, 300) discussed above except for the differences discussed below. Instrument (400) is thus operable to transect and/or seal tissue at a surgical site. Furthermore, torque assembly (450) is configured to operate substantially similar to the torque assemblies that include torque members (250, 350) discussed above, except for the differences discussed below. In particular, torque assembly (450) is configured to limit the amount of torque that may be applied to couple a waveguide (420) with transducer assembly (100); and provide audible/tactile feedback to indicate that the appropriate amount of torque has been achieved.

Figure 19:
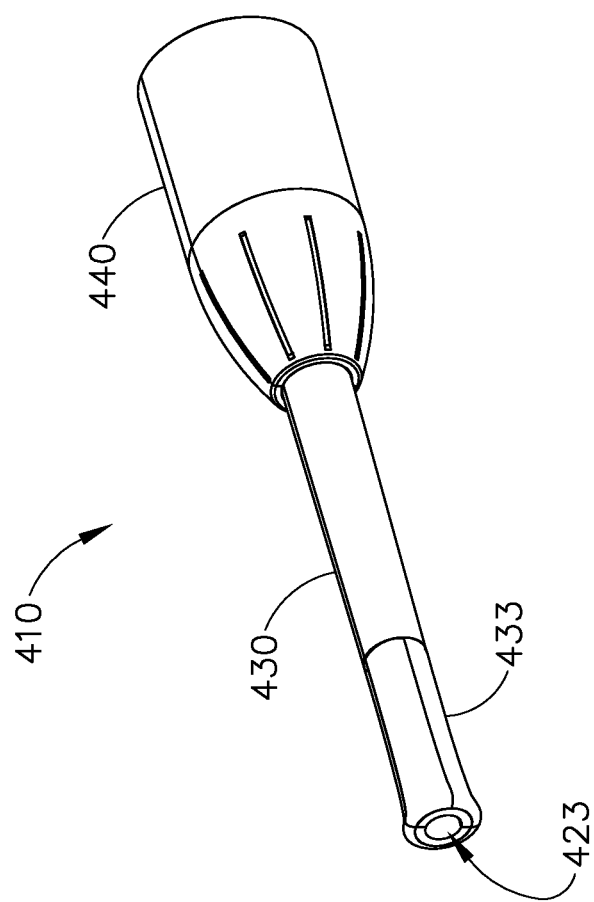
FIG. 19 depicts a perspective view of an exemplary sheath assembly of the instrument of FIG. 18.
Figure 20:
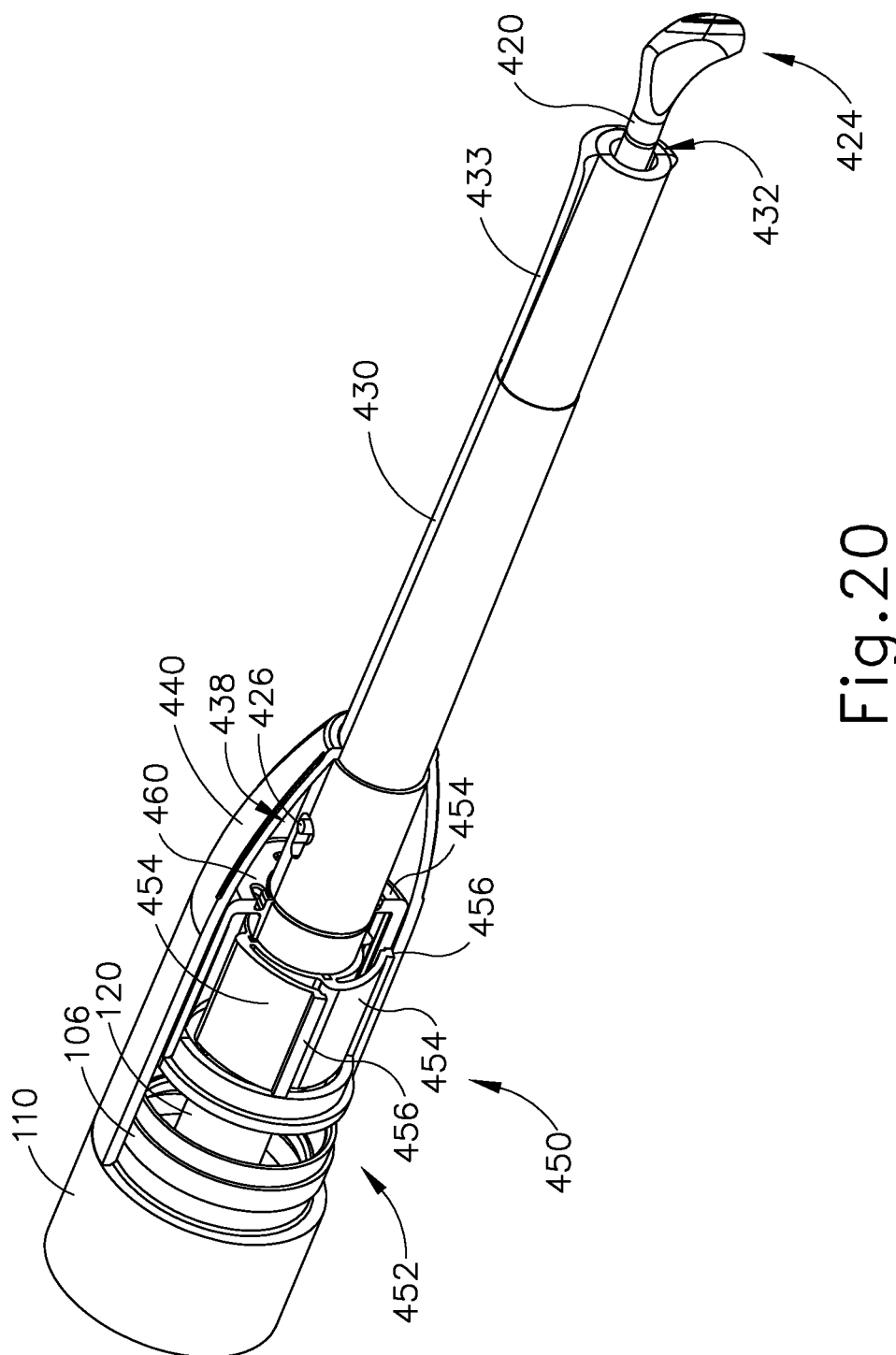
FIG. 20 depicts a partial perspective view of the instrument of FIG. 18, with a portion of the sheath assembly omitted.
Figure 21:
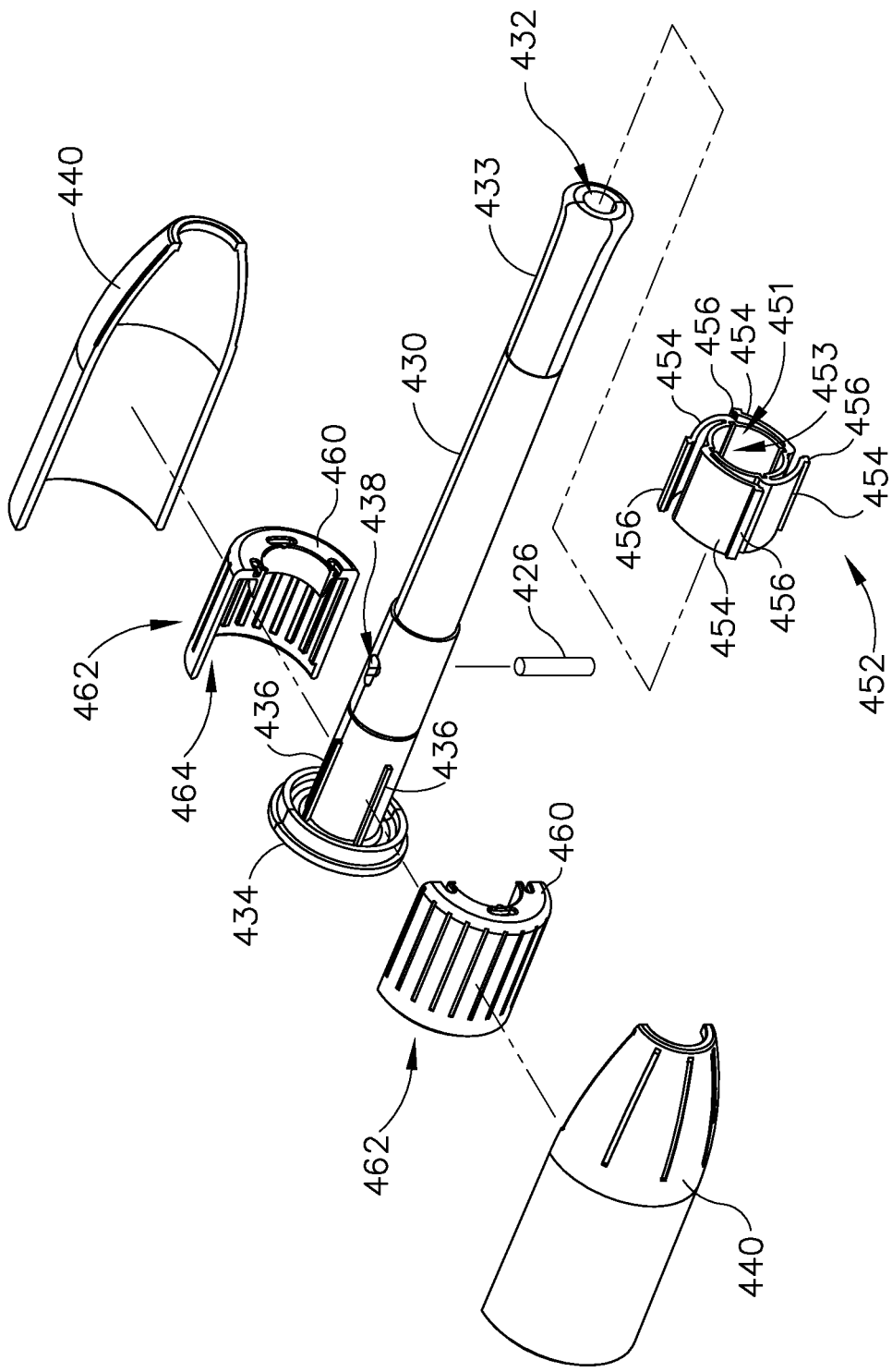
FIG. 21 depicts an exploded perspective view of the sheath assembly of FIG. 19.

Instrument (400) of the present example comprises transducer assembly (100) and a shaft assembly (410). Shaft assembly (410) comprises a waveguide (420), a sheath (430), a shroud (440), and a torque assembly (450). As shown in FIG. 19, sheath (430) defines a longitudinal interior bore (432) that passes completely through sheath (430) from a proximal end to a distal end thus defining a proximal opening and a distal opening. Sheath (430) is configured to receive waveguide (420) within interior bore (432). A pin (426) is passed through waveguide (420) and an elongate slot (438) formed in sheath (430) to thereby couple sheath (430) and waveguide (420) such that rotation of sheath (430) causes concurrent rotation of waveguide (420). Pin (426) is located at a position along the length of waveguide (420) corresponding to a node associated with resonant ultrasonic vibrations communicated through waveguide (420). It should be understood that elongate slot (438) may allow for some longitudinal translation of waveguide (420) and pin (426) relative to sheath (430). Shaft assembly (410) also includes a user input feature (411) that is operable to selectively activate transducer assembly (100), to thereby selectively activate ultrasonic blade (424) of waveguide (420). User input feature (411) may be constructed and operable in accordance with the teachings herein relating to user input feature (211) of instrument (200).

A proximal end of sheath (430) includes an annular flange (434) and a plurality of longitudinal projections (436) extending outwardly from an exterior surface of sheath (430). Torque assembly (450) comprises a ratcheting pawl (452) and a ratcheting collar (460). Ractcheting pawl (452) defines a longitudinal interior bore (451) that passes completely through ractcheting pawl (452) from a proximal end to a distal end thus defining a proximal opening and a distal opening. Interior bore (451) of ractcheting pawl (452) is configured to receive sheath (430) such that a proximal surface of ratcheting pawl (452) rests against a distal surface of flange (434). A plurality of longitudinal channels (453) are formed in the interior surface of interior bore (451) of ratcheting pawl (452). Longitudinal channels (453) are configured to receive longitudinal projections (436) such that rotation of ratcheting pawl (452) causes concurrent rotation of sheath (430). Ratcheting pawl (452) includes a plurality of resilient members (454) extending from an exterior surface of ratcheting pawl (452). Each resilient member (454) includes an outwardly extending tab (456).

An exterior surface of ratcheting collar (460) presents a plurality of inwardly directed and longitudinally extending recesses (462). An interior surface of shroud (440) presents a plurality of inwardly directed and longitudinally extending projections (not shown). Shroud (440) is configured to receive ratcheting collar (460) such that the projections of shroud (440) engage recesses (462). Thus, due to this engagement, rotation of shroud (440) causes concurrent rotation of collar (460). An interior surface of collar (460) presents a plurality of inwardly directed and longitudinally extending projections (464). Projections (464) are configured to engage tabs (456) of pawl (452) such that shroud (440) may be used to rotate and sheath (430) and waveguide (420) relative to transducer assembly (100). Resilient members (454) are further configured to provide slipping of tabs (456) relative to projections (464) to thereby effectively limit the amount of torque that may be applied to waveguide (420) by shroud (440) and collar (460).

Figure 22A:
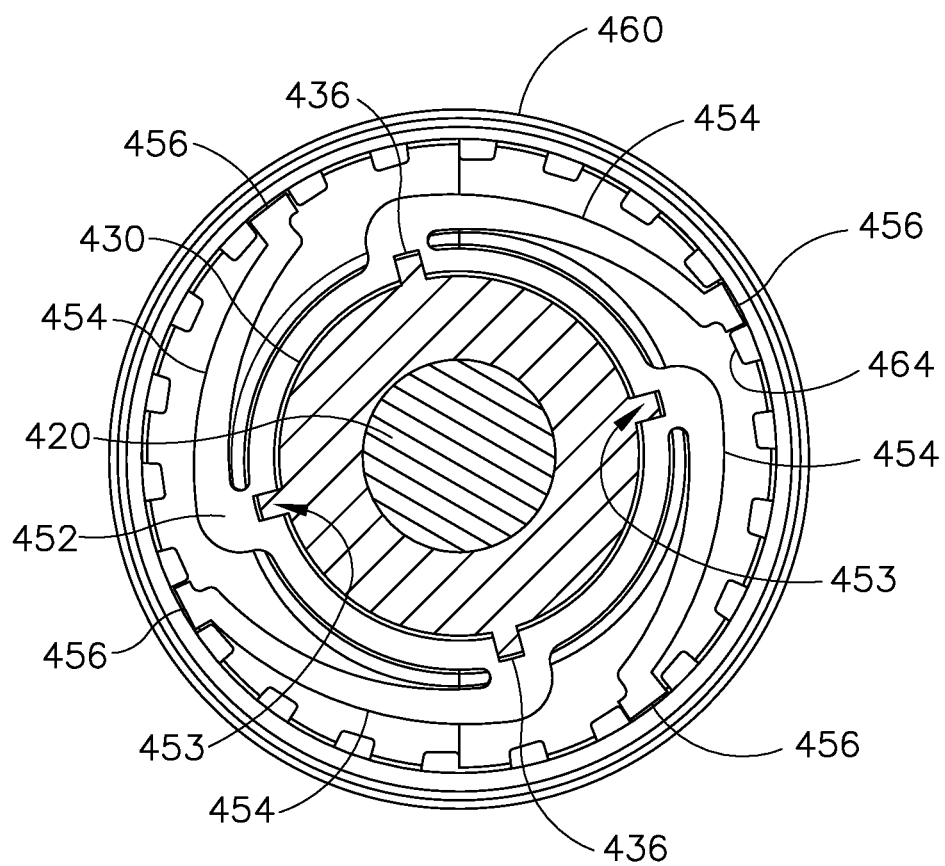
FIG. 22A depicts a cross-sectional view of the ratcheting assembly of the instrument of FIG. 18, with a inner radial member in a first rotational position.
Figure 22B:
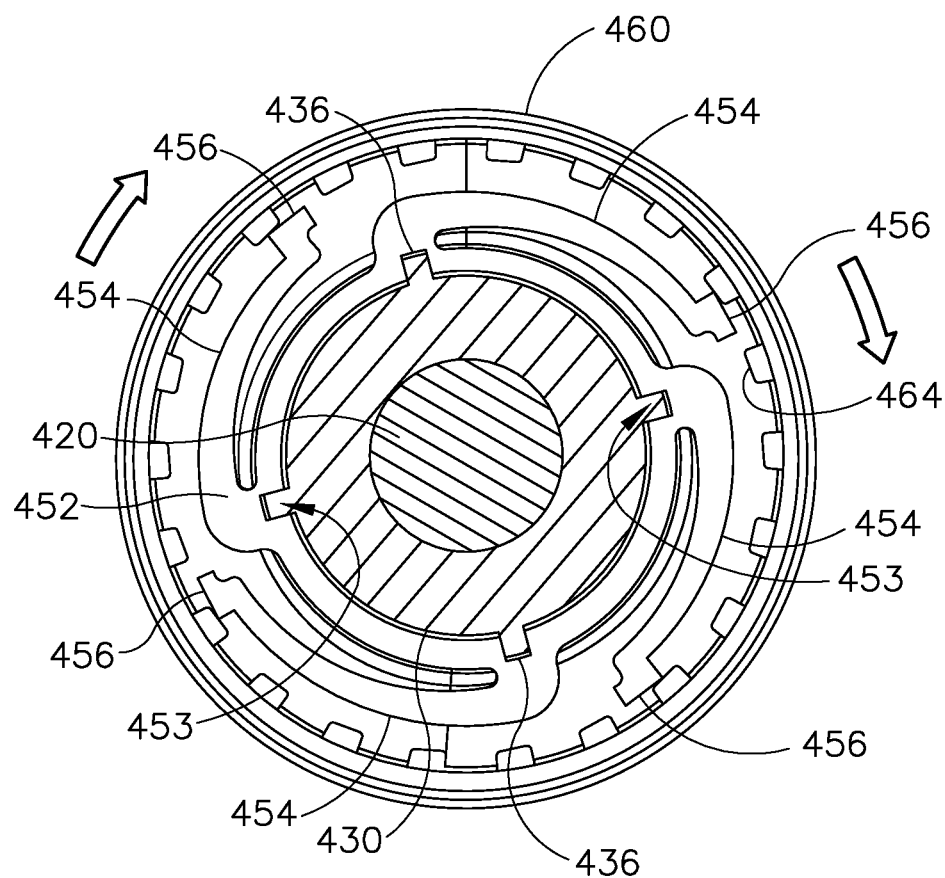
FIG. 22B depicts a cross-sectional view of the ratcheting assembly of the instrument of FIG. 18, with the inner radial member in a second rotational position.
Figure 22C:
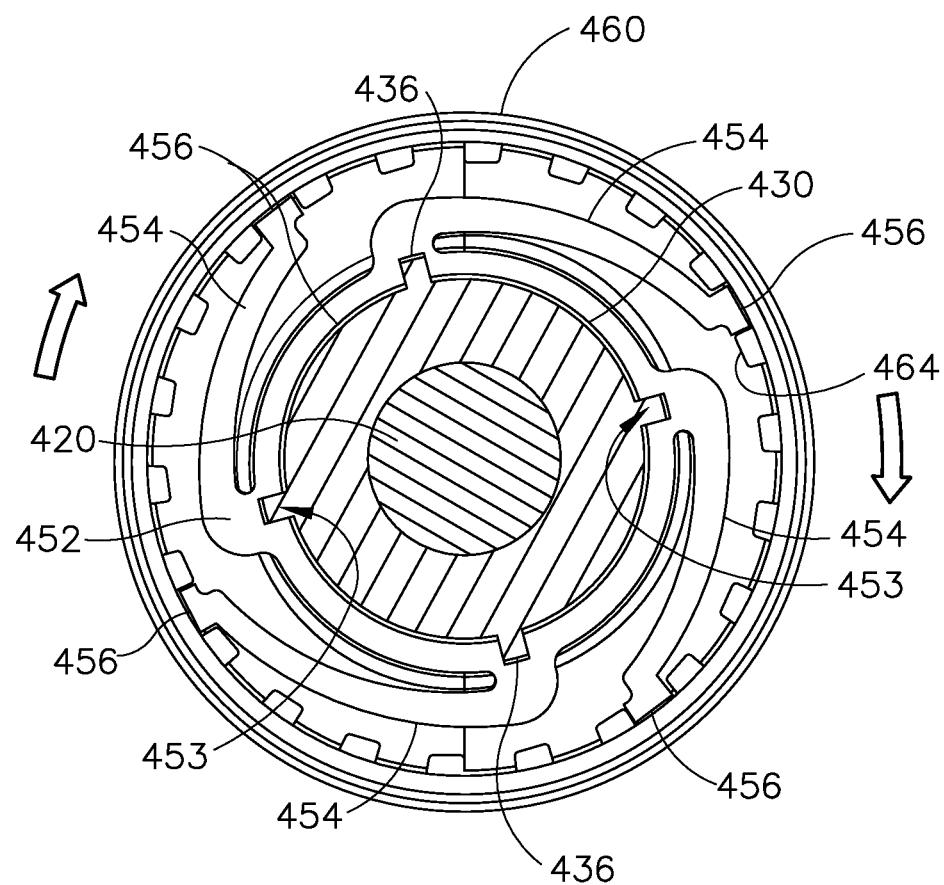
FIG. 22C depicts a cross-sectional view of the ratcheting assembly of the instrument of FIG. 18, with the inner radial member in a third rotational position.
Figure 23:
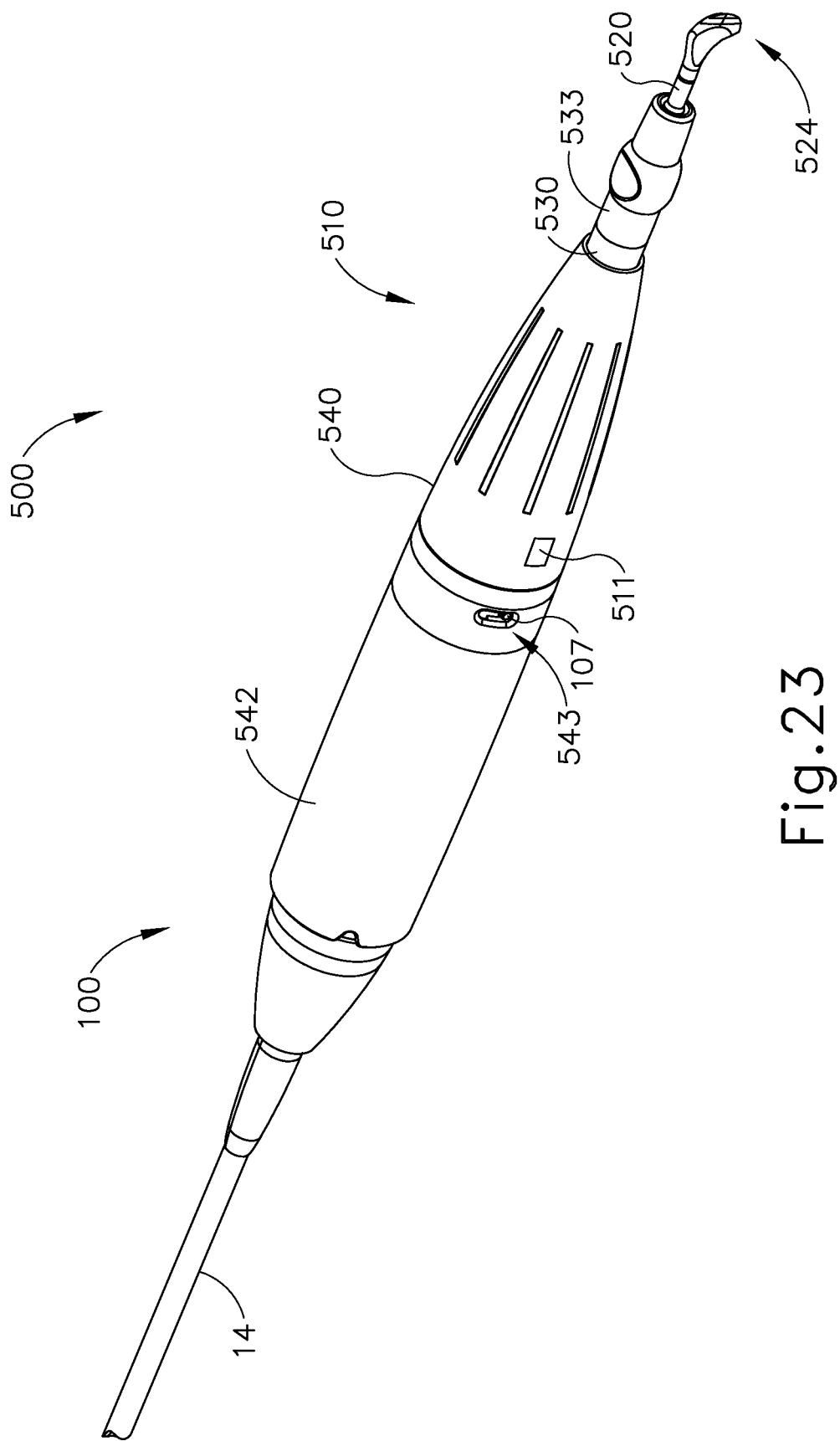
FIG. 23 depicts a perspective view of yet another exemplary alternative surgical instrument.

FIGS. 22A-22C show the interaction of pawl (452) and collar (460) as waveguide (420) is connected with transducer assembly (100). As shroud (440) is rotated clockwise, ratcheting collar (460) rotates as well because of the engagement between the longitudinal projections of shroud (440) and corresponding longitudinal channels (462) of collar (460). As collar (460) rotates clockwise, tabs (456) of ratcheting pawl (452) contact longitudinal projections (464) of ratcheting pawl (460) as shown in FIG. 22A. With tabs (456) engaging projections (464), the user continues to rotate shroud (440) and collar (460) clockwise relative to transducer assembly (100) through a first range of motion. During this first range of motion, tabs (456) continue to engage projections (464) such that torque assembly (450) rotates sheath (430) and waveguide (420) relative to transducer assembly (100). Waveguide (420) is thereby coupled with threaded stud (122).

As the user completes the first range of motion, waveguide (420) is secured to threaded stud (122) with a certain predetermined amount of torque. Once the assembly of waveguide (420) and threaded stud (122) reaches the predetermined amount of torque, and the user continues to rotate shroud (440) and collar (460) clockwise relative to transducer assembly (100) past the first range of motion, resilient members (454) deflect inwardly as shown in FIG. 22B. In particular, projections (464) drive tabs (456) inwardly through a cam action, such that collar (460) no longer rotates pawl (452). Sheath (430) and waveguide (420) thus remain rotationally stationary at this stage. As the user continues to rotate shroud (400), collar (460) continues to rotate such that tabs (456) eventually clear projections (464) and snap outwardly as shown in FIG. 22C. This outward snapping/ratcheting may provide audible and/or tactile feedback to indicate to the user that an appropriate amount of torque has been achieved in the coupling of waveguide (420) with threaded stud (122). It should be understood that from this point on, any further clockwise rotation of shroud (440) and collar (460) no longer causes rotation of the combination of pawl (452), sheath (430), and waveguide (420) relative to transducer assembly (100). It should also be understood that the rigidity of resilient members (454) may be changed to thereby change the maximum amount of torque that may be applied to waveguide (420).

As noted above, the integral torque assembly features of shaft assembly (410) eliminate the need for a separate torque wrench (e.g., such as torque wrench (50), etc.) to secure waveguide (420) with horn (120). It should also be understood that, during use of assembled instrument (400), the distal portion of sheath (430) proximal to ultrasonic blade (424) may be grasped by a user during operation to grasp instrument (400) in a pencil-like manner. Holding instrument (400) with a pencil grip may enable the user to provide very fine and precise movement with blade (424), such as in a facial plastic surgery procedure or some other fine and precise surgical procedure. In the present example, the distal portion of sheath (430) of comprises an ergonomic overmold (433) that further facilitates a pencil grip. Other suitable features will be apparent to those of ordinary skill in the art in view of the teachings herein.

In some versions of instrument (400), shroud (440) may translate longitudinally relative to sheath (430). In some such versions, a resilient member may be used to resiliently bias shroud (440) relative to sheath (430) (e.g., similar to spring (370), etc.). In addition or in the alternative, sheath (430) may be resiliently biased relative to transducer assembly (100). It should also be understood that the proximal end of shroud (440) may be configured to threadably couple with sleeve portion (106) of transducer assembly (100). Furthermore, a foam filler, spring, and/or other feature may be positioned between shroud (440) and sheath (430) to substantially maintain a spatial relationship between shroud (440) and sheath (430) along transverse paths.

D. Exemplary Integral Torque Assembly with Bayonet Mount

FIGS. 23-27C show another exemplary instrument (500) having an integral torque assembly (550). Instrument (500) of the present example is configured to operate substantially similar to instruments (10, 200, 300, 400) discussed above except for the differences discussed below. Instrument (500) is thus operable to transect and/or seal tissue at a surgical site. Furthermore, torque assembly (550) is configured to operate substantially similar to the torque assemblies that included torque members (250, 350) and torque assembly (450) discussed above, except for the differences discussed below. In particular, torque assembly (550) is configured to limit the amount of torque that may be applied to couple a waveguide (520) with transducer assembly (100); and provide audible/tactile feedback to indicate that the appropriate amount of torque has been achieved.

Instrument (500) of the present example comprises transducer assembly (100) and a shaft assembly (510). Shaft assembly (510) comprises a waveguide (520), a sheath (530), a shroud (540), and a locking cylinder (542). Shaft assembly (510) also includes a user input feature (511) that is operable to selectively activate transducer assembly (100), to thereby selectively activate ultrasonic blade (524) of waveguide (520). User input feature (511) may be constructed and operable in accordance with the teachings herein relating to user input feature (211) of instrument (200). A distal end of locking cylinder (542) is rotatably coupled with a proximal end of shroud (540) such that shroud (540) is rotatable relative to locking cylinder (542). Locking cylinder (542) comprises a longitudinal channel (541) formed in an interior surface of locking cylinder (542). Longitudinal channel (541) extends longitudinally distally from a proximal end of locking cylinder (542) to a lateral opening (543) formed through locking cylinder (542). Sleeve portion (106) of transducer assembly (100) of the present example comprises a pin (107) extending outwardly from the exterior surface of sleeve portion (106).

Figure 24A:
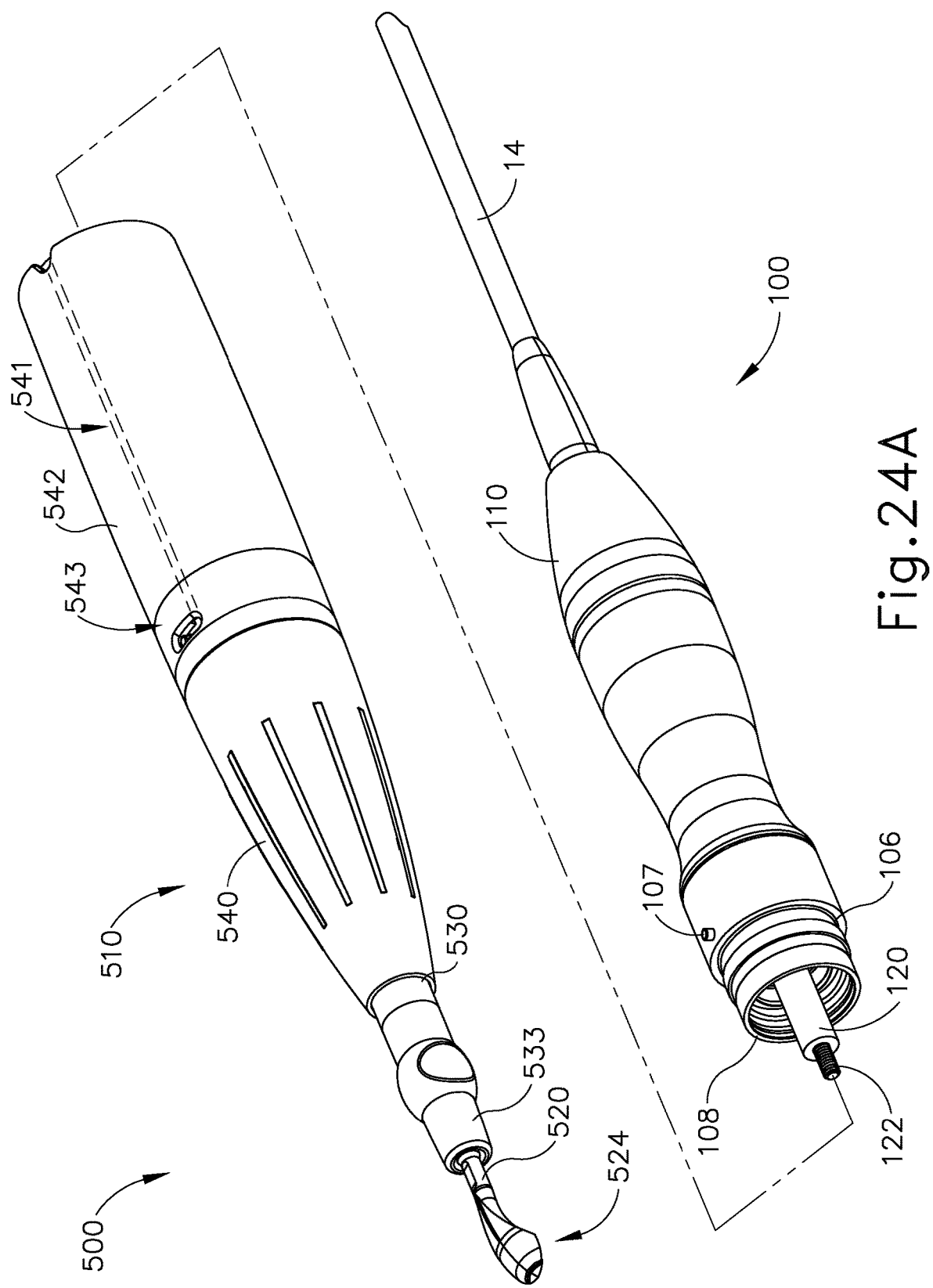
FIG. 24A depicts an exploded perspective view of the instrument of FIG. 23, showing the instrument in a disassembled state.
Figure 24B:
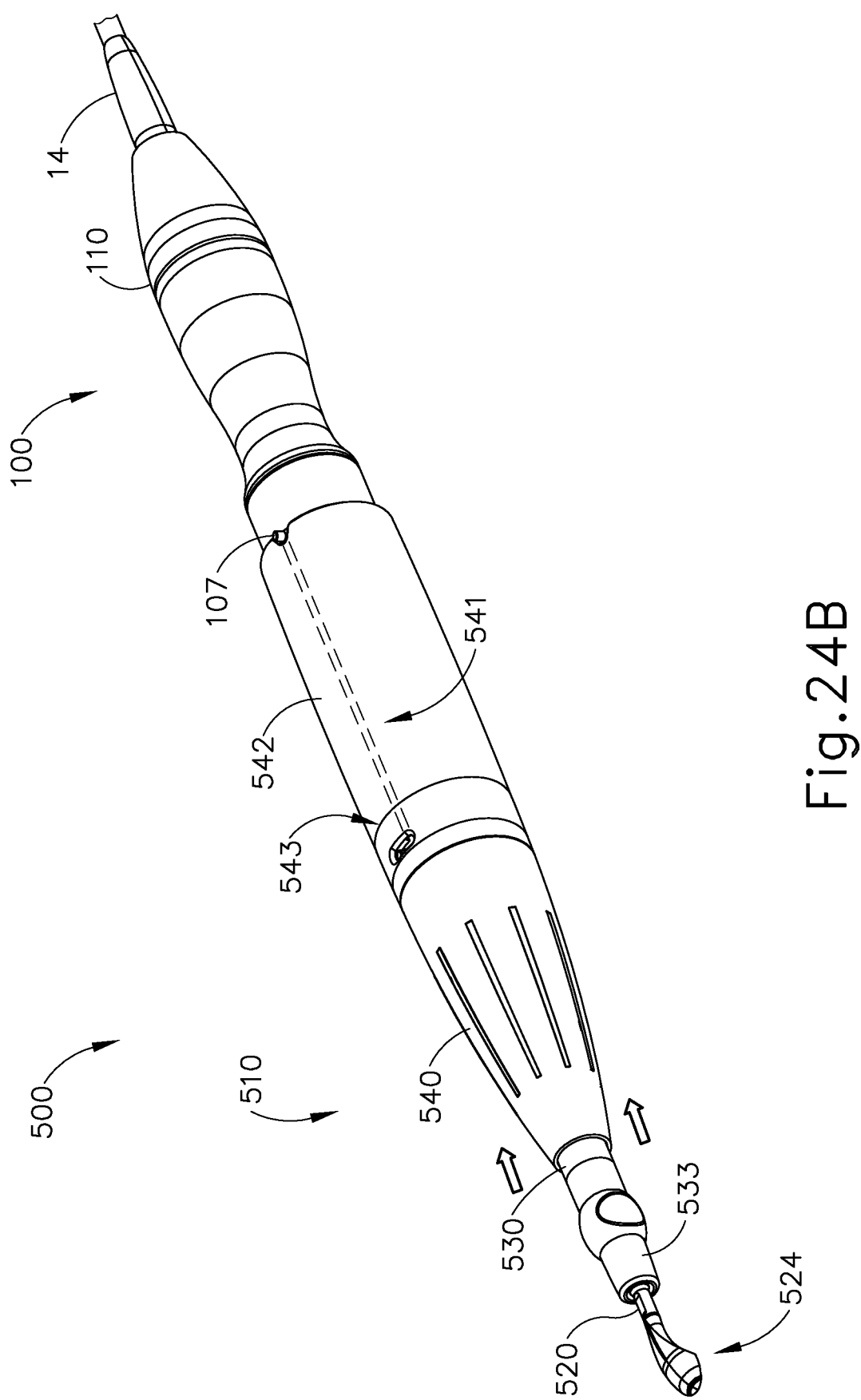
FIG. 24B depicts a perspective view of the instrument of FIG. 23, showing the instrument in a partially assembled state.
Figure 24C:
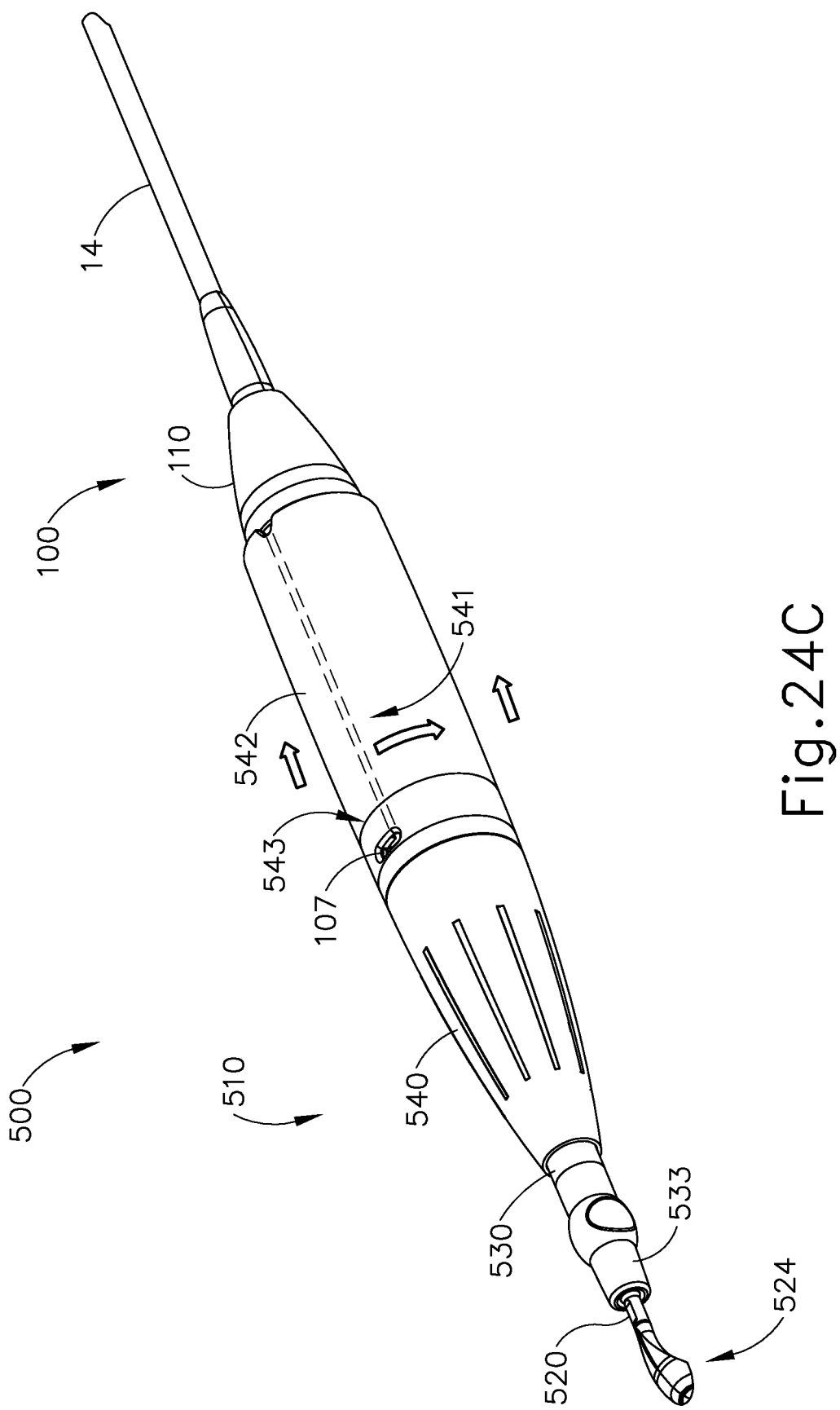
FIG. 24C depicts a perspective view of the instrument of FIG. 23, showing the instrument in an assembled state.

Longitudinal channel (541) is configured to receive pin (107) as transducer assembly (100) is passed longitudinally into locking cylinder (542) as shown in FIGS. 24A-24C. Once pin (107) reaches lateral opening (543), locking cylinder (542) is rotated clockwise relative to transducer assembly (100) such that pin (107) becomes positioned within lateral opening (546), which extends laterally in relation to channel (541), as shown in FIG. 24C. It should therefore be understood that locking cylinder (542) is coupled with transducer assembly (100) in a bayonet-like manner. This coupling prevents shaft assembly (510) from sliding distally off of transducer assembly (100), though sheath (530), waveguide (520), and shroud (540) are still rotatable relative to transducer assembly (100) at this stage. It should further be understood that any further rotation of shroud (540) relative to transducer assembly (100) will not be communicated to locking member (542) because of contact between pin (107) and an interior surface of lateral opening (543).

Figure 25:
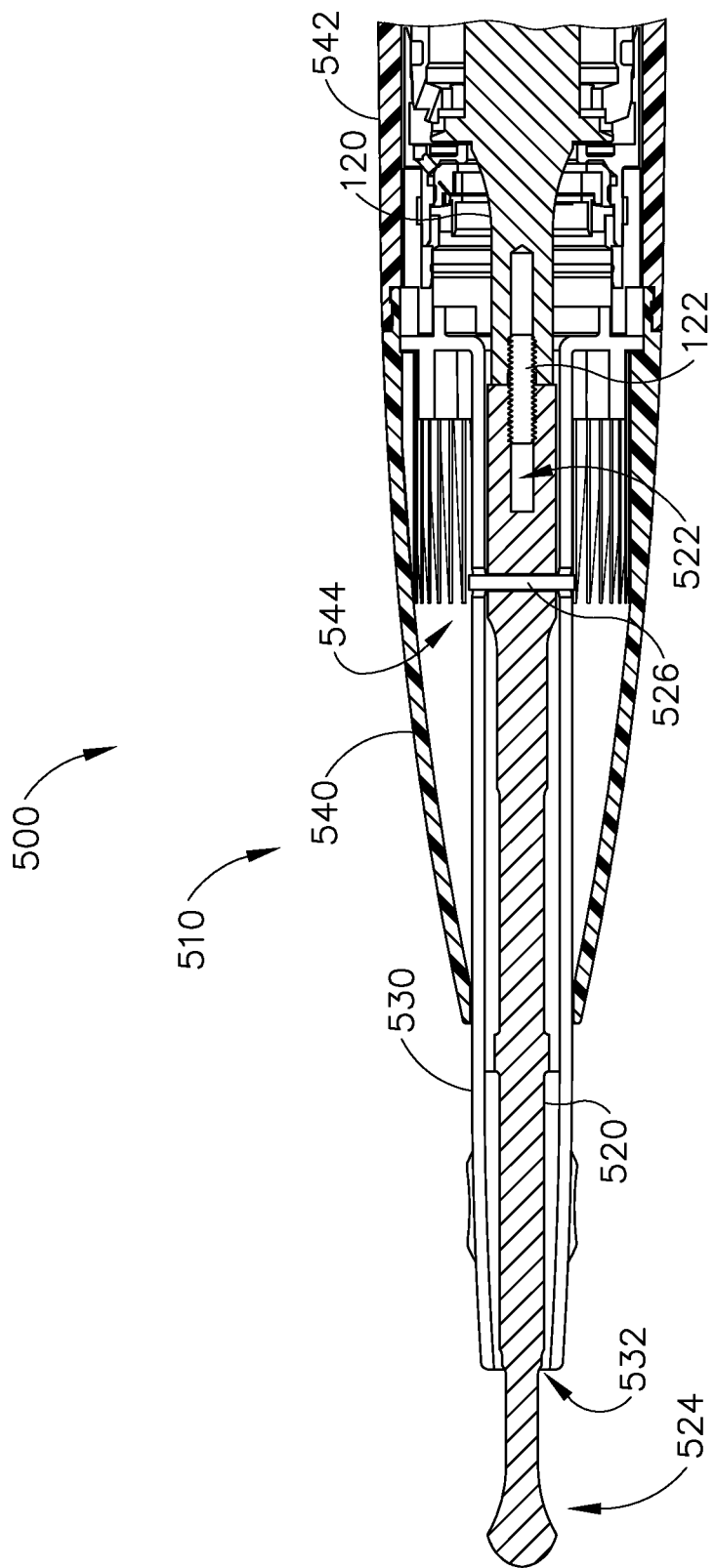
FIG. 25 depicts a partial cross-sectional view of the instrument of FIG. 23.

As shown in FIG. 25, sheath (530) defines a longitudinal interior bore (532) that passes completely through sheath (530) from a proximal end to a distal end thus defining a proximal opening and a distal opening. Sheath (530) is configured to receive waveguide (520) within interior bore (532). A pin (526) is passed through waveguide (520) and sheath (530) to thereby couple sheath (530) and waveguide (520) such that rotation of sheath (530) causes concurrent rotation of waveguide (520). Pin (526) is located at a position along the length of waveguide (520) corresponding to a node associated with resonant ultrasonic vibrations communicated through waveguide (520).

Figure 26:
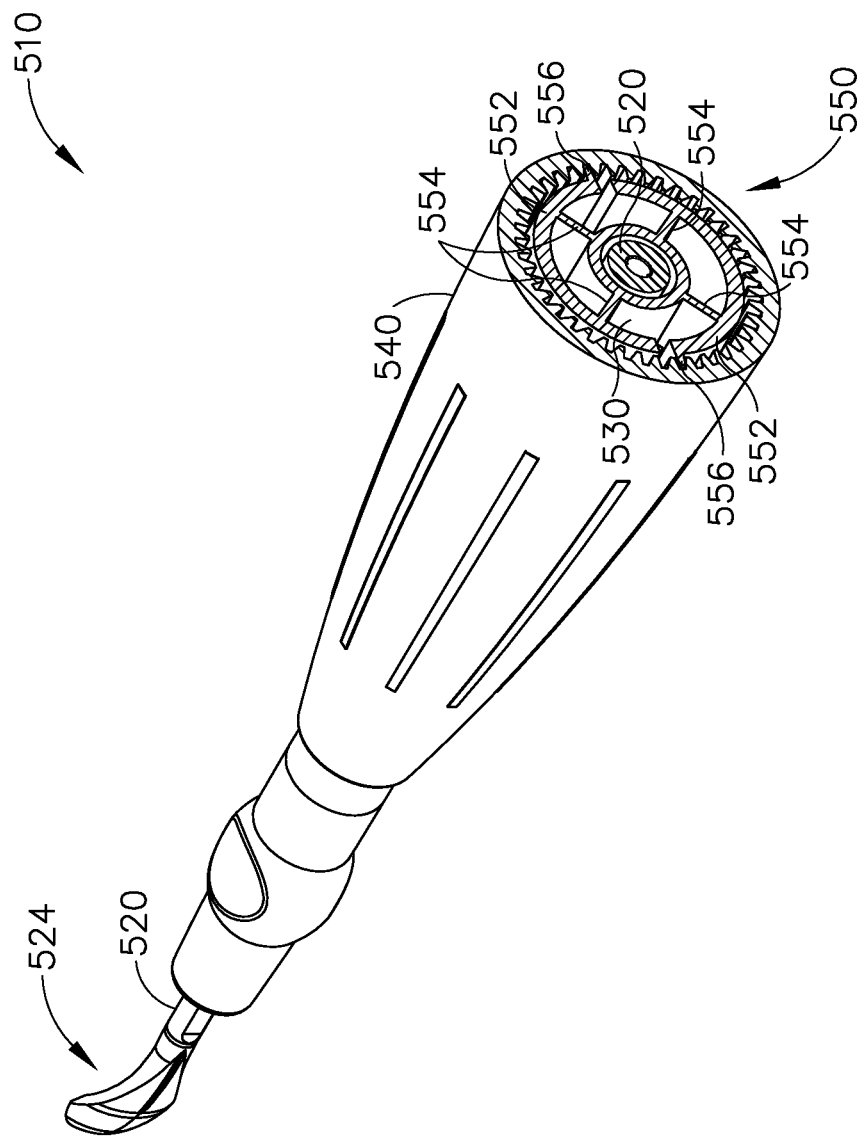
FIG. 26 depicts a perspective view of the shroud assembly of the instrument of FIG. 23.

As best seen in FIG. 26, a proximal end of sheath (530) includes a torque assembly (550). Torque assembly (550) comprises a pair of semi-circular resilient members (552) coupled to an exterior surface of sheath (530) via a respective pair of radially extending projections (554). Each resilient member (552) includes an outwardly extending tab (556). Shroud (540) comprises a plurality of inwardly extending longitudinal projections (542) disposed in an angular array about an interior surface of shroud (540). Longitudinal projections (542) are configured to engage tabs (556) of resilient members (552) such that shroud (540) may be used to rotate and sheath (530) and waveguide (520) relative to transducer assembly (100). Resilient members (552) are further configured to provide slipping of tabs (556) relative to projections (542) to thereby effectively limit the amount of torque that may be applied to waveguide (520) by shroud (540).

Figure 27A:
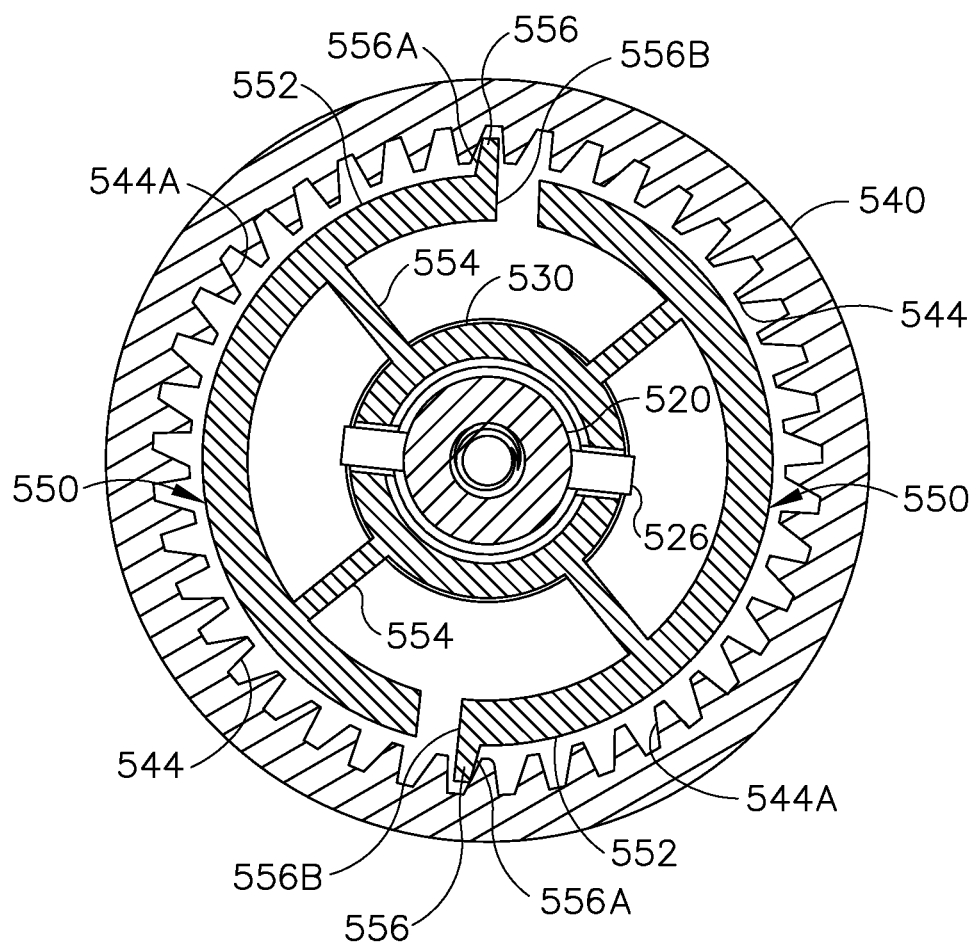
FIG. 27A depicts a cross-sectional view of the ratcheting assembly of the instrument of FIG. 23, with an inner radial member in a first rotational position.
Figure 27B:
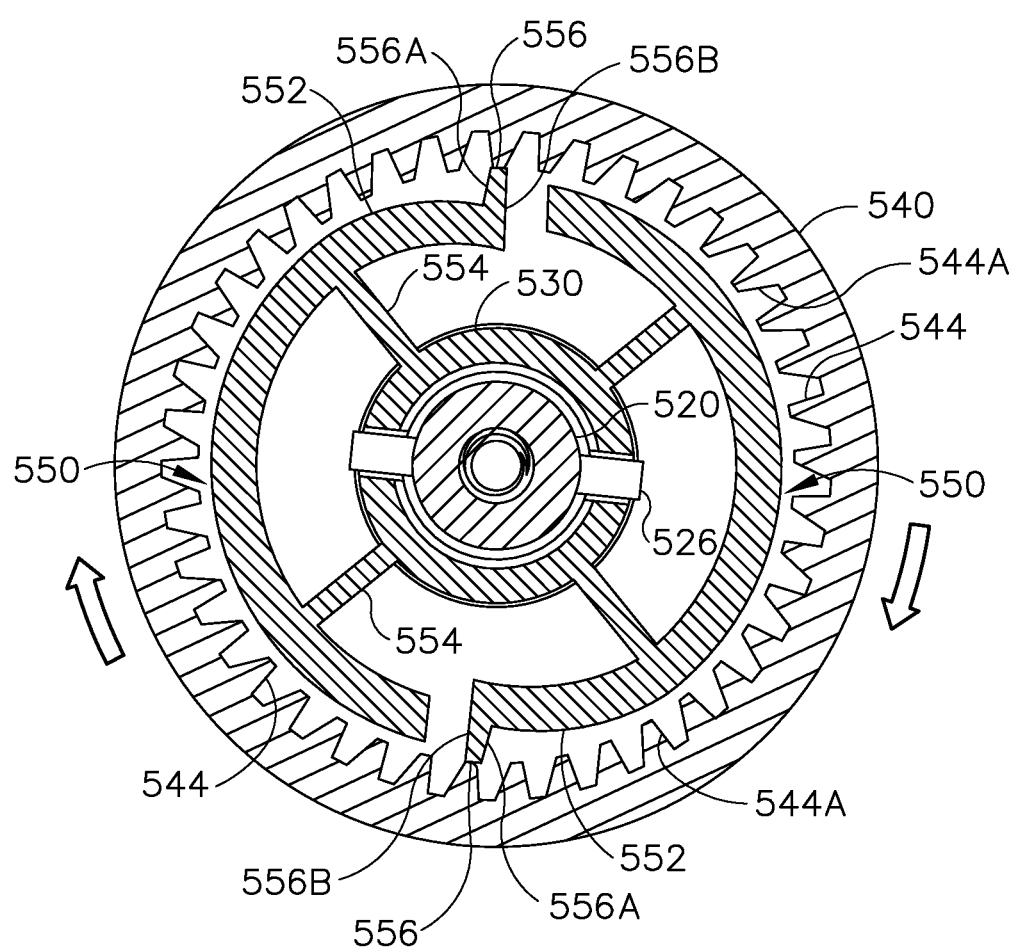
FIG. 27B depicts a cross-sectional view of the ratcheting assembly of FIG. 27A, with the inner radial member rotated into a second rotational position.
Figure 27C:
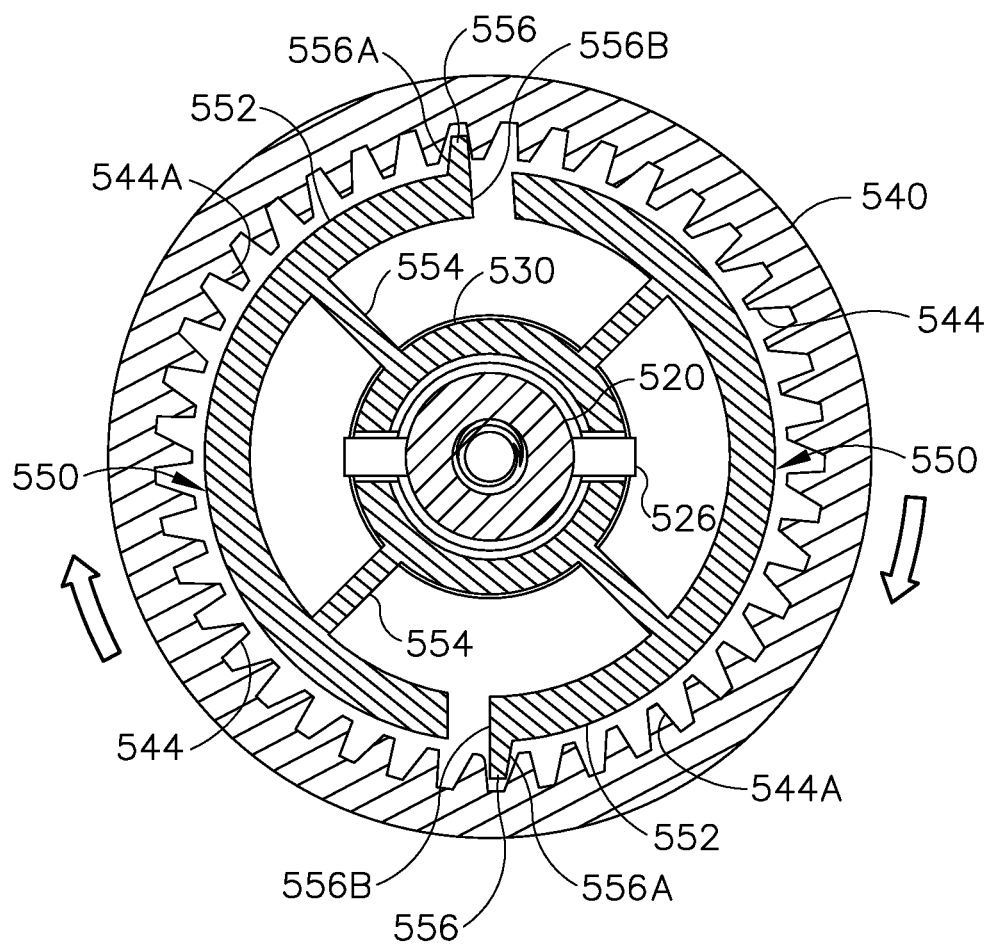
FIG. 27C depicts a cross-sectional view of the ratcheting assembly of FIG. 27A, with the inner radial member rotated into a third rotational position.

FIGS. 27A-27C show the interaction of resilient members (552) and shroud (540) as waveguide (520) is connected with transducer assembly (100). As shroud (540) is rotated clockwise, tabs (556) of resilient members (552) contact longitudinal projections (544) of shroud (540) as shown in FIG. 27A. Thus, as shroud (540) is rotated clockwise relative to transducer assembly (100), projections (544) and tabs (556) cooperate to drive sheath (530) clockwise, thereby rotating waveguide (520) clockwise relative to transducer assembly (100) through a first range of motion. During this first range of motion, tabs (556) continue to engage projections (544) such that torque assembly (550) rotates sheath (530) and waveguide (520) relative to transducer assembly (100). Waveguide (520) is thereby coupled with threaded stud (122).

As the user completes the first range of motion, waveguide (520) is secured to threaded stud (122) with a certain predetermined amount of torque. Once the assembly of waveguide (520) and threaded stud (122) reaches the predetermined amount of torque, and the user continues to rotate shroud (540) clockwise relative to transducer assembly (100) past the first range of motion, resilient members (552) deflect inwardly as shown in FIG. 27B. In particular, projections (544) drive tabs (556) inwardly through a cam action, such that shroud (540) no longer rotates sheath (530). Sheath (530) and waveguide (520) thus remain rotationally stationary at this stage. As the user continues to rotate shroud (540), tabs (556) eventually clear projections (544) and snap outwardly as shown in FIG. 27C. This outward snapping/ratcheting may provide audible and/or tactile feedback to indicate to the user that an appropriate amount of torque has been achieved in the coupling of waveguide (520) with threaded stud (122). It should be understood that from this point on, any further clockwise rotation of shroud (540) no longer causes rotation of sheath (530) and waveguide (530) relative to transducer assembly (100). It should also be understood that the rigidity of resilient members (552) may be changed to thereby change the maximum amount of torque that may be applied to waveguide (520).

A surface (556B) of each tab (556) is substantially flat such that as shroud (540) is rotated counterclockwise relative to transducer assembly (100), contact between longitudinal projections (544) and tabs (556) will not drive resilient members (552) inwardly. It should therefore be understood that rotation of shroud (540) relative to transducer assembly (100) in a counterclockwise motion will not cause slipping or ratcheting of torque assembly (550). Thus, when the user wishes to disassemble shaft assembly (510) from transducer assembly (100) at the end of a surgical procedure, the user may simply grasp shroud (540) with one hand and rotate shroud (540) counterclockwise relative to transducer assembly (100) while gripping transducer assembly (100) with the other hand, until waveguide (520) is decoupled from threaded stud (122) of transducer assembly (100). The user may then rotate locking cylinder (542) relative to transducer assembly to disengage pin (107) from lateral opening (546), then simply pull shaft assembly (510) away from transducer assembly (100). At this stage, shaft assembly (510) may be disposed of; while transducer assembly (100) may be reconditioned any re-used. Alternatively, the user may wish to handle these components in some other fashion.

As noted above, the integral torque assembly features of shaft assembly (510) eliminate the need for a separate torque wrench (e.g., such as torque wrench (50), etc.) to secure waveguide (520) with horn (120). It should also be understood that, during use of assembled instrument (500), the distal portion of sheath (530) proximal to ultrasonic blade (524) may be grasped by a user during operation to grasp instrument (500) in a pencil-like manner. Holding instrument (500) with a pencil grip may enable the user to provide very fine and precise movement with blade (524), such as in a facial plastic surgery procedure or some other fine and precise surgical procedure. In the present example, the distal portion of sheath (530) of comprises an ergonomic overmold (533) that further facilitates a pencil grip. Other suitable features will be apparent to those of ordinary skill in the art in view of the teachings herein.

E. Exemplary Integral Torque Assembly with Slip Ring

FIGS. 28-31 show another exemplary instrument (600) having an integral torque assembly (650). Instrument (600) of the present example is configured to operate substantially similar to instruments (10, 200, 300, 400, 500) discussed above except for the differences discussed below. Instrument (600) is thus operable to transect and/or seal the tissue at a surgical site. Furthermore, torque assembly (650) is configured to operate substantially similar to the torque assemblies that included torque members (250, 350), and torque assemblies (450, 550) discussed above except for the differences discussed below. In particular, torque assembly (650) is configured to limit the amount of torque that may be applied to couple a waveguide (620) with transducer assembly (100); and provide audible/tactile feedback to indicate that the appropriate amount of torque has been achieved.

Instrument (600) of the present example comprises transducer assembly (100) and a shaft assembly (610). Shaft assembly (610) comprises a waveguide (620), a sheath (630), a shroud (640), and an outer cuff (642). Shaft assembly (610) also includes a user input feature (611) that is operable to selectively activate transducer assembly (100), to thereby selectively activate ultrasonic blade (624) of waveguide (620). User input feature (611) may be constructed and operable in accordance with the teachings herein relating to user input feature (211) of instrument (200). A distal end of outer cuff (642) comprises a plurality of rectangular projections (643). A proximal end of shroud (640) presents a plurality of longitudinal channels (641) configured to receive rectangular projections (643) such that outer cuff (642) and shroud (640) rotate together. The interior of outer cuff (642) includes a threading (not shown) that is configured to complement an exterior threading on sleeve portion (106) of transducer assembly (100). Outer cuff (642) may thus be threadably coupled with sleeve portion (106). In the present example, as an initial stage of securing shaft assembly (610) to transducer assembly (100), the user first begins threading outer cuff (642) onto sleeve portion (106). This will provide alignment and seating of waveguide (620) with threaded stud (122) of horn (120).

Figure 30:
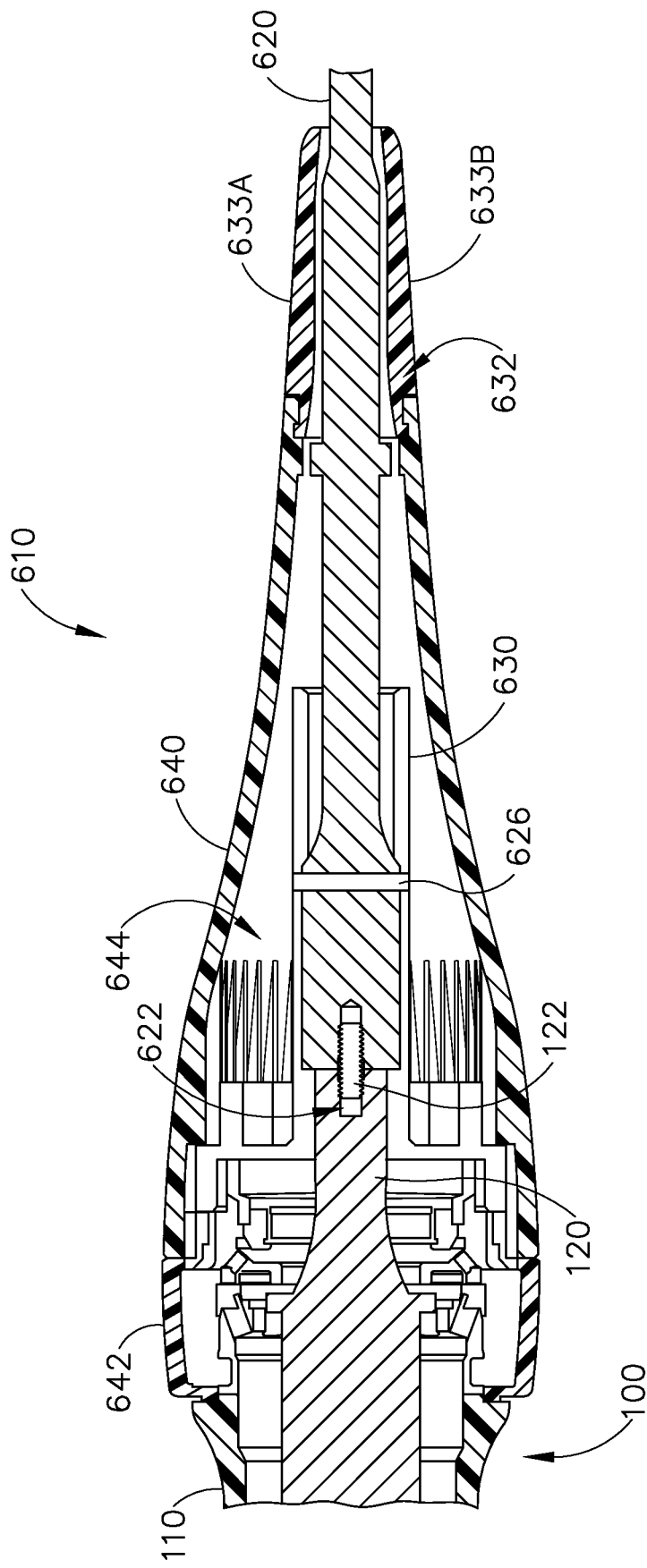
FIG. 30 depicts a partial cross-sectional view of the instrument of 28.

Sheath (630) defines a longitudinal interior bore (632) that passes completely through sheath (630) from a proximal end to a distal end thus defining a proximal opening and a distal opening. Sheath (630) is configured to receive waveguide (620) within interior bore (632). As best seen in FIG. 30, a pin (626) is passed through waveguide (620) and sheath (630) to thereby couple sheath (630) and waveguide (620) such that rotation of sheath (630) causes concurrent rotation of waveguide (620). Pin (626) is located at a position along the length of waveguide (620) corresponding to a node associated with resonant ultrasonic vibrations communicated through waveguide (620).

Figure 28:
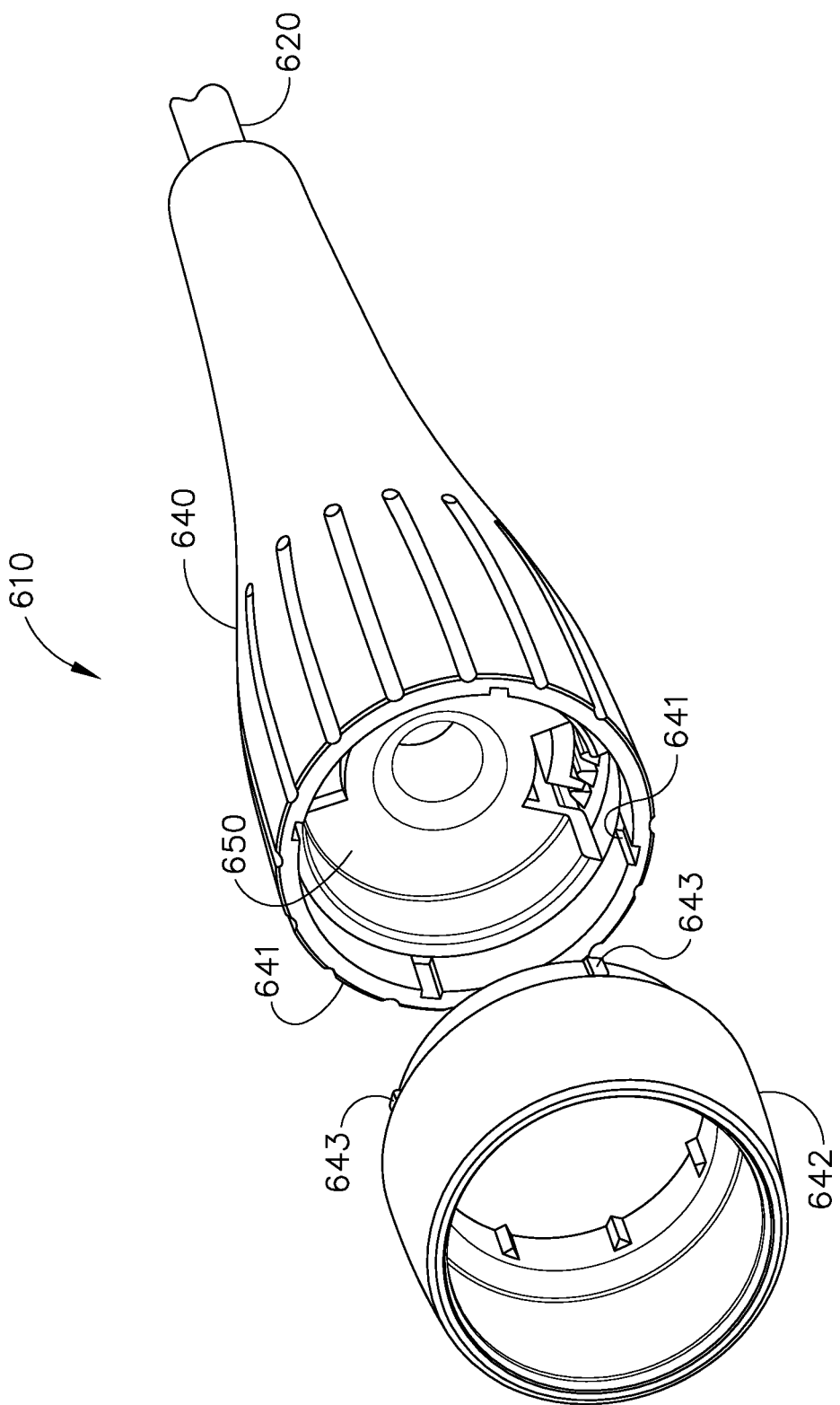
FIG. 28 depicts an exploded perspective view of an exemplary shaft assembly of yet another exemplary alternative instrument that uses the ratcheting assembly of FIG. 27A.
Figure 31:
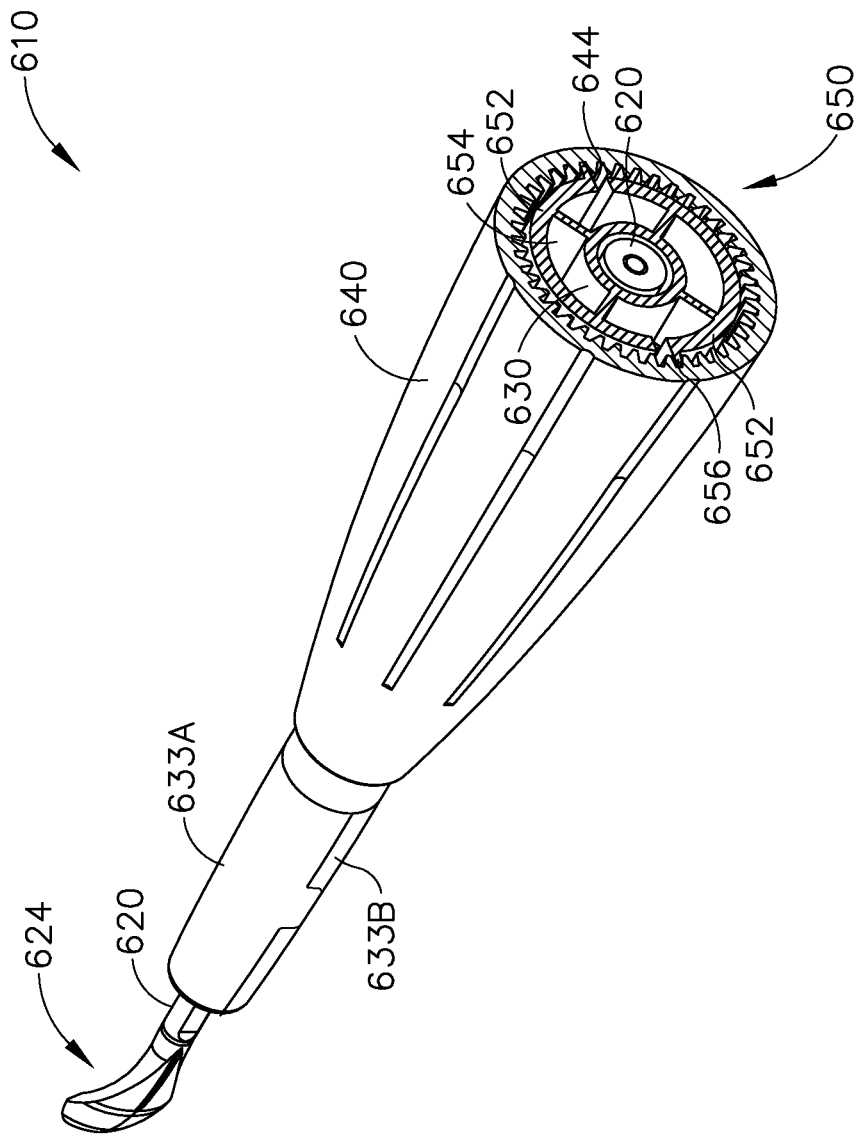
FIG. 31 depicts a perspective view of the shroud assembly of the instrument of FIG. 28.
Figure 32:
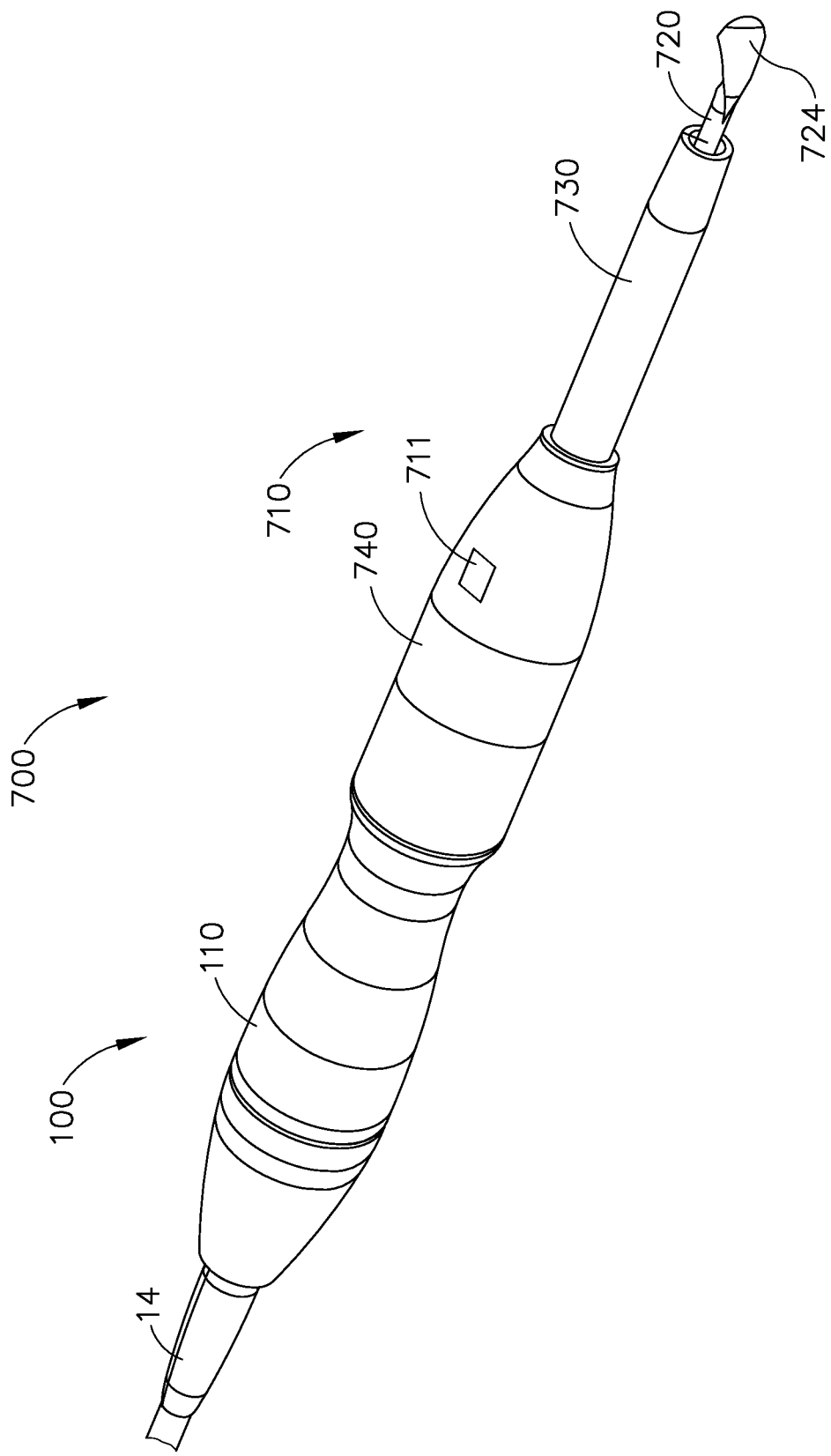
FIG. 32 depicts a perspective of yet another exemplary alternative surgical instrument.

As best seen in FIGS. 28 and 31, a proximal end of sheath (630) includes a torque assembly (650). Torque assembly (650) is configured to operate substantially similar to torque assembly (550) discussed above. For instance, torque assembly (650) comprises a pair of semi-circular resilient members (652) coupled to an exterior surface of sheath (630) via a corresponding pair of projections (654). Each resilient member (652) includes an outwardly extending tab (656). Shroud (640) comprises a plurality of inwardly extending longitudinal projections (642) disposed in an angular array about an interior surface of shroud (640). Longitudinal projections (642) are configured to engage tabs (656) of resilient members (652) such that shroud (640) may be used to rotate and sheath (630) and waveguide (620) relative to transducer assembly (100). Resilient members (652) are further configured to provide slipping of tabs (656) relative to projections (642) to thereby effectively limit the amount of torque that may be applied to waveguide (620) by shroud (640).

It should be understood from the foregoing that, as the user rotates rotate shaft assembly (610) relative to transducer assembly (100) to mechanically and acoustically couple waveguide (620) with horn (120), torque assembly (650) may operate as described above with respect to FIGS. 27A-27C. In particular, as the user rotates shroud (640) clockwise relative to transducer assembly (100) through a first range of motion, projections (644) and tabs (656) cooperate to drive sheath (630) clockwise, thereby rotating waveguide (620) clockwise relative to transducer assembly (100) through a first range of motion. During this first range of motion, tabs (656) continue to engage projections (644) such that torque assembly (650) rotates sheath (630) and waveguide (620) relative to transducer assembly (100). Waveguide (620) is thereby coupled with threaded stud (122).

As the user completes the first range of motion, waveguide (620) is secured to threaded stud (122) with a certain predetermined amount of torque. Once the assembly of waveguide (620) and threaded stud (122) reaches the predetermined amount of torque, and the user continues to rotate shroud (640) clockwise relative to transducer assembly (100) past the first range of motion, resilient members (652) deflect inwardly, such that shroud (640) no longer rotates sheath (630). Sheath (630) and waveguide (620) thus remain rotationally stationary at this stage. As the user continues to rotate shroud (640), tabs (656) eventually clear projections (644) and snap outwardly, thereby providing audible and/or tactile feedback to indicate to the user that an appropriate amount of torque has been achieved in the coupling of waveguide (620) with threaded stud (122). It should be understood that from this point on, any further clockwise rotation of shroud (640) no longer causes rotation of sheath (630) and waveguide (630) relative to transducer assembly (100). To remove shaft assembly (610) from transducer assembly (100), the user may simply grasp shroud (640) and rotate shaft assembly (610) counterclockwise relative to transducer assembly (100). At this stage, shaft assembly (610) may be disposed of; while transducer assembly (100) may be reconditioned any re-used. Alternatively, the user may wish to handle these components in some other fashion.

Figure 29:
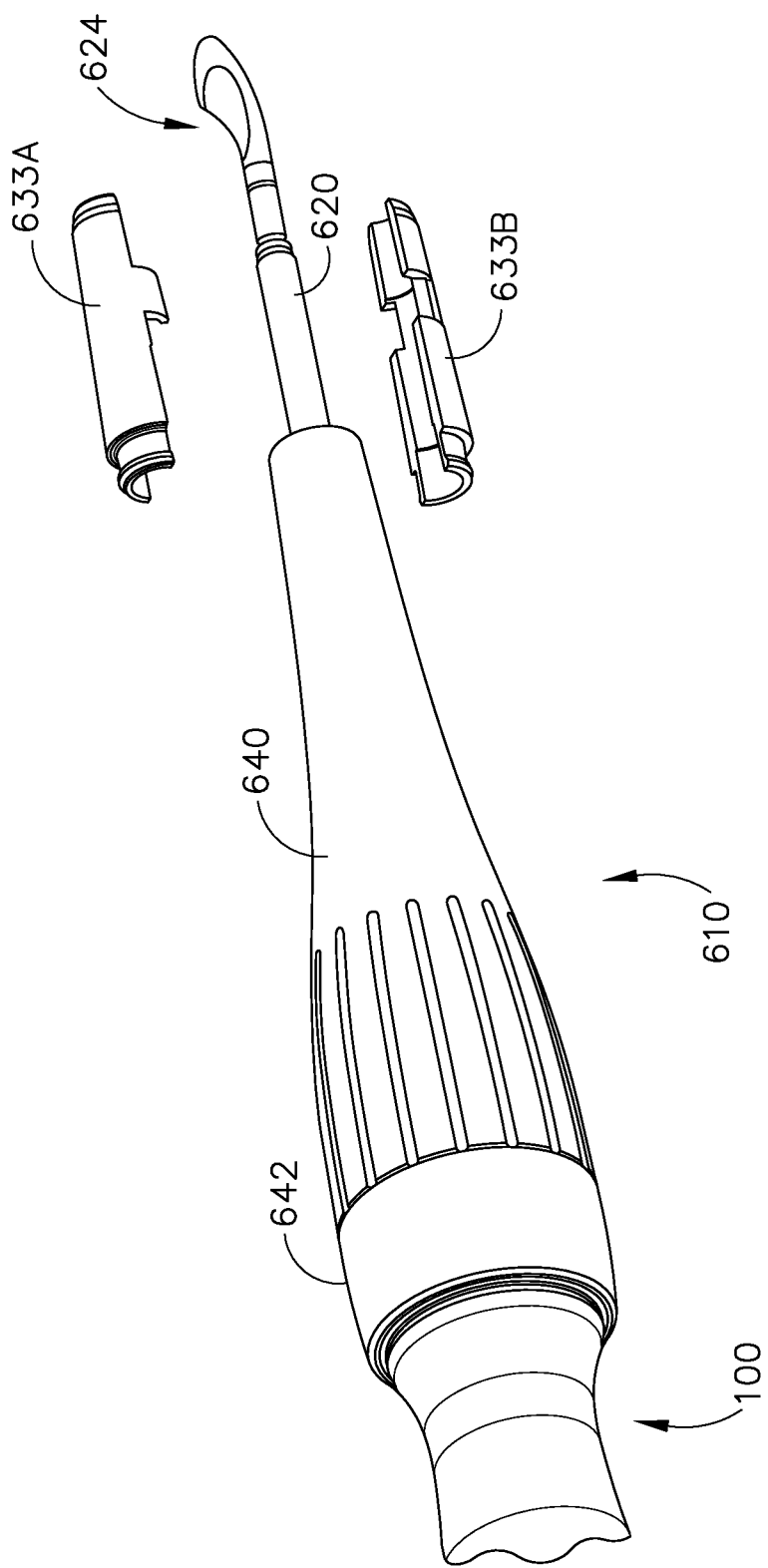
FIG. 29 depicts a perspective view of the shaft assembly of FIG. 28 coupled with the transducer of FIG. 2A.

As noted above, the integral torque assembly features of shaft assembly (610) eliminate the need for a separate torque wrench (e.g., such as torque wrench (50), etc.) to secure waveguide (620) with horn (120). It should also be understood that, during use of assembled instrument (600), the distal portion of sheath (630) proximal to ultrasonic blade (624) may be grasped by a user during operation to grasp instrument (600) in a pencil-like manner. Holding instrument (600) with a pencil grip may enable the user to provide very fine and precise movement with blade (624), such as in a facial plastic surgery procedure or some other fine and precise surgical procedure. In the present example, the distal portion of sheath (630) comprises an ergonomic overmold (633) that is configured to facilitate gripping of instrument (600) using a pencil grip. As shown in FIG. 29, overmold (633) comprises a first piece (633A) and a second piece (633B) such that overmold (633) may be selectively coupled to a distal end of shroud (640) and/or be otherwise secured relative to waveguide (620). Other suitable features will be apparent to those of ordinary skill in the art in view of the teachings herein.

F. Exemplary Integral Torque Assembly with Slide-On Shroud

FIGS. 32-36 show another exemplary instrument (700) having an integral torque assembly. Instrument (700) of the present example is configured to operate substantially similar to instruments (10, 200, 300, 400, 500, 600) discussed above except for the differences discussed below. In particular, instrument (700) is operable to transect and/or seal the tissue at a surgical site. Furthermore, the torque assembly discussed below is configured to operate substantially similar to the torque assemblies that included torque members (250, 350), and torque assemblies (450, 550, 650) discussed above except for the differences discussed below. In particular, the torque assembly discussed below is configured to limit the amount of torque that may be applied to couple a waveguide (720) with transducer assembly (100); and provide audible/tactile feedback to indicate that the appropriate amount of torque has been achieved.

Figure 34:
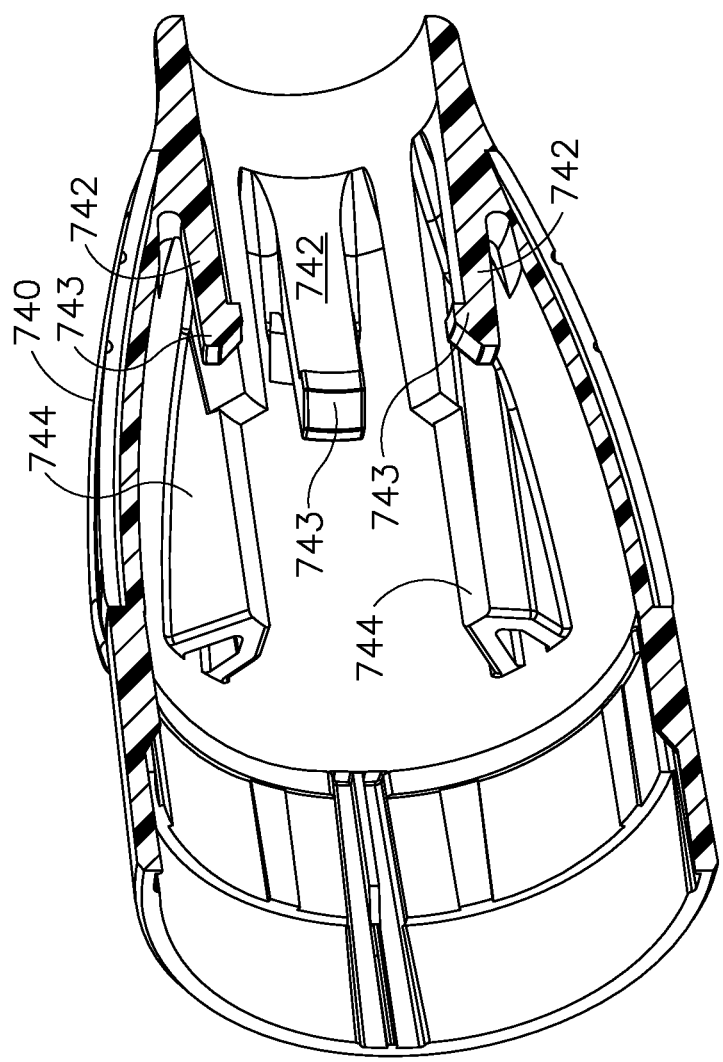
FIG. 34 depicts a perspective view of a cross-section of a shroud of the instrument of FIG. 32.

Instrument (700) of the present example comprises transducer assembly (100) and a shaft assembly (710). Shaft assembly (710) comprises a waveguide (720), a sheath (730), a shroud (740), and a connector (760). Shaft assembly (610) also includes a user input feature (711) that is operable to selectively activate transducer assembly (100), to thereby selectively activate ultrasonic blade (724) of waveguide (720). User input feature (711) may be constructed and operable in accordance with the teachings herein relating to user input feature (211) of instrument (200). As best seen in FIG. 34, shroud (740) includes an angular array of proximally projecting arms (742). An inwardly extending latching feature (743) is positioned at the free end of each arm (742). Arms (742) are resiliently biased to assume the straight configurations shown in FIG. 34. As also shown in FIG. 34, shroud (740) also includes an angular array of inwardly projecting projections (744) that extend longitudinally along part of the length of the interior of shroud (740).

Figure 35:
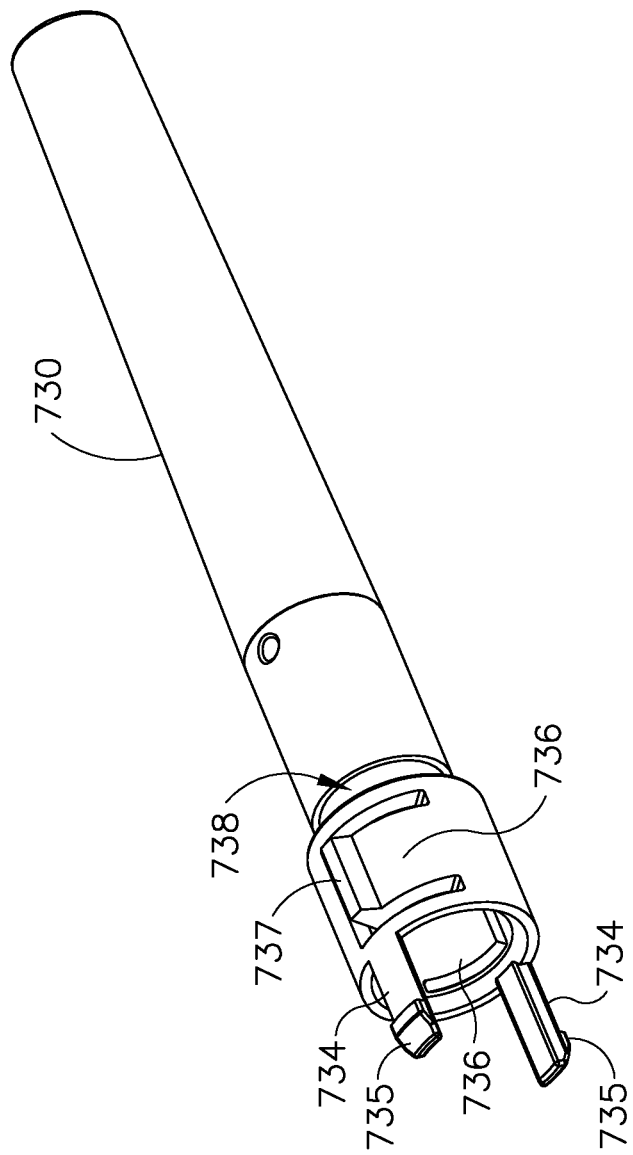
FIG. 35 depicts a perspective view of a sheath of the instrument of FIG. 32.

Sheath (730) defines a longitudinal interior bore (732) that passes completely through sheath (730) from a proximal end to a distal end thus defining a proximal opening and a distal opening. As best seen in FIG. 35, the proximal end of sheath (730) further includes a pair of proximally projecting arms (734). An outwardly extending latching feature (735) is positioned at the free end of each arm (734). Arms (734) are resiliently biased to assume the straight configurations shown in FIG. 35. As also shown in FIG. 35, sheath (730) further includes a pair of diametrically opposed resilient features (736). Resilient features (736) each include a respective outwardly oriented tab (737). In addition, sheath (730) includes an annular recess (738) that is formed distal to resilient features (736).

Figure 33A:
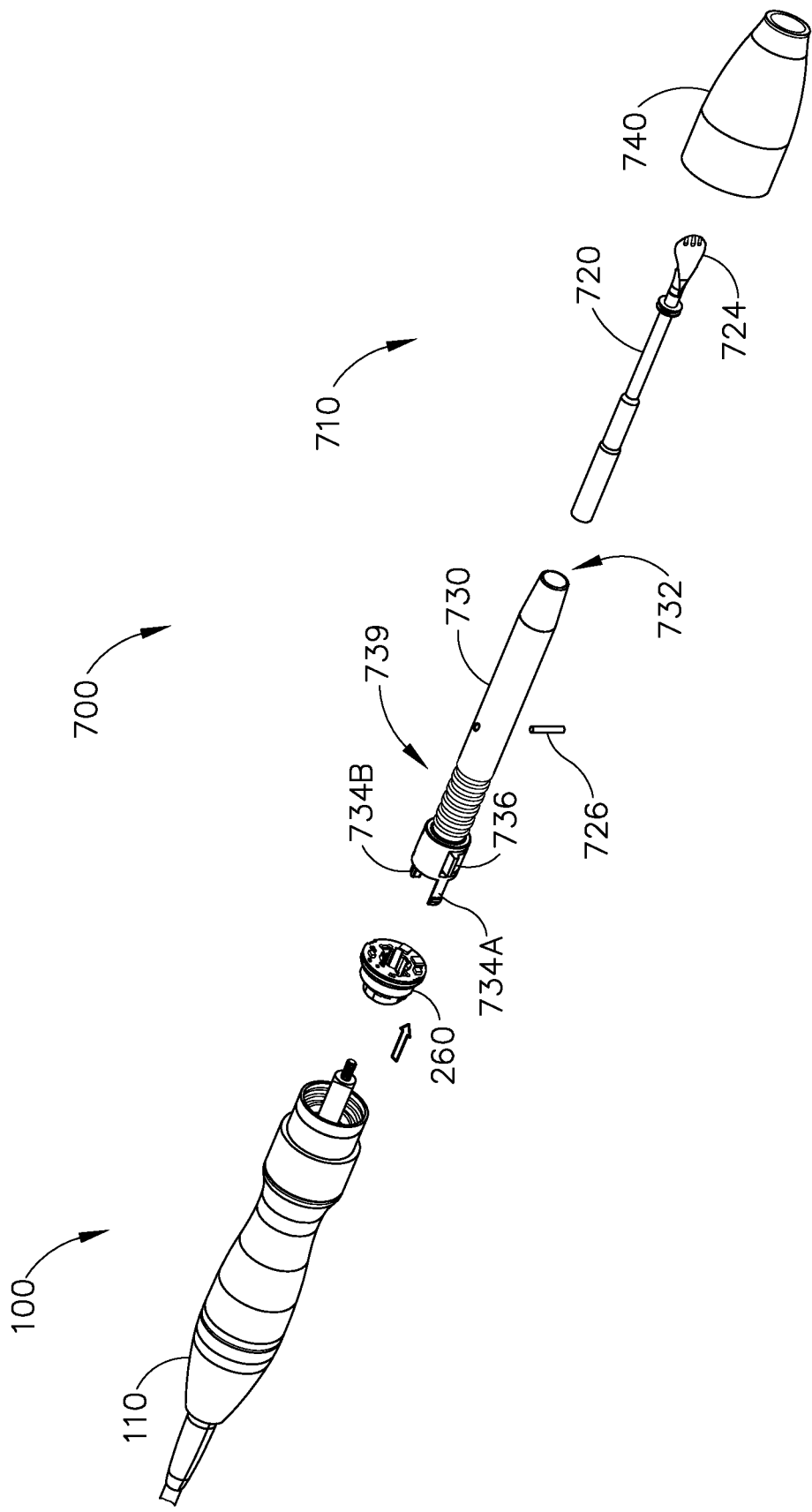
FIG. 33A depicts an exploded perspective view of the instrument of FIG. 32, showing the instrument in a disassembled state.
Figure 33B:
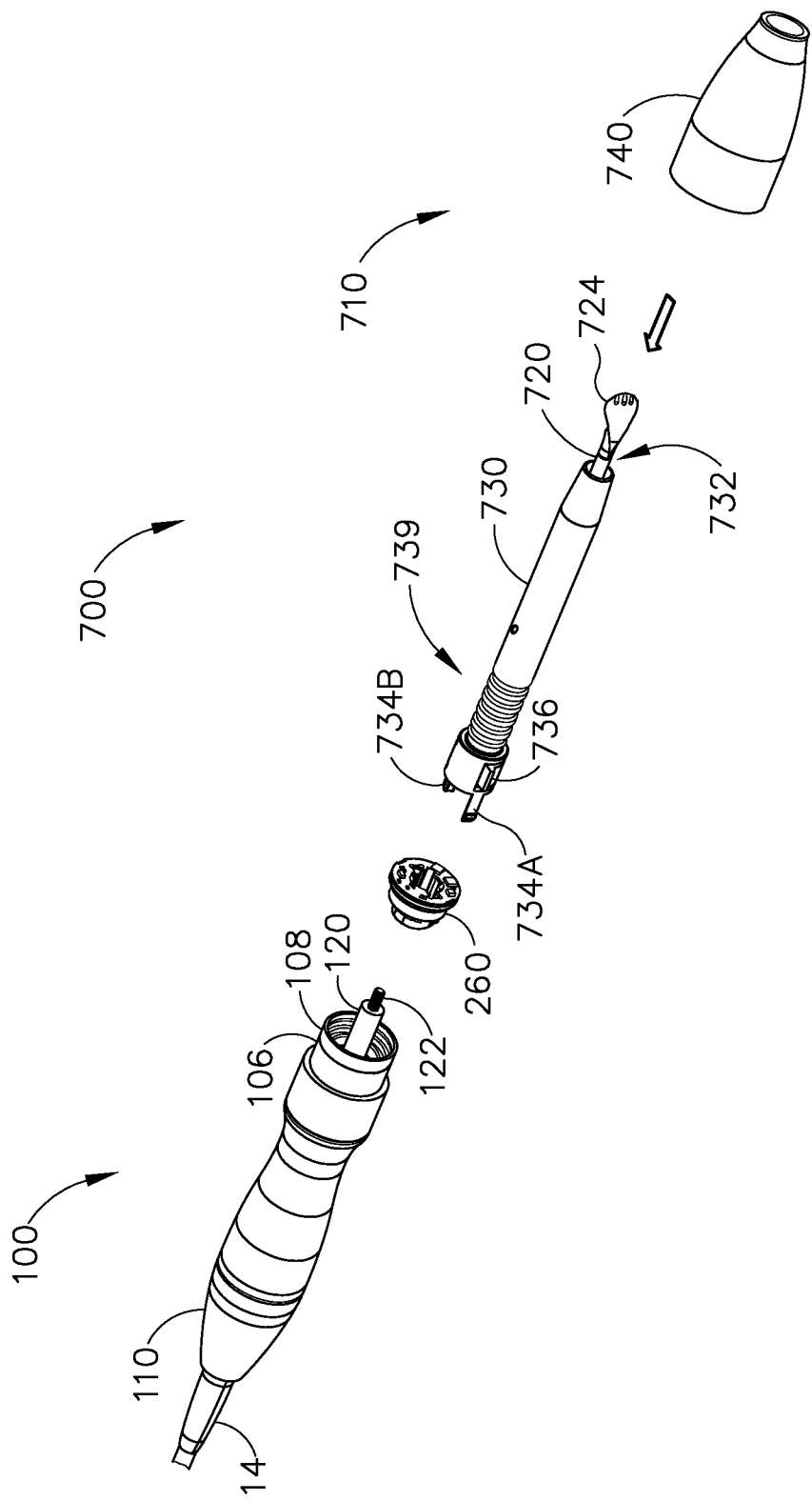
FIG. 33B depicts an exploded perspective view of the instrument of FIG. 32, showing the instrument in a first partially assembled state.

FIGS. 33A-33E show exemplary assembly steps of instrument (700). FIG. 33A shows instrument (700) in a disassembled state, including shaft assembly (710) in a disassembled state. In an initial assembly step, waveguide (720) is inserted into interior bore (732) of sheath (730) such that ultrasonic blade (724) of waveguide (720) extends from the distal end of sheath (730) as shown in FIG. 33B. A pin (726) is passed through aligned openings in sheath (730) and waveguide (720) to thereby couple sheath (730) and waveguide (720), such that rotation of sheath (730) causes concurrent rotation of waveguide (720). It should therefore be understood that sheath (730) and waveguide (720) rotate together unitarily when shaft assembly (710) is fully assembled. Pin (726) is inserted at a position along the length of waveguide (720) corresponding to a node associated with resonant ultrasonic vibrations communicated through waveguide (720), such that the ultrasonic vibrations are not communicated to pin (726).

Figure 33C:
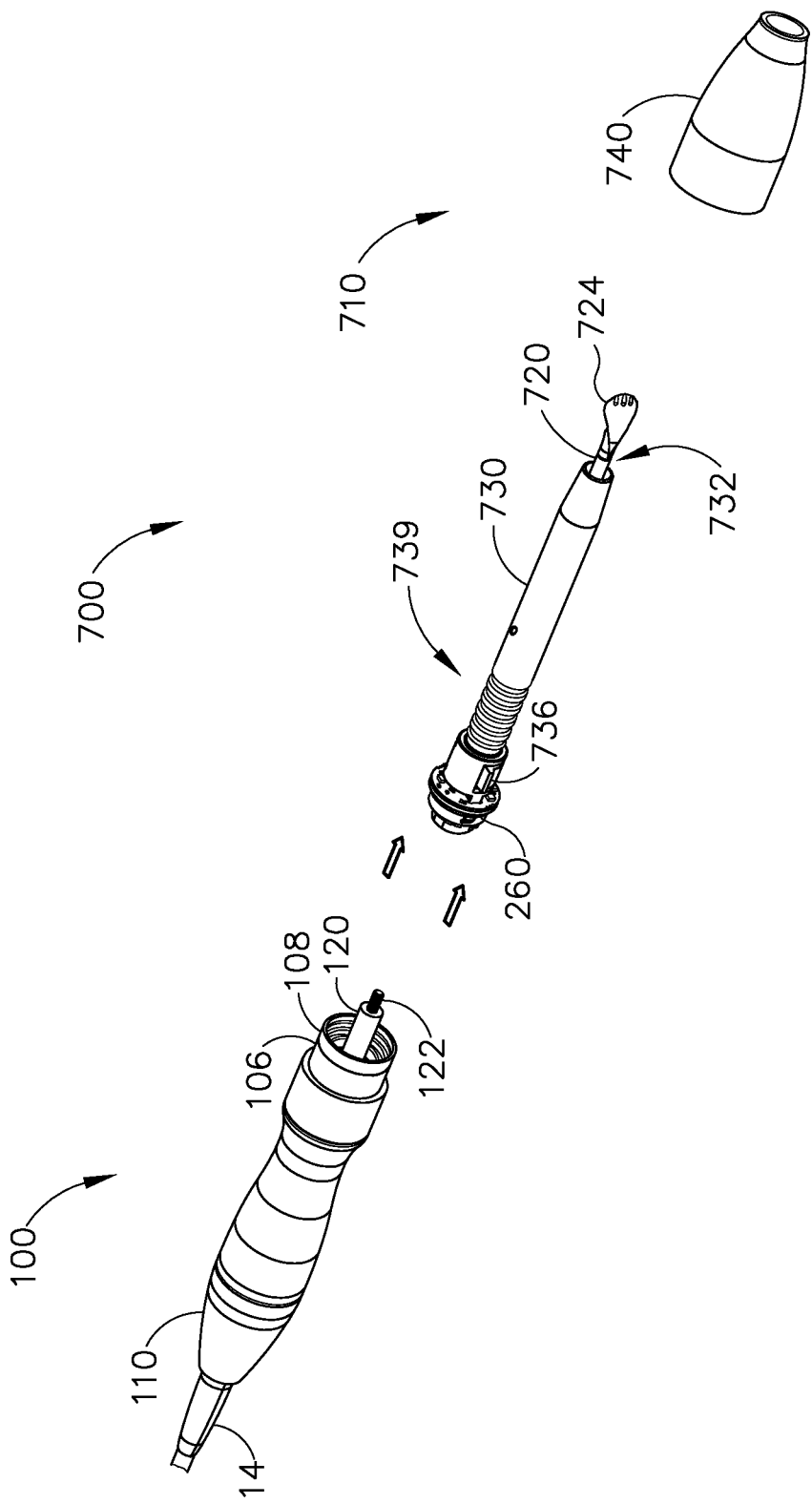
FIG. 33C depicts an exploded perspective view of the instrument of FIG. 32, showing the instrument in a second partially assembled state.
Figure 36:
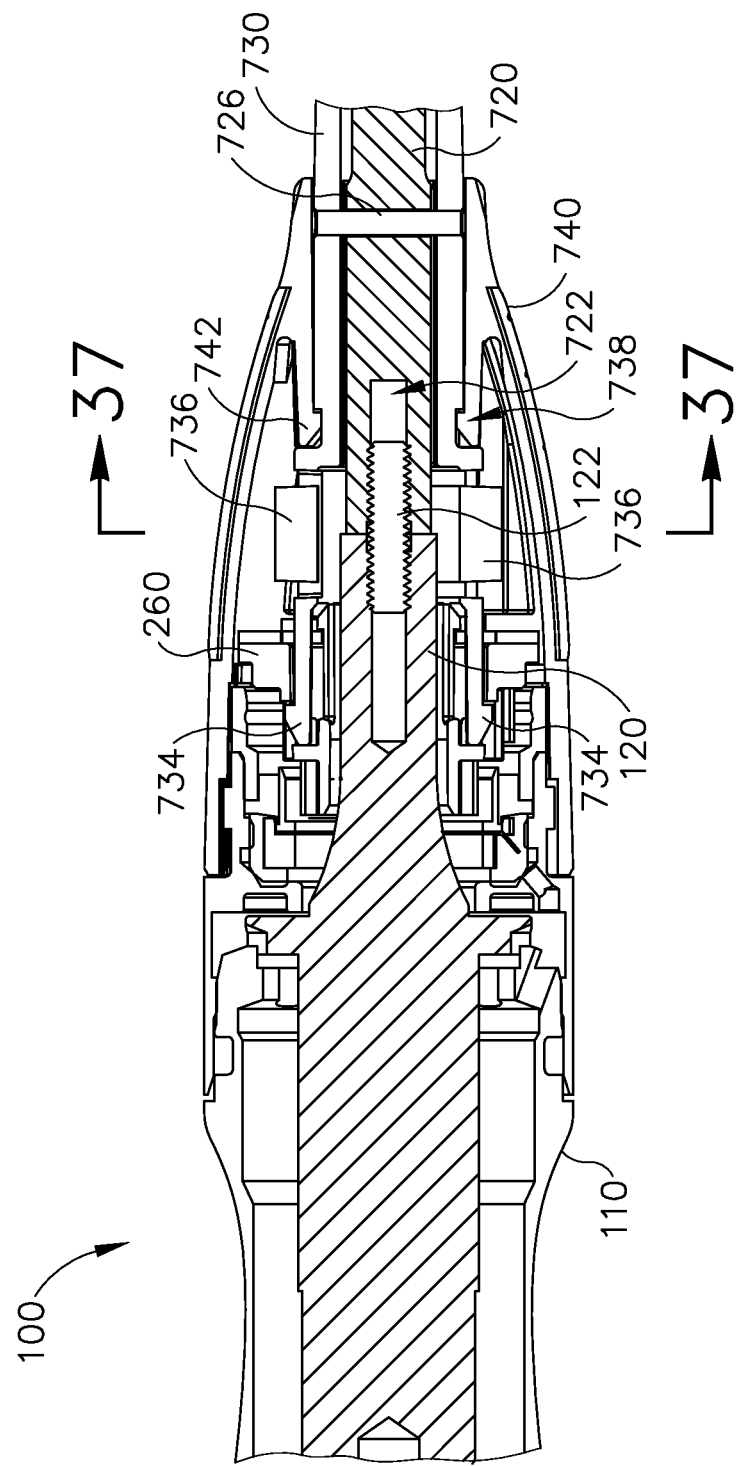
FIG. 36 depicts a partial cross-sectional side view of the instrument of FIG. 32.

With sheath (730) and waveguide (720) coupled together, connector (260) is then coupled to arms (734) of sheath (730) as shown in FIGS. 33C and 36. In particular, latching features (735) cam against openings (not shown) formed in connector (260), initially deflecting arms (734) inwardly as arms (734) are pressed into connector (260). Once latching features (734) clear the openings, the resilient bias drives arms (734) back outwardly to straight positions, such that latching features (734) engage corresponding proximal surfaces of connector (260). Connector (260) is thus secured to sheath (730) through a snap fit. As described above, connector (260) is configured to insertingly fit in cavity (108) of transducer assembly (100) and thereby guide shaft assembly (710) into aligned engagement with transducer assembly (100). As also described above, electrical contact features (262, 265) of connector (260) provide electrical coupling between user input feature (711) and transducer assembly (100).

Figure 33D:
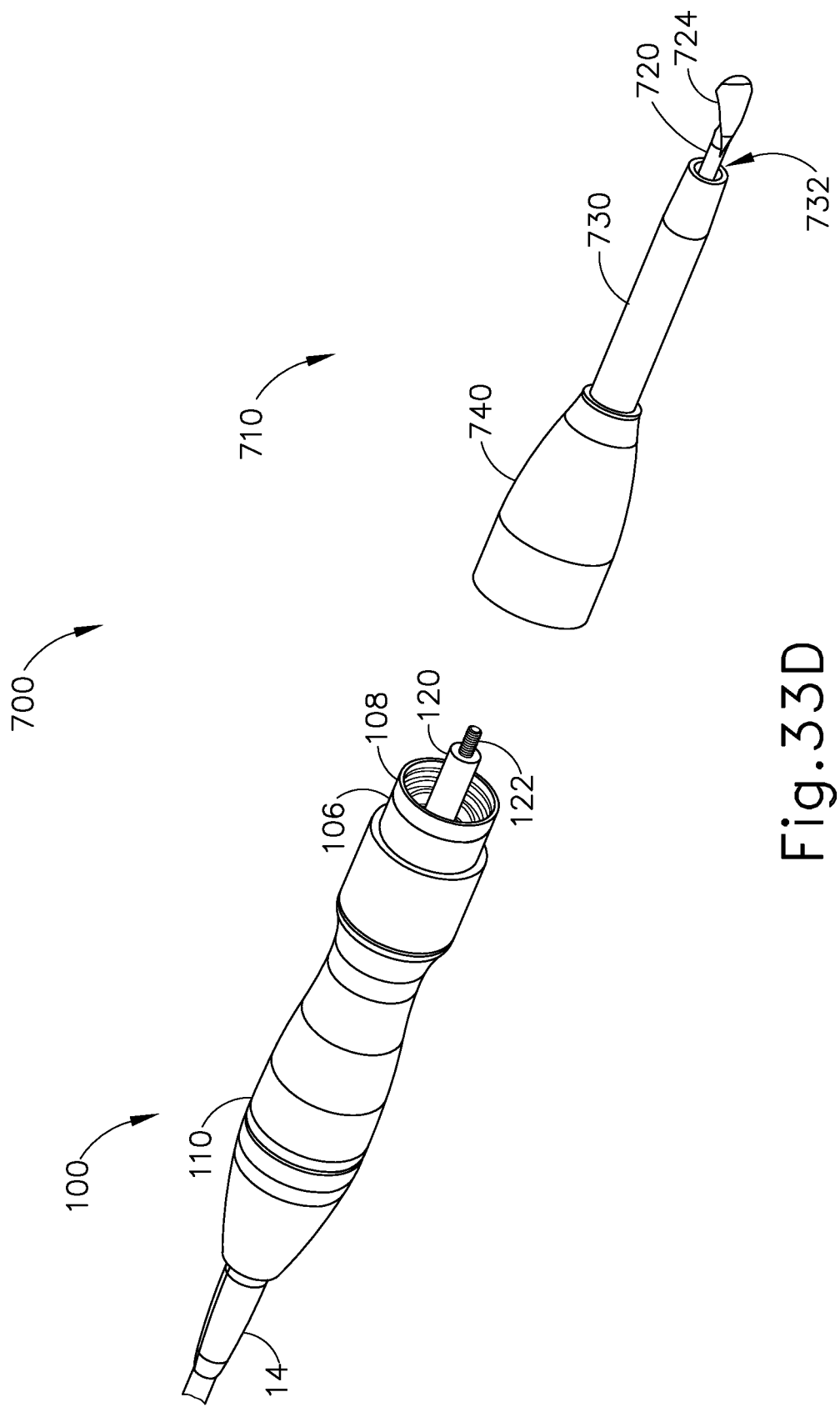
FIG. 33D depicts an exploded perspective view of the instrument of FIG. 32, showing the instrument in a third partially assembled state.

With connector (260) secured to sheath (730), shroud (740) is then slid proximally over sheath (730) as shown in FIG. 33D. During this movement, arms (742) of shroud (742) deflect outwardly until shroud (742) reaches a proximal position where latching features (743) are aligned with annular recess (738) of sheath (730). Upon reaching this position, the resilient bias of arms (742) drives latching features (743) inwardly into engagement with annular recess (738) as shown in FIG. 36. Shroud (740) is thus secured to sheath (730) through a snap fit. At this stage, shaft assembly (710) is completely assembled. It should be understood that shaft assembly (710) may be provided to an end user in the configuration shown in FIG. 33D, such that the end user need not perform any of the assembly steps shown in FIGS. 33A-33D.

Figure 33E:
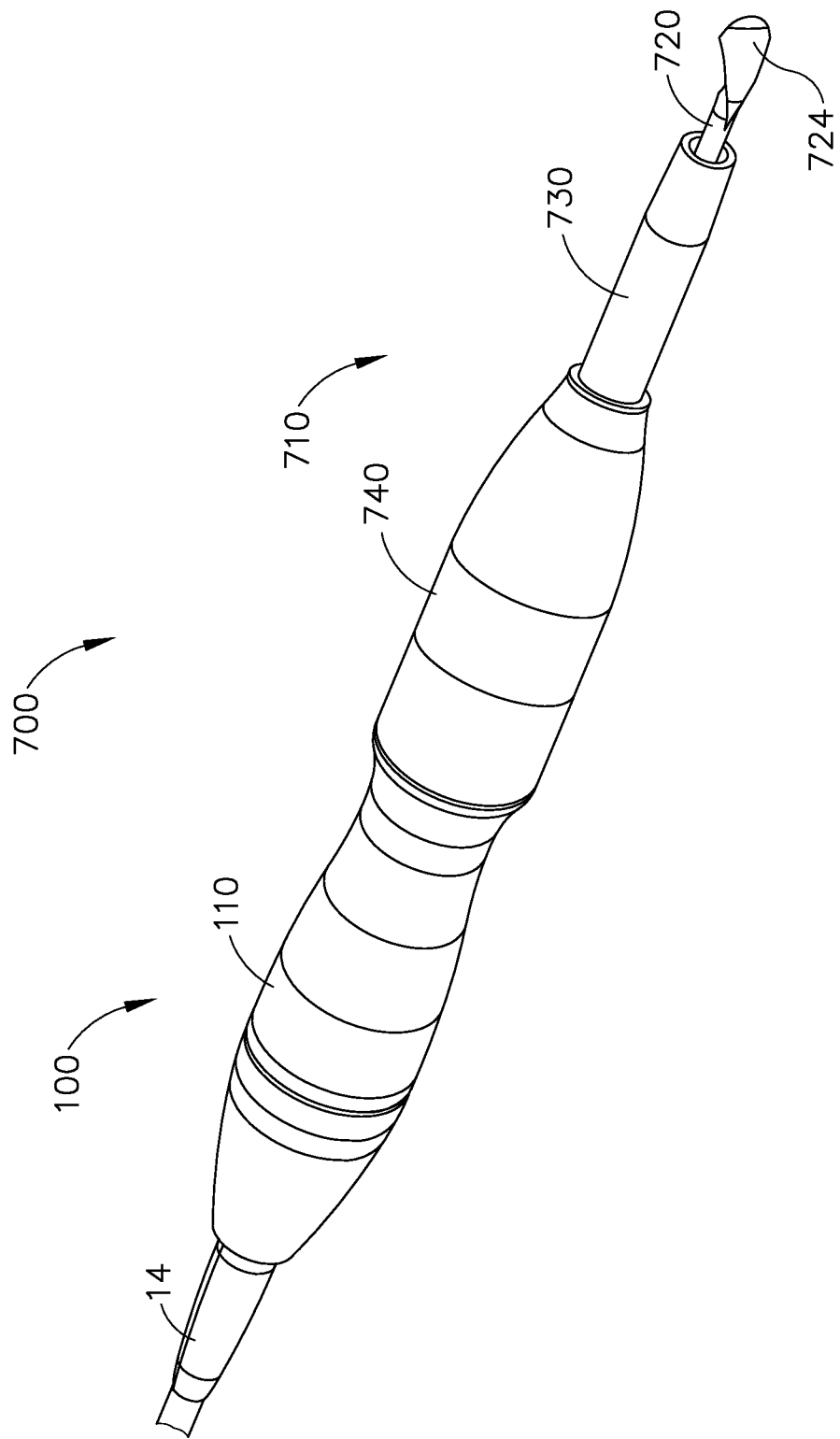
FIG. 33E depicts a perspective view of the instrument of FIG. 32, showing the instrument in an assembled state.

Once shaft assembly (710) has been fully assembled, shaft assembly (710) may be readily coupled with transducer assembly (100) as shown in FIG. 33E. In particular, the user may first maneuver shaft assembly (710) proximally toward transducer assembly (100). During this stage, connector (260) may assist in guiding shaft assembly (710) into axial alignment with transducer assembly (100) as noted above. The user may then grasp shroud (740) and rotate shaft assembly (710) relative to transducer assembly (100) to mechanically and acoustically couple waveguide (720) with horn (120) via threaded stud (122) and a threaded bore (722) formed in a proximal end of waveguide (720). As the user rotates rotate shaft assembly (710) relative to transducer assembly (100) to mechanically and acoustically couple waveguide (720) with horn (120), projections (744) may engage tabs (737). With projections (744) engaging tabs (737), the user continues to rotate shroud (740) clockwise relative to transducer assembly (100) through a first range of motion. During this first range of motion, shroud (740)

rotates sheath (730) and waveguide (720) relative to transducer assembly (100). Waveguide (720) is thereby coupled with threaded stud (122).

As the user completes the first range of motion, waveguide (720) is secured to threaded stud (122) with a certain predetermined amount of torque. Once the assembly of waveguide (720) and threaded stud (122) reaches the predetermined amount of torque, and the user continues to rotate shroud (740) clockwise relative to transducer assembly (100) past the first range of motion, resilient features (736) deflect inwardly, such that shroud (740) no longer rotates sheath (730). As the user continues to rotate shroud (740), projections (744) eventually clear tabs (737) such that tabs snap outwardly. This outward snapping/ratcheting may provide audible and/or tactile feedback to indicate to the user that an appropriate amount of torque has been achieved in the coupling of waveguide (720) with threaded stud (122). It should be understood that from this point on, any further clockwise rotation of shroud (740) no longer causes rotation of sheath (730) and waveguide (720) relative to transducer assembly (100). It should also be understood that the rigidity of resilient features (736) may be changed to thereby change the maximum amount of torque that may be applied to waveguide (720).

Tabs (737) of the present example are configured such that rotation of shroud (740) relative to transducer assembly (100) in a counterclockwise motion will not cause slipping or ratcheting of resilient features (736). Thus, when the user wishes to disassemble shaft assembly (710) from transducer assembly (100) at the end of a surgical procedure, the user may simply grasp shroud (740) with one hand and rotate shroud (740) counterclockwise relative to transducer assembly (100) while gripping transducer assembly (100) with the other hand, until waveguide (720) is decoupled from threaded stud (122) of transducer assembly (100). The user may then simply pull shaft assembly (710) away from transducer assembly (100). At this stage, shaft assembly (710) may be disposed of; while transducer assembly (100) may be reconditioned any re-used. Alternatively, the user may wish to handle these components in some other fashion.

It should be understood that the integral torque assembly features of shaft assembly (710) eliminate the need for a separate torque wrench (e.g., such as torque wrench (50), etc.) to secure waveguide (720) with horn (120). It should also be understood that, during use of assembled instrument (700), the distal portion of sheath (730) proximal to ultrasonic blade (724) may be grasped by a user during operation to grasp instrument (700) in a pencil-like manner. Holding instrument (700) with a pencil grip may enable the user to provide very fine and precise movement with blade (724), such as in a facial plastic surgery procedure or some other fine and precise surgical procedure.

III. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 5004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a transducer assembly, wherein the transducer assembly is operable to convert electrical power into ultrasonic vibrations; and
   (b) a shaft assembly, wherein the shaft assembly comprises:
      (i) an ultrasonic waveguide, wherein the ultrasonic waveguide is configured to couple with the transducer assembly,
      (ii) a sheath, wherein the ultrasonic waveguide is disposed within the sheath,
      (iii) a shroud defining an interior bore, wherein the sheath extends through the shroud, wherein the sheath extends distally past the shroud, and
      (iv) a torque transfer assembly at least partially contained within the interior bore of the shroud, wherein the torque transfer assembly is configured to transfer a predetermined range of torque from the shroud to the ultrasonic waveguide to thereby couple the ultrasonic waveguide with the transducer assembly, and wherein the torque transfer assembly is further configured to rotate relative to the sheath and the ultrasonic waveguide to prevent transfer of torque from the shroud to the ultrasonic waveguide beyond an upper limit of the predetermined range.

2. The surgical instrument of claim 1, wherein the torque transfer assembly comprises a resilient member resiliently biased toward a first position, and wherein the resilient member is configured to transfer torque from the shroud to the ultrasonic waveguide when the resilient member is in the first position.

3. The surgical instrument of claim 2, wherein the sheath is operable to drive the resilient member to a second position in response to the torque exceeding the upper limit of the predetermined range.

4. The surgical instrument of claim 3, wherein the resilient member is unable to transfer torque from the shroud to the ultrasonic waveguide when the resilient member is in the second position.

5. The surgical instrument of claim 1, wherein the sheath is secured to the ultrasonic waveguide, and wherein the torque transfer assembly is configured to transfer the predetermined range of torque from the shroud to the ultrasonic waveguide via the sheath.

6. The surgical instrument of claim 5, wherein the sheath comprises a plurality of longitudinal projections configured to receive the predetermined range of torque from the shroud of the ultrasonic waveguide.

7. The surgical instrument of claim 6, wherein the plurality of longitudinal projections are arranged in a circumferential array.

8. The surgical instrument of claim 6, wherein each of the plurality of longitudinal projections comprises an angular surface and a substantially flat surface.

9. The surgical instrument of claim 1, wherein the torque transfer assembly defines a longitudinal channel, and wherein the shroud is configured to engage the longitudinal channel to transfer torque from the shroud to the torque transfer assembly.

10. The surgical instrument of claim 1, further comprising a retaining ring, wherein the shroud includes a first body and a second body, and wherein the retaining ring is configured to couple the first body and the second body such that the shroud at least partially contains the torque transfer assembly.

11. The surgical instrument of claim 10, wherein the first body and the second body collectively define a recess dimensioned to receive the retaining ring.

12. The surgical instrument of claim 11, wherein the retaining ring is configured to couple with the first body and the second body via a friction fitting.

13. The surgical instrument of claim 1, wherein the torque transfer assembly comprises a resilient tab configured to prevent transfer of torque from the shroud to the ultrasonic waveguide beyond the upper limit of the predetermined range in a first rotational direction.

14. The surgical instrument of claim 13, wherein the resilient tab is configured to allow transfer of torque from the shroud to the ultrasonic waveguide beyond the upper limit of the predetermined range in a second rotational direction.

15. The surgical instrument of claim 14, wherein the resilient tab comprises an angled surface and a substantially flat surface.

16. The surgical instrument of claim 15, wherein the substantially flat surface is configured to engage the sheath in the second rotational direction.

17. The surgical instrument of claim 16, wherein the angled surface is configured to engage the sheath in the first rotational direction.

18. A surgical instrument, comprising:
   (a) a transducer assembly, wherein the transducer assembly is operable to convert electrical power into ultrasonic vibrations; and
   (b) a shaft assembly, wherein the shaft assembly comprises:
      (i) an ultrasonic waveguide, wherein the ultrasonic waveguide is configured to couple with the transducer assembly,
      (ii) a sheath, wherein the ultrasonic waveguide is disposed within the sheath,
      (iii) a shroud, wherein at least part of the ultrasonic waveguide extends distally from the shroud, wherein the sheath extends distally past the shroud, and
      (iv) a torque transfer assembly at least partially contained within the shroud and disposed on the ultrasonic waveguide such that the torque transfer assembly is radially interposed between the shroud and the ultrasonic waveguide, wherein the torque transfer assembly is configured to transfer torque from the shroud to the ultrasonic waveguide to thereby couple the ultrasonic waveguide with the transducer assembly as the shroud is rotated through a first range of motion, wherein the torque transfer assembly is configured to unitarily rotate with the shroud to prevent the transfer of torque from the shroud to the ultrasonic waveguide as the shroud is rotated through a second range of motion.

19. The surgical instrument of claim 18, wherein the torque transfer assembly is configured such that a transition from the first range of motion to the second range of motion is associated with a predetermined torque threshold.

20. A surgical instrument, comprising:
   (a) a transducer assembly, wherein the transducer assembly is operable to convert electrical power into ultrasonic vibrations; and
   (b) a shaft assembly, wherein the shaft assembly comprises:

(i) an ultrasonic waveguide, wherein the ultrasonic waveguide is configured to couple with the transducer assembly,
(ii) a shroud defining an interior bore, wherein at least a portion of the ultrasonic waveguide is housed within the shroud, and
(iii) a torque transfer assembly housed within the interior bore of the shroud, wherein the torque transfer assembly is configured to transfer a predetermined range of torque from the shroud to the ultrasonic waveguide to thereby couple the ultrasonic waveguide with the transducer assembly, wherein the torque transfer assembly is further configured to unitarily rotate with the shroud relative to the ultrasonic waveguide to prevent transfer of torque from the shroud to the ultrasonic waveguide beyond an upper limit of the predetermined range, wherein the torque transfer assembly defines a longitudinal channel, and wherein the shroud is configured to engage the longitudinal channel to transfer torque from the shroud to the torque transfer assembly.

* * * * *